(12) United States Patent
Park et al.

(10) Patent No.: US 12,283,257 B2
(45) Date of Patent: Apr. 22, 2025

(54) DISPLAY DEVICE HAVING OPTIMUM DISPLAY POSTURE AND METHOD FOR CONTROLLING THE SAME

(71) Applicant: LG ELECTRONICS INC., Seoul (KR)

(72) Inventors: Jinho Park, Seoul (KR); Hyunjae Jun, Seoul (KR); Junho Roh, Seoul (KR); Sangguel Oh, Seoul (KR); Taewoong Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 18/311,386

(22) Filed: May 3, 2023

(65) Prior Publication Data
US 2024/0065580 A1    Feb. 29, 2024

(30) Foreign Application Priority Data

Aug. 26, 2022  (KR) .................. 10-2022-0107893
Aug. 31, 2022  (KR) .................. 10-2022-0110289

(51) Int. Cl.
*G09G 5/00*   (2006.01)
*G06V 40/10*  (2022.01)

(52) U.S. Cl.
CPC .......... *G09G 5/003* (2013.01); *G06V 40/103* (2022.01); *G09G 2320/08* (2013.01)

(58) Field of Classification Search
None
See application file for complete search history.

(56) References Cited

U.S. PATENT DOCUMENTS 9,794,516 B1 *    10/2017    Tuli ................. H04N 21/42204
2009/0174658 A1 *  7/2009    Blatchley ............. G06F 1/1601
                                                         345/158

(Continued)

FOREIGN PATENT DOCUMENTS

KR    10-2017-0105865 A    9/2017
KR    10-2018-0090961 A    8/2018

(Continued)

*Primary Examiner* — Amr A Awad
*Assistant Examiner* — Donna V Bocar
(74) *Attorney, Agent, or Firm* — Birch, Stewart, Kolasch & Birch, LLP

(57) ABSTRACT

A display device including a display unit having a display panel and a camera; a posture adjustment driving unit configured to adjust a posture of the display unit; and a controller configured to control the camera to capture a first image of a viewer viewing the display unit when the display unit is positioned at a first height, control the posture adjustment driving unit to move the display unit to a second height different than the first height, control the camera to capture a second image of the viewer viewing the display unit when the display unit is positioned at the second height, correct at least one of the first image and the second image based on orientation information of the display unit on capturing the first image and the second image, generate a 3D body mesh of the viewer using the first image and the second image, calculate a viewer-optimized display unit posture setting based on the 3D body mesh, and control the posture adjustment driving unit to move the display unit to a height corresponding to the viewer-optimized display unit posture setting.

17 Claims, 45 Drawing Sheets

(56) References Cited

U.S. PATENT DOCUMENTS

| | | | |
|---|---|---|---|
| 2016/0080662 A1* | 3/2016 | Saban | H04N 5/272 |
| | | | 348/77 |
| 2017/0263215 A1* | 9/2017 | Han | F16M 11/046 |
| 2022/0107684 A1 | 4/2022 | Files et al. | |
| 2022/0171478 A1* | 6/2022 | Wu | G06F 1/1601 |
| 2023/0065758 A1* | 3/2023 | Kwon | F16M 11/28 |

FOREIGN PATENT DOCUMENTS

| | | |
|---|---|---|
| KR | 10-2020-0080050 A | 7/2020 |
| KR | 10-2021-0121772 A | 10/2021 |

\* cited by examiner

FIG. 15
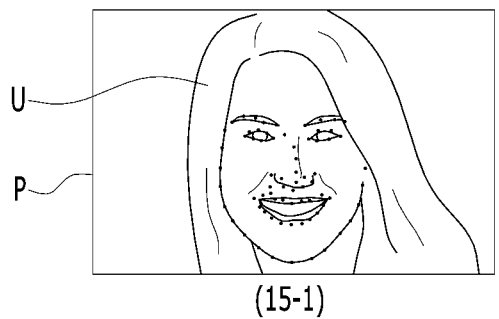
(15-1)
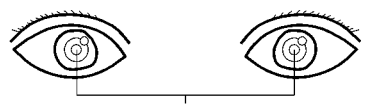
PD=62mm
(15-2)
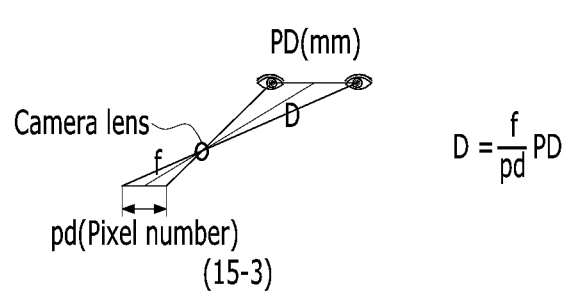
$$D = \frac{f}{pd} PD$$
(15-3)

FIG. 17
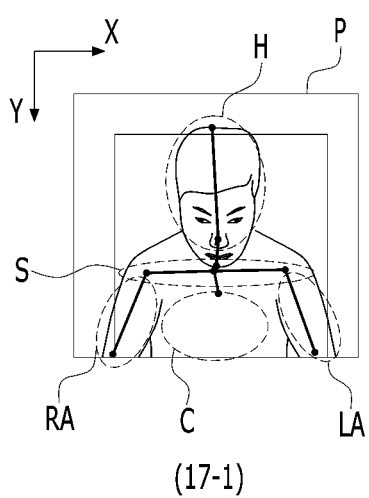
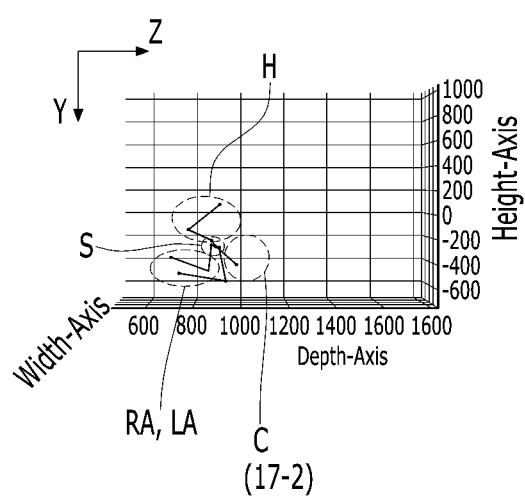
(17-1)  (17-2)

FIG. 18
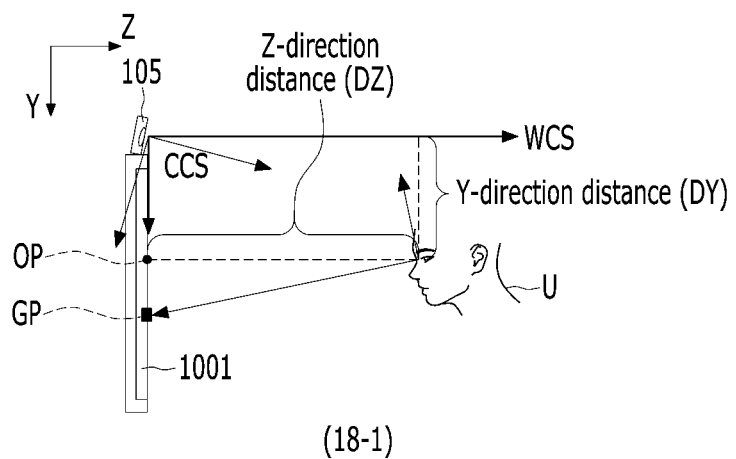
(18-1)
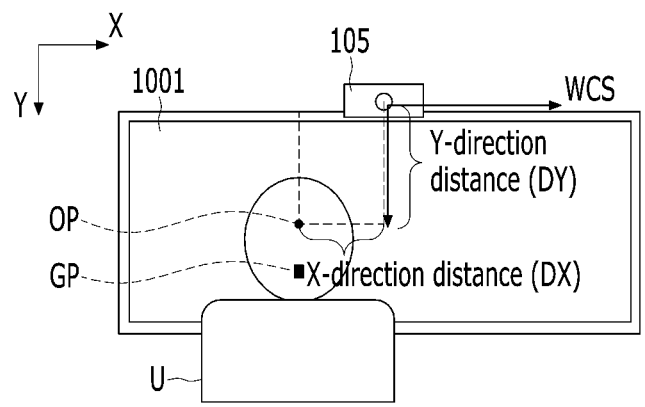
(18-2)

DISPLAY DEVICE HAVING OPTIMUM DISPLAY POSTURE AND METHOD FOR CONTROLLING THE SAME

CROSS-REFERENCE TO RELATED APPLICATIONS

This application claims the priority benefit under 35 U.S.C. § 119(a) to Korean Application Nos. 10-2022-0107893 and 10-2022-0110289, filed on Aug. 26, 2022 and Aug. 31, 2022, respectively, the contents of which are hereby incorporated by reference herein in their entirety.

BACKGROUND OF THE DISCLOSURE

Field of the Disclosure

The present disclosure relates to a display device and method of controlling the same, capable of adjusting a height and/or tilt angle of a display unit.

Discussion of the Related Art

As the information society develops, various display devices such as a Liquid Crystal Display (LCD), a Plasma Display Panel (PDP), an Electroluminescent Display (ELD), a Vacuum Fluorescent Display (VFD), and the like have been developed and used. Such a display device includes a display unit for displaying an image and a support device for supporting the display unit to be spaced apart from an upper surface of a desk and/or table by a preset height.

In such a display device of the related art, a user has to manually adjust a height and/or tilt angle of the display unit according to his or her posture, which is inconvenient, and it is quite cumbersome to adjust it one by one whenever the user's posture changes.

SUMMARY OF THE DISCLOSURE

The present disclosure is proposed to solve the above-mentioned problems and relates to a display device and control method thereof that can automatically adjust a posture of a display unit depending on a user's posture.

To achieve these and other advantages and in accordance with the purpose of the present disclosure as embodied and broadly described, in one technical aspect of the present disclosure, provided is a display device including a signal input unit, a display unit having a display panel and a camera, a supporter supporting the display unit, a posture adjustment driving unit provided to the supporter to adjust a posture of the display unit, and a controller controlling the posture adjustment driving unit to enable the posture of the display unit to match a feature point of a user face and a user posture inferred by an artificial intelligence model from a first user image obtained through the camera.

The controller can infer the user posture based on a spaced distance between the camera and the user calculated based on a feature point pixel distance between two feature points of the user face in the first user image.

The controller can calculate the feature point pixel distance based on 2D landmark information inferred from the first user image by the artificial intelligence model.

The controller can correct the feature point pixel distance based on 3D body skeleton information inferred from the first user image by the artificial intelligence model.

The controller can obtain a second user image using the user taking a user basic posture as a subject through the camera from a first height of the display unit, obtain a third user image using the user taking the user basic posture as the subject through the camera from a second height of the display unit, calculate a reference spaced distance between the display unit and the user based on the second user image and the third user image, calculate a reference pixel distance between the two feature points of the user face from the second user image or the third user image, and calculate the spaced distance between the camera and the user in the first user image further based on the reference spaced distance and the reference pixel distance.

The controller can control data for the reference spaced distance and the reference pixel distance to be stored in a manner of matching the user.

The controller can control the data for the reference spaced distance and the reference pixel distance to be stored if a horizontal (left-to-right) movement of the subject in the second user image and the third user image is within a prescribed pixel distance.

The controller can correct at least one of the second user image and the third user image based on orientation information of the display unit on obtaining the second user image and the third user image, and the controller can control the reference spaced distance and the reference pixel distance to be calculated based on the corrected second user image and the corrected third user image.

The two feature points of the user face can include both eyes.

The controller can generate a 3D body mesh of the user using the second user image and the third user image.

The controller can calculate a user-optimized display unit posture setting based on the 3D body mesh.

The controller can control the user-optimized display unit posture setting to be corrected by the user through the signal input unit.

Based on correcting the user-optimized display unit posture setting by the user, the controller can store the corrected posture setting as a user preference setting. Based on not correcting the user-optimized display unit posture setting by the user, the controller can store the user-optimized display unit posture setting as the user preference setting. The controller can control the posture adjustment driving unit to adjust the posture of the display unit in further consideration of the user preference setting.

The controller can control the posture adjustment driving unit further based on spatial relationship between the user basic posture on obtaining the second user image and the third user image and the user preference setting.

Based on detecting absence of the user in the first user image, the controller can control the posture adjustment driving unit to maintain the posture of the display unit at a timing point of detecting the absence. Based on continuously detecting the absence for a prescribed time from the timing point of detecting the absence, the controller can control the posture adjustment driving unit to adjust the posture of the display unit according to the user preference setting.

The controller can control the posture adjustment driving unit to adjust the posture of the display unit within a vertical (top-bottom) movement range of the display unit determined based on the user posture in the first user image.

The controller can determine the vertical movement range of the display unit further based on spatial relationship between the user basic posture and the user preference setting.

The controller can control the posture adjustment driving unit to adjust the posture of the display unit to have a height fluctuation of a sinusoidal curve trajectory continuous within the vertical movement range.

In addition, the controller can control the posture adjustment driving unit to maintain a height of the display unit at a random height within the vertical movement range.

In another technical aspect of the present disclosure, provided is a method of controlling a display device, the method including photographing a user image through a camera and controlling a posture of a display unit to match a feature point of a user face and a user posture inferred by an artificial intelligence model from the user image.

In another technical aspect of the present disclosure, provided is a display device including a signal input unit, a display unit having a display panel and a camera, a supporter supporting the display unit, a posture adjustment driving unit provided to the supporter to adjust a posture of the display unit, and a controller obtaining a first user image using a user as a subject from a first height of the display unit through the camera, obtaining a second user image using the user as the subject from a second height of the display unit through the camera, calculating a first spaced distance between the display unit and the user based on the first user image and the second user image, calculating a first pixel distance between two feature points of a face of the user from the first user image and the second user image, storing data about the first spaced distance and the first pixel distance with respect to the user, obtaining a third user image using the user as the subject through the camera, calculating a second pixel distance between the two feature points of the face of the user from the third user image, and controlling the posture adjustment driving unit to adjust the posture of the display unit based on a second spaced distance between the display unit and the user, the second spaced distance calculated based on a second pixel distance and the stored data.

The controller can control the data about the first spaced distance and the first pixel distance to be stored if a horizontal (left-to-right) movement of the subject in the second user image and the third user image is within a prescribed pixel distance.

The controller can correct at least one of the first user image and the second user image based on orientation information of the display unit on obtaining the first user image and the second user image, and the controller can control the first spaced distance and the first pixel distance to be calculated based on the corrected first user image and the corrected second user image.

The controller can calculate the second pixel distance based on 2D landmark information calculated from the third user image.

The controller can correct the second pixel distance based on 3D body skeleton information calculated from the third user image.

The two feature points of the user face can include both eyes.

The controller can control the posture adjustment driving unit based on a user posture in the third user image detected based on the second spaced distance.

The controller can generate a 3D body mesh of the user using the first user image and the second user image.

The controller can calculate a user-optimized display unit posture setting based on the 3D body mesh.

The controller can control the user-optimized display unit posture setting to be corrected by the user through the signal input unit.

Based on correcting the user-optimized display unit posture setting by the user, the controller can store the corrected posture setting as a user preference setting. Based on not correcting the user-optimized display unit posture setting by the user, the controller can store the user-optimized display unit posture setting as the user preference setting. Also, controller can control the posture adjustment driving unit to adjust the posture of the display unit in further consideration of the user preference setting.

The controller can control the posture adjustment driving unit further based on spatial relationship between the user basic posture on obtaining the second user image and the third user image and the user preference setting.

The controller can control the posture adjustment driving unit to enable the posture of the display unit to follow the user posture so as to maintain the spatial relationship.

The user posture mode can include a watch mode and a non-watch mode. If the user posture mode is the watch mode, the controller can control the posture adjustment driving unit to enable the posture of the display unit to follow the user posture. If the user posture mode is the non-watch mode, the controller can control the posture adjustment driving unit to enable the posture of the display unit not to follow the user posture.

If the user posture mode is the watch mode, the user posture mode can include a concentration mode and a relax mode. If the user posture mode is the concentration mode, the controller can control the posture adjustment driving unit to enable the display unit to move in the same direction as a user eye level according to the user posture.

If the user posture mode is the relax mode, the controller can control the posture adjustment driving unit to enable a height of the display unit to increase as the user eye level decreases.

If the user posture is a turtle neck posture, the controller can control a turtle neck posture warning to be output.

If the user posture is a turtle neck posture, the controller can control the posture adjustment driving unit to enable a height of the display unit t to increase while the posture of the display unit does not follow the user posture.

The controller can control the posture adjustment driving unit to enable the height of the display unit to increase until the user is out of the turtle neck posture.

In another technical aspect of the present disclosure, provided is a method of controlling a display device, the method including obtaining a first user image using a user as a subject from a first height of a display unit through a camera, obtaining a second user image using the user as the subject from a second height of the display unit through the camera, calculating a first spaced distance between the display unit and the user based on the first user image and the second user image, calculating a first pixel distance between two feature points of a face of the user from the first user image and the second user image, storing data about the first spaced distance and the first pixel distance with respect to the user, obtaining a third user image using the user as the subject through the camera, calculating a second pixel distance between the two feature points of the face of the user from the third user image, and adjusting a posture of the display unit based on a second spaced distance between the display unit and the user, the second spaced distance calculated based on a second pixel distance and the stored data.

In another technical aspect of the present disclosure, provided is a display device including a signal input unit, a display unit having a display panel and a camera, a supporter supporting the display unit, a posture adjustment driving unit provided to the supporter to adjust a posture of the display unit, and a controller controlling the posture adjustment driving unit to adjust a posture of the display unit within a vertical movement range of the display unit determined based on a first user posture in a first user image photographed through the camera.

The controller can determine the vertical movement range of the display unit further based on spatial relationship between a user basic posture and a user preference setting.

The controller can control the posture adjustment driving unit to adjust the posture of the display unit to have a height fluctuation of a continuous sinusoidal curve trajectory within the vertical movement range.

The controller can control the posture adjustment driving unit to update the vertical movement of the display unit based on the user preference setting and a second user image photographed through the camera after adjusting the posture of the display unit within the vertical movement range for one period and adjust the posture of the display unit within the updated vertical movement range for a next period.

The controller can control an initial height of the sinusoidal curve trajectory to vary depending on a height of the display unit at a time point of determining the vertical movement range.

Based on the height of the display unit within the vertical movement range, the controller can control the height of the display unit to vary at a first speed along the sinusoidal curve trajectory. Based on the height of the display unit out of the vertical movement range, the controller can control the height of the display unit to move to a boundary of the vertical movement range at a second speed faster than the first speed and then vary at the first speed along the sinusoidal curve trajectory.

The controller can control the posture adjustment driving unit to maintain the height of the display unit at a random height within the vertical movement range.

The controller can control the posture adjustment driving unit to update the random height within the vertical movement range after maintaining the height of the display unit at the random height for one period and maintain the height of the display unit at the updated random height for a next period.

Based on detecting an absence of the user from the user image, the controller can control the posture adjustment driving unit to maintain the posture of the display unit at a time point of detecting the absence.

Based on continuously detecting the absence for a prescribed time from the time point of detecting the absence, the controller can control the posture adjustment driving unit to adjust the posture of the display unit according to the user preference setting.

Based on detecting a presence of the user in front of the display unit, the controller can control a posture adjustment of the display unit to be initiated.

The controller can control a posture adjustment of the display unit to be performed in further consideration of a user posture mode.

The user posture mode can include a watch mode and a non-watch mode. Based on the user posture mode corresponding to the watch mode, the controller can control the posture adjustment driving unit to enable the posture of the display unit to follow the user posture. Based on the user posture mode corresponding to the non-watch mode, the controller can control the posture adjustment driving unit to enable the posture of the display unit not to follow the user posture.

The controller can obtain body skeleton information of the user from the first user image and controls a gaze of the user to obtain a gaze point crossing with the display panel based on the body skeleton information. Based on whether the gaze point exists in the display panel, the controller can distinguish the watch mode and the non-watch mode.

The controller can determine the first user posture based on a spaced distance between the camera and the user calculated based on a feature point pixel distance between two feature points of a user face in the first user image.

The controller can be configured to obtain a second user image using the user taking the user basic posture as a subject at a first height of the display unit through the camera, obtain a third user image using the user taking the user basic posture as the subject at a second height of the display unit through the camera, calculate a reference pixel distance between two feature points of a face of the user from the second user image or the third user image, and calculate the spaced distance between the camera and the user in the first user image further based on the reference spaced distance and the reference pixel distance.

The controller can calculate a user-optimized display unit posture setting based on a 3D body mesh of the user generated using the second user image and the third user image.

Based on correcting the user-optimized display unit posture setting by the user, the controller can store the corrected posture setting as a user preference setting. Based on not correcting the user-optimized display unit posture setting by the user, the controller can store the user-optimized display unit posture setting as the user preference setting.

In further technical aspect of the present disclosure, provided is a method of controlling a display device, the method including photographing a user image through a camera and adjusting a posture of a display unit within a vertical movement range of the display unit determined based on a user posture in the user image.

Effects of a display device and control method thereof according to the present disclosure will be described below.

According to at least one of various aspects of the present disclosure, there is an advantage that a posture of a display unit can be automatically adjusted depending on a user's posture.

Effects obtainable from the present disclosure can be non-limited by the above-mentioned effects. Also, other unmentioned effects can be clearly understood from the following description by those having ordinary skill in the technical field to which the present disclosure pertains.

BRIEF DESCRIPTION OF THE DRAWINGS

The present invention will become more fully understood from the detailed description given herein below and the accompanying drawings, which are given by illustration only, and thus are not limitative of the present invention.

FIG. 15 is a diagram to describe a recognition of a user's 2D face landmark according to an embodiment of the present disclosure.

FIG. 17 is a diagram to describe recognition of user's 3D body skeleton according to an embodiment of the present disclosure.

FIG. 18 illustrates an example of user's posture information obtainable from the 3D body skeleton of FIG. 17.

DETAILED DESCRIPTION OF THE DISCLOSURE

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present. A singular representation may include a plural representation unless it represents a definitely different meaning from the context. In this disclosure, the expression "at least one of A or B" may mean "A", "B", or "A and B".

Terms such as "include" or "has" are used herein and should be understood that they are intended to indicate an existence of several components, functions or steps, disclosed in the specification, and it is also understood that greater or fewer components, functions, or steps may likewise be utilized.

Display devices described herein may include monitors, mobile phones, smartphones, laptop computers, digital broadcasting terminals, Personal Digital Assistants (PDA), Portable Multimedia Players (PMPs), navigation systems, slate PCs, tablet PCs, ultra-books, digital TVs, and the like.

Figure 1:
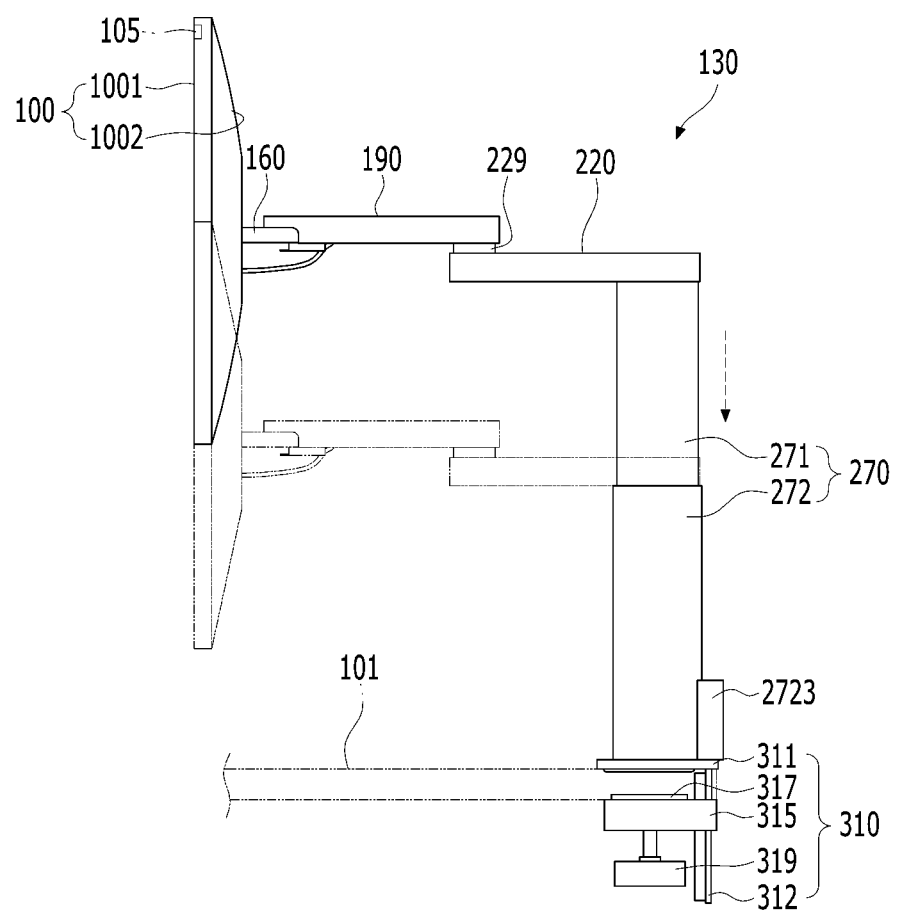
FIG. 1 is a lateral view of a display device in accordance with one implementation of the present disclosure.
Figure 2:
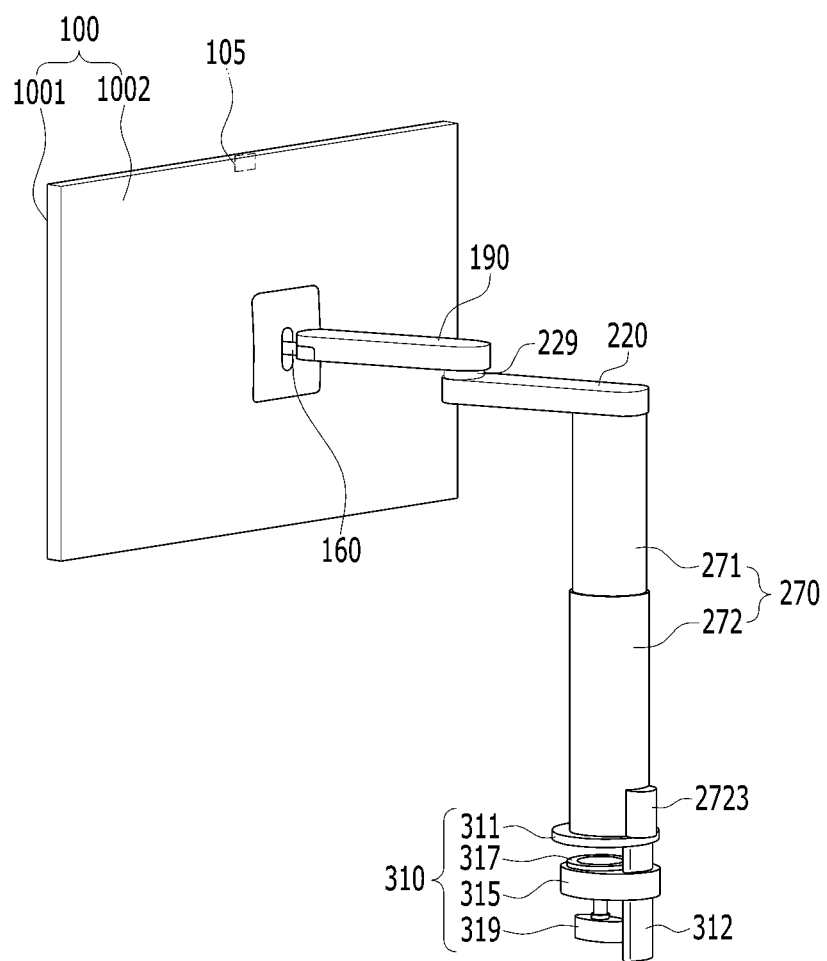
FIG. 2 is a rear perspective view of the display device of FIG. 1 according to an embodiment of the present disclosure.

FIG. 1 is a lateral view of a display device in accordance with one implementation of the present disclosure, and FIG. 2 is a perspective view of the display device of FIG. 1. As illustrated in FIGS. 1 and 2, a display device according to an implementation of the present disclosure can include a display unit 100, a mounting bracket 140, a first arm 160, a second arm 190, a third arm 220, a pillar 270, and a fixing unit 310.

The display unit 100 can have a screen disposed on its front surface to display images. The display unit 100 can include, for example, a display panel 1001 defining the screen, and a cover 1002 surrounding and supporting the display panel 1001.

The display device according to the implementation can include the display unit 100, and a support device 130 coupled to a rear surface of the display unit 100 to support the display unit 100 such that tilting angle, height, and distance of the display unit 100 are adjusted.

The support device 130 can include a mounting bracket 140, a first arm 160, a second arm 190, a third arm 220, a pillar 270, and a fixing unit 310. The mounting bracket 140, the first arm 160, the second arm 190, the third arm 220, the pillar 270, and the fixing unit 310 can be coupled to the rear surface of the display unit 100 to be movable relatively.

Accordingly, since the display unit 100 has a relatively high degree of freedom (more than 5 degrees of freedom), the height, back and forth distance, and vertical tilting angle of the screen of the display unit 100 with respect to the user's eyes can be adjusted, so that an appropriate viewing angle can be easily secured. The mounting bracket 140 can be fixedly coupled to the rear surface of the display unit 100, and a front end portion of the first arm 160 can be coupled to be vertically tilted centering on a shaft (tilting shaft) 1603 that is horizontally disposed on the mounting bracket 140.

A front end portion of the second arm 190 can be coupled to a rear end portion of the first arm 160 to be relatively pivotable centering on a shaft that is arranged vertically. A front end portion of the third arm 220 can be coupled to a rear end portion of the second arm 190 to be relatively pivotable centering on a shaft that is arranged vertically. A rear end portion of the third arm 220 can be coupled to the pillar 270 to be movable up and down. The pillar 270 can be coupled to the fixing unit 310 to be relatively pivotable centering on a shaft that is arranged vertically.

The fixing unit 310 can be fixed to a fixing object 101 (e.g., a top plate of a desk or table). The fixing unit 310 can be coupled to an edge of the fixing object 101. The implementation disclosed herein illustrates an example in which the fixing object 101 is formed in a rectangular plate shape and the fixing unit 310 is coupled to a center of a rear side part of the fixing object 101.

In this embodiment, the fixing unit 310 does not have to have a structure coupled to a rear side portion of the fixing object 101. For example, the fixing unit 310 may be configured to have a pedestal structure that can be placed on a top upper plate of the fixing object 101.

The display unit 100 can be formed, for example, in a rectangular parallelepiped shape having two long side portions 1003 and two short side portions 1004. In general, the display unit 100 can be arranged to have a long length in left and right directions. The two long side portions 1003 of the display unit 100 can be arranged in a horizontal direction and the two short side portions 1004 can be arranged in a vertical (perpendicular) direction.

When the screen of the display unit 100 faces forward, the long side portions 1003 can be arranged in the left and right direction and the short side portions 1004 can be arranged in the vertical direction. In the implementation disclosed herein, when the screen of the display unit 100 is disposed to face forward, a thickness direction of the display unit 100 can be referred to as a back and forth direction.

In the implementation, the display unit 100 can be configured to pivot between a first position at which the two long side portions 1003 are horizontally arranged and a second position at which the two long side portions 1003 are vertically disposed, about the first arm 160 coupled to the rear surface. A camera 105 for capturing a user can be provided on a front surface of the display unit 100. The camera 105 can be disposed, for example, on a central area of an upper edge (long side portion 1003) (for example, upper side bezel) of the screen of the display unit 100.

Figure 3:
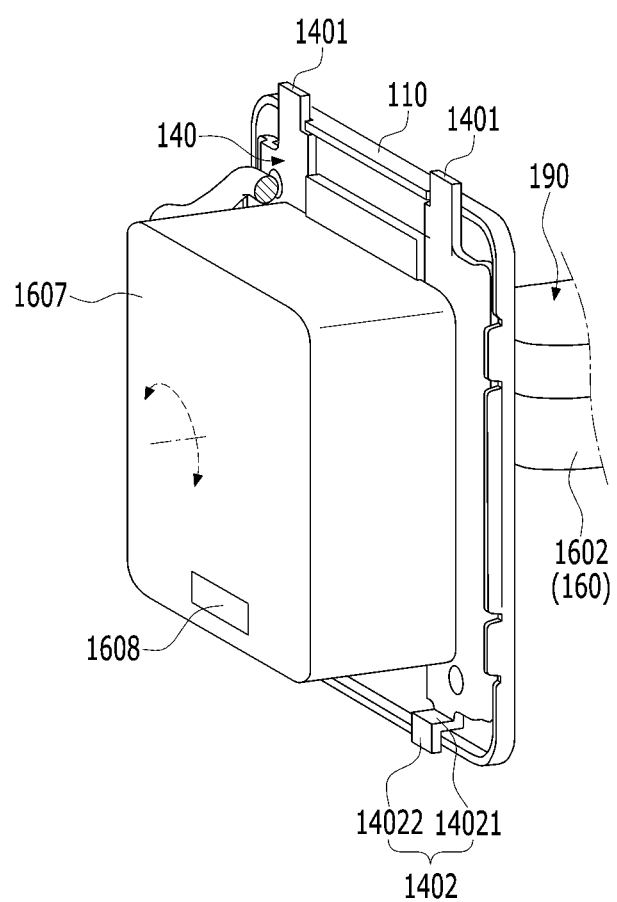
FIG. 3 is an external perspective view illustrating a coupling area between a first arm and a display unit of FIG. 1 according to an embodiment of the present disclosure.
Figure 4:
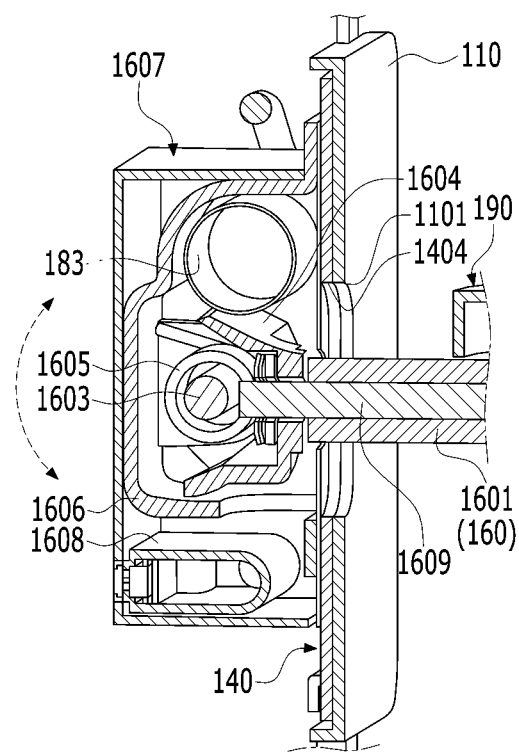
FIG. 4 is a cross-sectional view of FIG. 3 according to an embodiment of the present disclosure.
Figure 5:
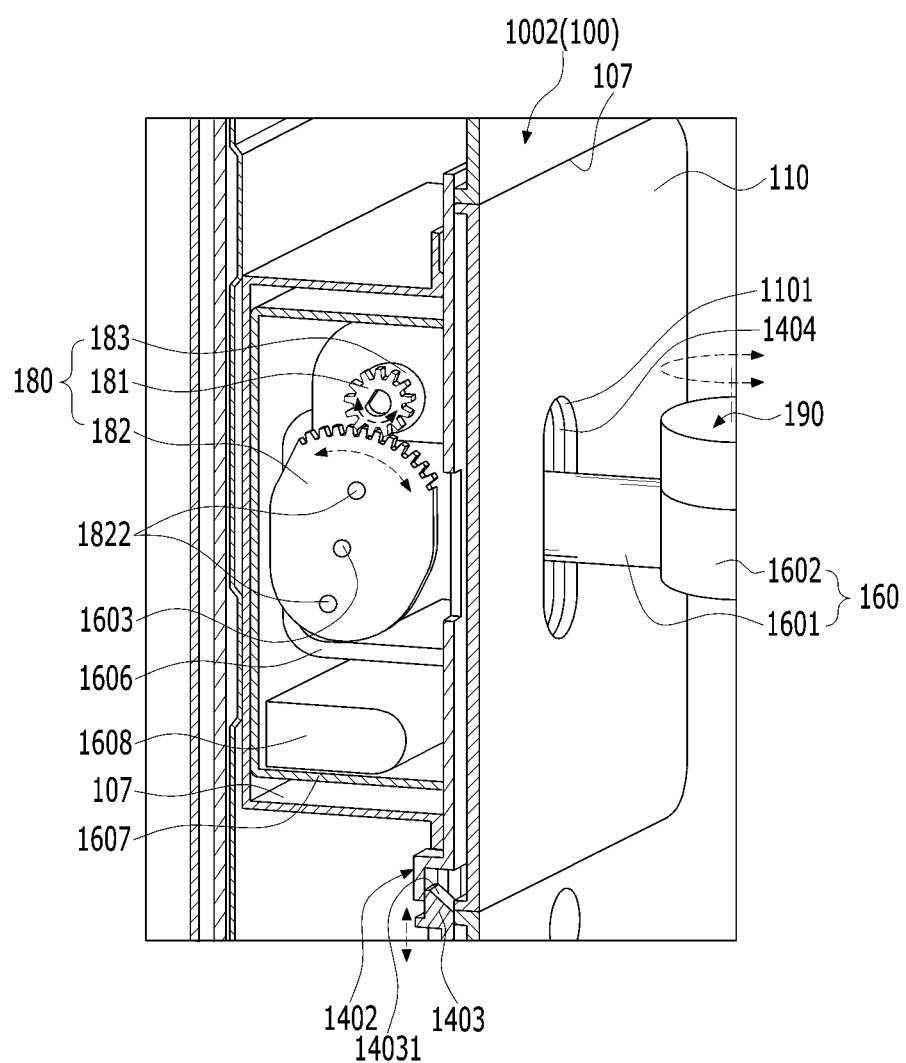
FIG. 5 is a view illustrating a driving gear and a driven gear of FIG. 3 according to an embodiment of the present disclosure.

In this instance, the camera 105 can be placed on the display unit 100 such that an optical axis of the camera 105 is inclined downward by a prescribed angle with respect to a normal of the display unit 100. A recessed portion 107 (as shown in FIG. 5) can be in the rear surface of the display unit 100, and a recessed portion cover 110 (as shown in FIGS. 3-5) can be disposed on the recessed portion 107 to close an opening of the recessed portion 107. One side (front end portion) of the first arm 160 can be coupled through the recessed portion cover 110.

FIG. 3 is an external perspective view illustrating a coupling area between the first arm and the display unit 110a of FIG. 1, FIG. 4 is a cross-sectional view of FIG. 3, and FIG. 5 is a view illustrating a driving gear and a driven gear of FIG. 3. As illustrated in FIGS. 3 to 5, the mounting bracket 140 can be provided on an inner side of the recessed portion cover 110.

The mounting bracket 140 can have a substantially rectangular plate shape. The recessed portion cover 110 can be implemented in a rectangular plate shape with a size sufficient to cover the exterior of the mounting bracket 140. In the implementation, the display unit 100 and the mounting bracket 140 can be coupled to each other in a snap-fit manner.

Specifically, an upper coupling protrusion 1401 can protrude upwardly from an upper side of the mounting bracket 140. An upper coupling protrusion groove in which the upper coupling protrusion 1401 is inserted can be formed in an upper side of the recessed portion 107 of the display unit 100.

An elastic protrusion 1403 that elastically protrudes and retracts can protrude from a lower side of the recessed portion 107 to be disposed at the front of the elastic protrusion 1403. The elastic protrusion 1403 can be disposed at the rear of the lower coupling protrusion 1402 to suppress a rearward separation of the lower coupling protrusion 1402.

The lower coupling protrusion 1402 can include a horizontal section 14021 protruding forward from a lower end of the mounting bracket 140, and a vertical section 14022 bent downward from the horizontal section 14021. The elastic protrusion 1403 can be disposed below the horizontal section 14021 of the lower coupling protrusion 1402 and behind the vertical section 14022.

In addition, an elastic protrusion spring can be provided at one side of (below) the elastic protrusion 1403 to apply an elastic force so that the elastic protrusion 1403 protrudes upward. A guide tilted surface 14031 can be formed on an outer surface (rear surface) of the elastic protrusion 1403 to be tilted in a moving direction of the elastic protrusion 1403. The elastic protrusion 1403 can be pushed down when the guide tilted surface 14031 is pressed. When the pressing force is released, the elastic protrusion 1403 can be restored to an initial position, at which it upwardly protrudes, by an elastic force of the elastic protrusion spring.

With the configuration, the mounting bracket 140 can be coupled in a downwardly tilted state to the rear side so that an end portion of the upper coupling protrusion 1401 can be inserted into the upper coupling protrusion groove. A lower side portion of the mounting bracket 140 can rotate downward such that the lower coupling protrusion 1402 is brought into contact with the guide tilted surface 14031 of the elastic protrusion 1403. The vertical section 14022 of the lower coupling protrusion 1402 can thus press the elastic protrusion 1403. When the lower end portion of the vertical section 14022 of the lower coupling protrusion 1402 presses the guide tilted surface 14031, the elastic protrusion 1403 can move downward.

When the vertical section 14022 of the lower coupling protrusion 1402 passes the elastic protrusion 1403, the mounting bracket 140 can be brought into contact with the rear surface of the display unit 100. When a pressing force applied to the elastic protrusion 1403 is released after the vertical section 14022 of the lower coupling protrusion 1402 passes the elastic protrusion 1403, the elastic protrusion 1403 can protrude upward and return to its initial position. At this time, the elastic protrusion 1403 can be located below the horizontal section 14021 of the lower coupling protrusion 1402 and behind the vertical section 14022, so that the mounting bracket 140 can be suppressed from being unexpectedly separated from the display unit 100.

Accommodation holes 1101 and 1404 can be formed through recessed portion cover 110 and the mounting bracket 140, respectively. Accordingly, the first arm 160 can be accommodated in the accommodation holes 1101 and 1404 to be relatively movable. Each of the accommodation holes 1101 and 1404 can be formed to have a long length vertically to correspond to a relative movement trajectory of the first arm 160 when the display unit 100 is tilted up and down.

In the implementation, the first arm 160 can include, for example, a first arm body 1601, and a second arm connecting portion 1602 formed on one end portion (rear end portion) of the first arm body 1601 to be connected to the second arm 190. The first arm body 1601 can have, for example, a rod shape. The second arm connecting portion 1602 can be expanded compared to the first arm body 1601 to correspond to the size of the second arm 190, for example.

As illustrated in FIG. 4, a tilting shaft 1603 can be provided on the front end portion of the first arm 160. The tilting shaft 1603 can be disposed to be perpendicular to the first arm 160. The tilting shaft 1603 can be disposed in the horizontal direction.

When the first arm 160 is disposed in the back and forth direction of the fixing object 101, the tilting shaft 1603 can be disposed in the left and right direction of the fixing object 101. The tilting shaft 1603 can be spaced apart from the front end portion of the first arm 160, for example. A pivot shaft 1609 that can pivot with respect to the first arm body 1601 can be provided in the front end portion of the first arm 160.

Accordingly, the display unit 100 can pivot along a plate surface direction about the first arm 160 (the first arm body 1601). The pivot shaft 1609 can protrude to the front of the first arm body 1601. The pivot shaft 1609 can be coupled to the center of the first arm body 1601 to be relatively pivotable.

A tilting shaft support member 1604 for supporting the tilting shaft 1603 can be provided on the front end portion of the first arm 160 (the first arm body 1601). The tilting shaft support member 1604 can have a shape with one side (front) open. The tilting shaft support member 1604 can be coupled to the pivot shaft 1609. Accordingly, the tilting shaft support member 1604 can pivot about the pivot shaft 1609.

The pivot shaft 1609 can be configured, for example, to pivot between a first position at which the long side portion 1003 of the display unit 100 is horizontally disposed and a second position at which the long side portion 1003 of the display unit 100 is vertically disposed. The tilting shaft 1603 can be supported by the tilting shaft support member 1604 while being spaced apart from the pivot shaft 1609.

An elastic member 1605 can be provided between the tilting shaft 1603 and the tilting shaft support member 1604. When the display unit 100 rotates downward, the elastic member 1605 can be compressed to accumulate elastic force. The elastic member 1605 can be implemented as, for example, a torsion coil spring.

Accordingly, when the display unit 100 rotates upward, the display unit 100 can easily rotate upward by virtue of the elastic force accumulated in the elastic member 1605. In addition, driving force required for the upward rotation of the display unit 100 can be reduced. The tilting shaft 1603 can be provided with a tilting member 1606 that can be tilted up and down about the tilting shaft 1603.

The tilting member 1606 can rotate upward and downward centering on the tilting shaft 1603. The tilting member 1606 can have an inner accommodation space. The tilting member 1606 can have an open rear end portion. A front end portion of the tilting member 1606 can be coupled to the rear surface of the mounting bracket 140 in a contacting manner. A tilting case 1607 can be provided outside the tilting member 1606.

The tilting case 1607 can have a larger size than the tilting member 1606 so that the tilting member 1606 can be accommodated therein. The tilting case 1607 can accommodate the recessed portion 107 of the display unit 100. The tilting case 1607 can be implemented, for example, in a rectangular parallelepiped shape in which an accommodation space opened rearward is defined.

A rear end portion of the tilting case 1607 can be coupled to the mounting bracket 140. A connector 1608 can be provided inside the tilting case 1607. The connector 1608 can be disposed below the tilting member 1606 inside the tilting case 1607. The connector 1608 can be connected to another connector that is provided in the recessed portion 107 of the display unit 100 when the tilting case 1607 is inserted into the recessed portion 107 of the display unit 100.

Accordingly, the display unit 100 can be electrically connected to another electronic device. More specifically, the display device according to the implementation can be configured as a monitor (display) of a personal computer, and the electronic device can be configured as a main body of the personal computer. As the connector 1608 is connected, the display device can be electrically connected to the main body of the personal computer to perform communication with the personal computer.

Meanwhile, a tilting driving unit 180 can be disposed at the tilting member 1606 and the first arm 160 to allow the tilting member 1606 to be tilted up and down based on the tilting shaft 1603. The tilting driving unit 180 can include a driving gear 181 disposed on any one of the tilting member 1606 and the first arm 160, a driven gear 182 disposed on another one of the tilting member 1606 and the first arm 160 to be engaged with the driving gear 181, and a tilting driving motor 183 rotating the driving gear 181.

The tilting member 1606 can be provided with the tilting driving motor 183. The tilting driving motor 183 can be disposed at an upper side of the tilting shaft support member 1604 inside the tilting member 1606. The tilting driving motor 183 can have a rotating shaft that is disposed parallel to the tilting shaft 1603.

The driving gear 181 can be provided on the rotating shaft of the tilting driving motor 183. The driving gear 181 can be, for example, implemented as a spur gear having a tooth portion protruding from a circumference in a radial direction. The driven gear 182 can be provided on the tilting shaft 1603, for example.

As illustrated in FIG. 5, the driven gear 182 can be implemented as a sector gear that is formed on an arcuate portion spaced apart from the tilting shaft 1603 by a preset distance and forms a preset internal angle between both ends. The driven gear 182 can be configured to be fixedly supported by, for example, the tilting shaft 1603 and the tilting shaft support member 1604.

A plurality of protrusions 1822 protruding from the tilting shaft 1603 and the tilting shaft support member 1604 can be inserted into the driven gear 182. In the implementation, a tooth portion of the driven gear 182 can be disposed above the tilting shaft 1603, and the driving gear 181 can be provided in an upper portion of the tilting member 1606 to be engaged with the tooth portion of the driven gear 182.

The driving gear 181 can be coupled to be disposed at the center of the tooth portion of the driven gear 182 when the screen of the display unit 100 is disposed in the up and down (vertical) direction. Accordingly, the driving gear 181 can move up and down along the driven gear 182.

With the configuration, when the driving gear 181 rotates in a clockwise direction in the drawing, the driving gear 181 can move downward in the clockwise direction along the tooth portion of the driven gear 182, and the tilting member 1606 can rotate upward centering on the tilting shaft 1603, so that the screen of the display unit 100 faces upward. On the other hand, when the driving gear 181 rotates in a counterclockwise direction in the drawing, the driving gear 181 can move upward along the tooth portion of the driven gear 182, and the tilting member 1606 can rotate downward centering on the tilting shaft 1603, so that the screen of the display unit 100 faces downward.

Figure 6:
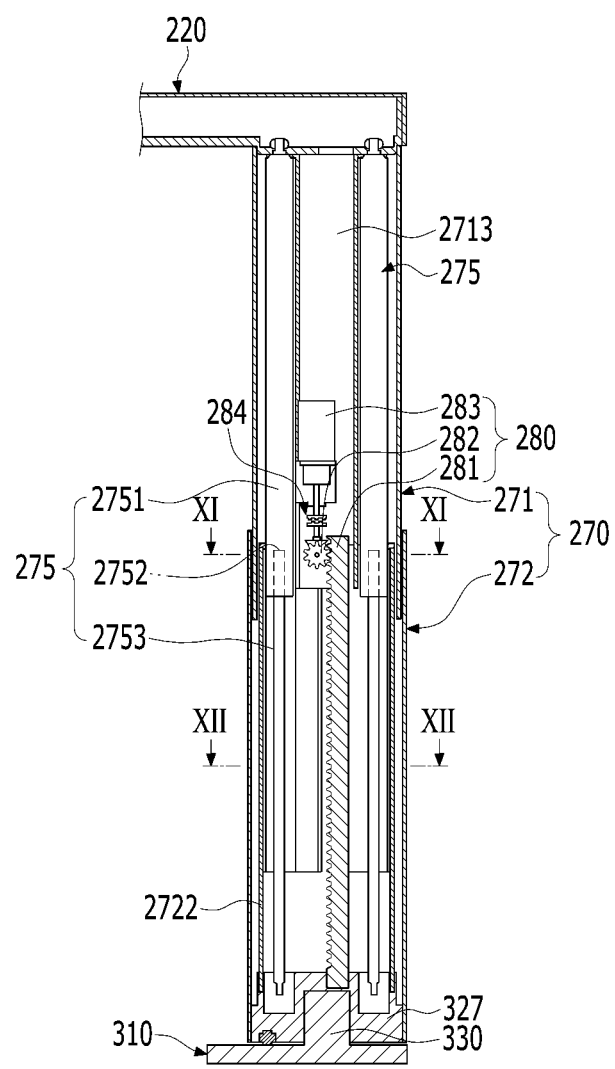
FIG. 6 is a cross-sectional view illustrating the inside of a pillar of FIG. 1 according to an embodiment of the present disclosure.
Figure 7:
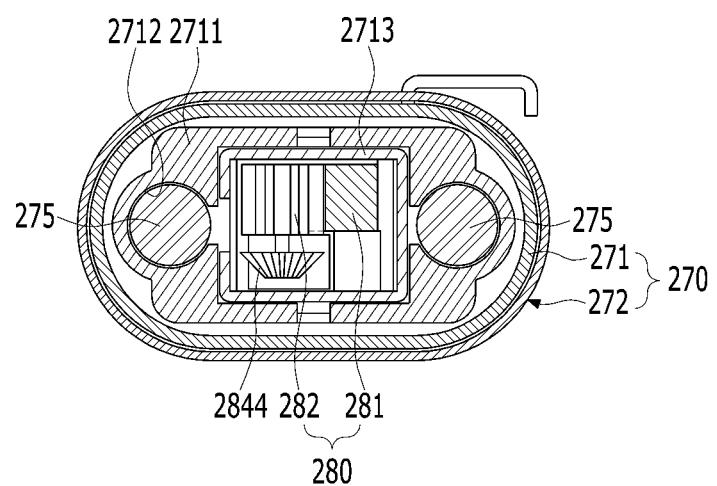
FIG. 7 is a cross-sectional view illustrating an upper pillar of FIG. 6 according to an embodiment of the present disclosure.
Figure 8:
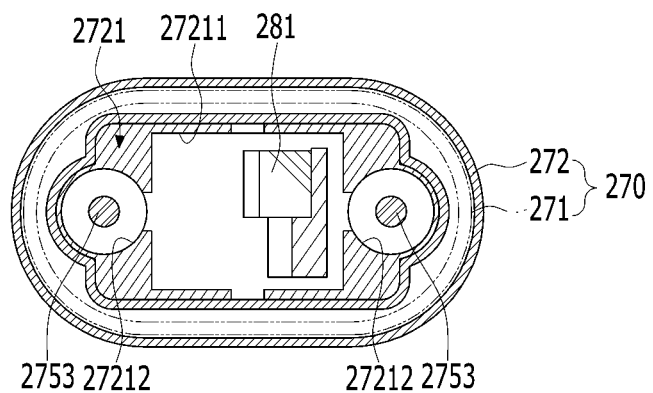
FIG. 8 is a cross-sectional view illustrating a lower pillar of FIG. 6 according to an embodiment of the present disclosure.
Figure 9:
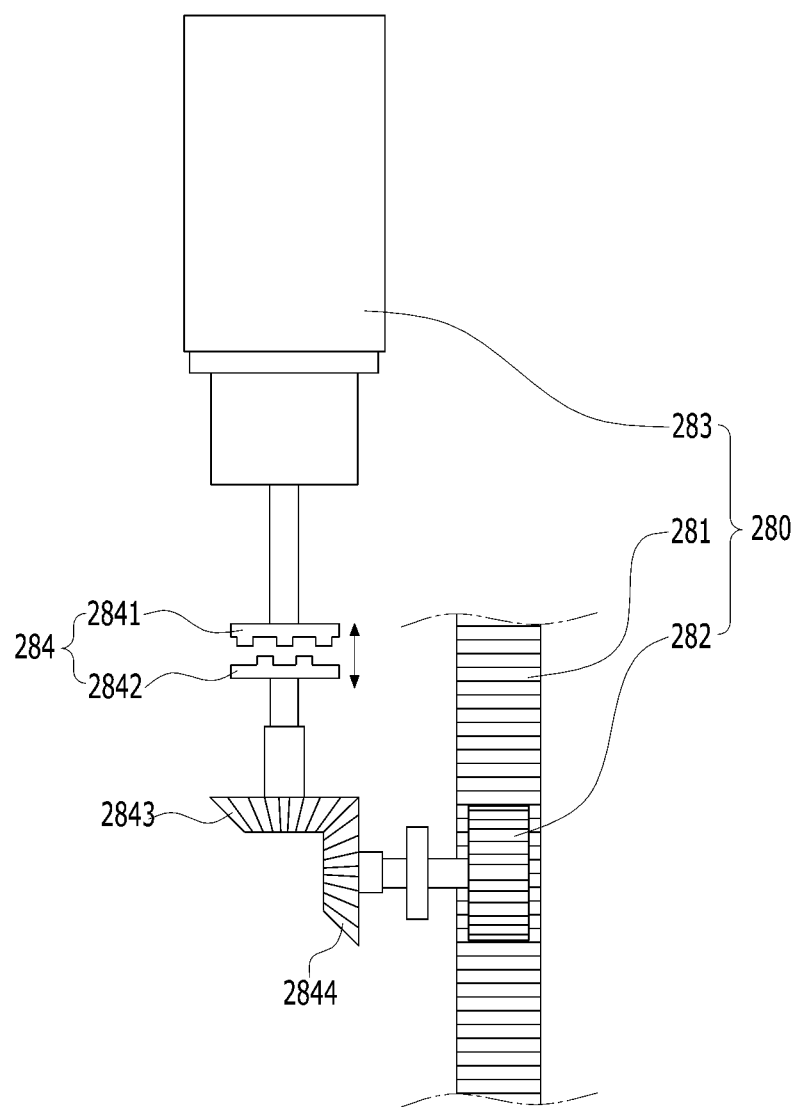
FIG. 9 is a schematic view illustrating a structure of a clutch of FIG. 7 according to an embodiment of the present disclosure.

FIG. 6 is a cross-sectional view illustrating an inside of a pillar of FIG. 1, FIG. 7 is a cross-sectional view illustrating an upper pillar of FIG. 6, FIG. 8 is a cross-sectional view illustrating a lower pillar of FIG. 6, and FIG. 9 is a schematic view illustrating a structure of a clutch of FIG. 7. As illustrated in FIG. 6, the pillar 270 can include a lower pillar 272 connected to the fixing unit 310, and an upper pillar 271 disposed to be movable up and down with respect to the lower pillar 272.

The third arm 220 can be provided on the upper pillar 271. The third arm 220 can be provided on an upper end of the upper pillar 271. In the implementation, the rear end portion of the third arm 220 can be coupled to the upper end of the upper pillar 271. Accordingly, the height of the third arm 220 can be adjusted as the upper pillar 271 moves up and down.

The third arm 220 can be disposed perpendicularly to the pillar 270. The pillar 270 can be arranged in the vertical direction and the third arm 220 can be arranged in the horizontal direction. The pillar 270 can be provided with an elastic member 275 that is compressed when the upper pillar 271 moves down to accumulate elastic force. Accordingly, when the upper pillar 271 moves up, the driving force required for pushing up the upper pillar 271 can be reduced by the elastic force of the elastic member 275.

The elastic member 275 can be implemented as, for example, a gas spring 275. The gas spring 275 can be provided by two disposed side by side with each other. Each of the elastic member 275 (gas spring) can include, for example, a cylinder 2751, a piston 2752 provided in the cylinder 2751, and a piston rod 2753 connected to the piston 2752 and extending to the outside of the cylinder 2751.

In the implementation, one end portion of the elastic member 275 (gas spring) can be fixed to the lower pillar 272 and another end portion of the elastic member 275 (gas spring) can be fixed to the upper pillar 271. More specifically, the cylinder 2751 of the gas spring 275 can be fixed to the upper pillar 271 and the piston rod 2753 can be fixed to the lower pillar 272.

The upper pillar 271 can be, for example, inserted into the lower pillar 272. The upper pillar 271 and the lower pillar 272 each can have an elliptical cross-section. The upper pillar 271 can be slid with its outer surface brought into contact with an inner surface of the lower pillar 272.

As illustrated in FIG. 7, an upper frame 2711 can be provided in the upper pillar 271. The upper frame 2711 can be provided with a gas spring accommodating portion 2712 in which the gas spring 275 is accommodated. An upper guide 2713 can be provided in a center of the upper frame 2711.

The upper guide 2713 can have a substantially rectangular cross-section. The upper guide 2713 can be implemented as a square tube having an inner accommodation space. The upper guide 2713 can be disposed between the gas springs 275.

As illustrated in FIG. 8, a lower frame 2721 can be provided in the lower pillar 272. A lower guide 2722 that is inserted into the upper pillar 271 to guide the upper pillar 271 can be provided outside the lower frame 2721. The lower frame 2721 can be provided in the lower guide 2722.

An upper guide support portion 27211 for slidably supporting the upper guide 2713 can be formed through the lower frame 2721. Gas spring support portions 27212 for slidably supporting the gas springs 275 can be formed through the lower frame 2721. The piston rods 2753 of the gas springs 275 can be accommodated in the gas spring support portions 27212, respectively.

Meanwhile, the pillar 270 can be provided with a height adjusting unit 280 for adjusting the height of the third arm 220. This can result in adjusting the height of the display unit 100. The height adjusting unit 280 can include a rack tooth part 281 provided in the lower pillar 272, a pinion 282 rotating with being engaged with the rack tooth part 281, and a pinion driving motor 283 for rotating the piston 282. The rack tooth part 281 can be disposed in the upper guide support portion 27211.

The rack tooth part 281 can extend into the upper guide 2713. The pinion 282 can be provided in the upper pillar 271. The pinion 282 can be provided on the upper guide 2713. The pinion driving motor 283 for rotating the pinion 282 can be provided in the upper pillar 271.

Meanwhile, a clutch 284 for selectively transmitting rotational force of the pinion driving motor 283 to the pinion 282 can be provided between the pinion driving motor 283 and the pinion 282. Accordingly when power transmission between the pinion driving motor 283 and the pinion 282 is suppressed by the clutch 284, the upper pillar 271 can be manually moved up and down relative to the lower pillar 272.

As illustrated in FIG. 9, the clutch 284 can include, for example, a first clutch 2841 coupled to a rotating shaft of the pinion driving motor 283, and a second clutch 2842 movable toward or away from the first clutch 2841. A first gear 2843 and a second gear 2844 that are engaged with each other at a right angle can be provided at one side of the second clutch 2842. The second clutch 2842 can be movable toward or away from the first gear 2843. The second clutch 2842 can be moved away from the first gear 2843 to be engaged with the first clutch 2841. Accordingly, the rotational force of the pinion driving motor 283 can be transmitted to the pinion 282.

The second gear 2844 and the pinion 282 can be coupled to the same rotating shaft. When the second clutch 2842 is engaged with the first clutch 2841, the rotational force of the pinion driving motor 283 can be transmitted to the pinion 282 sequentially through the first clutch 2841, the second clutch 2842, and the first gear 2843, and the second gear 2844.

When the second clutch 2842 is separated from the first clutch 2841, the pinion driving motor 283 and the pinion 282 can also be separated from each other, and thus the pinion 282 can be free to rotate. With the configuration, when the pinion 282 rotates in one direction (counterclockwise), the pinion 282 can move downward along the rack tooth part 281. Accordingly, the upper pillar 271 and the third arm 220 can move downward. At this time, each of the gas springs 275 can accumulate an elastic force while being compressed.

When the pinion 282 rotates in another direction (clockwise), the pinion 282 can move upward along the rack tooth part 281, and at this time, the upper pillar 271 and the third arm 220 can move upward. In this instance, the upward movement of the upper pillar 271 and the third arm 220 can be facilitated by the accumulated elastic force of each gas spring 275. In addition, an input current of the pinion driving motor 283 can be significantly reduced.

Figure 10:
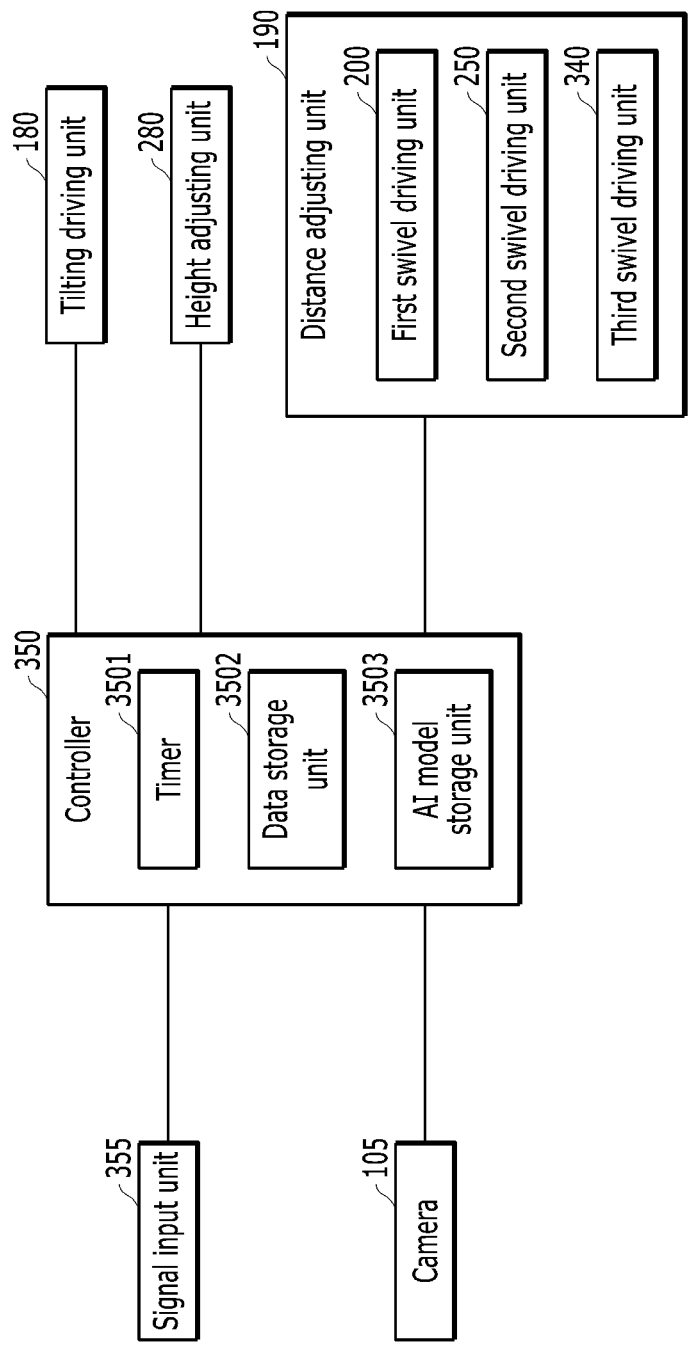
FIG. 10 is a control block diagram of the display device of FIG. 1 according to an embodiment of the present disclosure.

FIG. 10 is a control block diagram of the display device of FIG. 1. As illustrated in FIG. 10, the display device according to the implementation can include a controller 350 implemented as a microprocessor by including a control program. The controller 350 can adjust tilting angle, height, and distance of the display unit 100, respectively.

The controller 350 can include a signal input unit 355 for inputting an operation signal. The signal input unit 355 can be configured to input a signal in a pressing and/or touching manner, for example. A camera 105 for capturing a user's posture can be connected to the controller 350 to perform communication. The camera 105 can be disposed on the front surface of the display unit 100.

The controller 350 can be connected to the tilting driving unit 180 to adjust the tilting angle of the display unit 100. The controller 350 can be connected to the height adjusting unit 280 to adjust the height of the display unit 100. The controller 350 can be connected to a distance adjusting unit to adjust the distance of the display unit 100.

The distance adjusting unit 190 can include, for example, the first swivel driving unit 200 and the second swivel driving unit 250. The distance adjusting unit 190 can include, for example, the second swivel driving unit 250 and the third swivel driving unit 340. The distance adjusting unit 190 can include, for example, the first swivel driving unit 200, the second swivel driving unit 250, and the third swivel driving unit 340.

The controller 350 can include, for example, the second swivel driving unit 250 and the third swivel driving unit 340. The controller 350 can recognize user's basic posture and changed posture captured by the camera 105 and adjust a direction of the display unit to the user's viewing angle by controlling each of at least one of the tilting driving unit 180, the height adjusting unit 280, the first swivel driving unit 200, the second swivel driving unit 250, and the third swivel driving unit 340.

At least one of the tilting driving unit 180, the height adjusting unit 280, and the distance adjusting unit 190 may be collectively referred to as a "position adjusting driving unit." For example, when the user maintains the basic posture for a preset time or longer, the controller 350 can induce the change in the user's posture by actively adjusting viewing angles of the user and the display unit 100.

When the user's posture is changed from the basic posture and the preset time elapses, the controller 350 can notify that the posture has changed through the display unit 100. When the user's posture changes from the basic posture and the preset time elapses, the controller 350 can guide posture change information through the display unit 100 and also allow the user to perform a light neck exercise while looking at the display unit 100. More specifically, while the user is looking at the screen of the display unit 100, when the user rotates the display unit 100 up and down, the controller 350 can guide the user to move his or her neck up and down. On the other hand, when the display unit 100 moves to left and right, the controller 350 can guide the user to move his or her neck to left and right.

The controller 350 can include a timer 3501 for counting time. The controller 350 can include a data storage unit 3502 for storing various types of information including information related to the user's basic posture and changed postures.

Hereinafter, Artificial Intelligence (AI) that may be used in the present disclosure will be described. Artificial Intelligence (AI) refers to a field that studies artificial intelligence or methodology capable of achieving artificial intelligence. Machine learning refers to a field that defines various problems handled in the AI field and studies methodology for solving the problems. Machine learning may also be defined as an algorithm for raising performance for any task through steady experience of the task.

An artificial neural network (ANN) may refer to a model in general having problem solving capabilities, that is composed of artificial neurons (nodes) constituting a network by a combination of synapses, as a model used in machine learning. The ANN may be defined by a connection pattern between neurons of different layers, a learning process of updating model parameters, and/or an activation function for generating an output value.

The ANN may include an input layer, an output layer, and, optionally, one or more hidden layers. Each layer includes one or more neurons and the ANN may include a synapse connecting neurons. In the ANN, each neuron may output input signals, which are input through the synapse, weights, and function values of an activation function for deflection.

A model parameter refers to a parameter determined through learning and includes a weight of synaptic connection and a deflection of a neuron. A hyperparameter refers to a parameter that should be configured before learning in a machine learning algorithm and includes a learning rate, the number of repetitions, a mini batch size, an initialization function, and the like.

The purpose of learning of the ANN may be understood as determining the model parameter that minimizes a loss function. The loss function may be used as an index to determine an optimal model parameter in a learning process of the ANN. Machine learning may be classified into supervised learning, unsupervised learning, and reinforcement learning, according to a learning scheme.

Supervised learning refers to a method of training the ANN in a state in which a label for training data is given. The label may represent a correct answer (or result value) that the ANN should infer when the training data is input to the ANN. Unsupervised learning may refer to a method of training the ANN in a state in which the label for the training data is not given. Reinforcement learning may refer to a learning method in which an agent defined in a certain environment is trained to select a behavior or a behavior order that maximizes accumulative compensation in each state.

Among ANNs, machine learning implemented as a deep neural network (DNN) including a plurality of hidden layers is also called deep learning. Deep learning is a part of machine learning. Hereinbelow, machine learning includes deep learning.

An object detection model using machine learning includes a you only look once (YOLO) model of a single-step scheme, a faster regions with convolution neural networks (R-CNN) model of a two-step scheme, and the like. The YOLO model is a model in which an object existing in an image and a position of the corresponding object may be predicted as the image is viewed only once.

The YOLO model divides the original image into grids of the same size. Then, for each grid, the number of bounding boxes specified in a predefined form around a center of the grid is predicted, and reliability is calculated based on the predicted number. Thereafter, whether the image contains the object or contains only a background may be included, and a location with high object reliability may be selected, so that an object category may be identified.

The faster regions with convolution neural networks R-CNN model is a model that may detect the object faster than an R-CNN model and a Fast R-CNN model. The faster regions with convolution neural networks R-CNN model will be described in detail.

First, a feature map is extracted from the image via an R-CNN model. Based on the extracted feature map, a plurality of regions of interest (RoIs) are extracted. RoI pooling is performed for each region of interest. The RoI pooling is a process of setting grids of a feature map to which the regions of interest are projected to fit a H×W size that is determined in advance and extracting the greatest value for each cell included in each grid to extract a feature map having the H×W size. A feature vector may be extracted from the feature map having the H×W size, and identification information of the object may be obtained from the feature vector.

The artificial intelligence model stored in an artificial intelligence model storage unit 3503 may be trained by a separate AI server and downloaded from the AI server into the artificial intelligence model storage unit 3503. An AI server for training the artificial intelligence model will be described with reference to FIG. 11. In particular, FIG. 11 illustrates an AI server according to an embodiment of the present disclosure.

Figure 11:
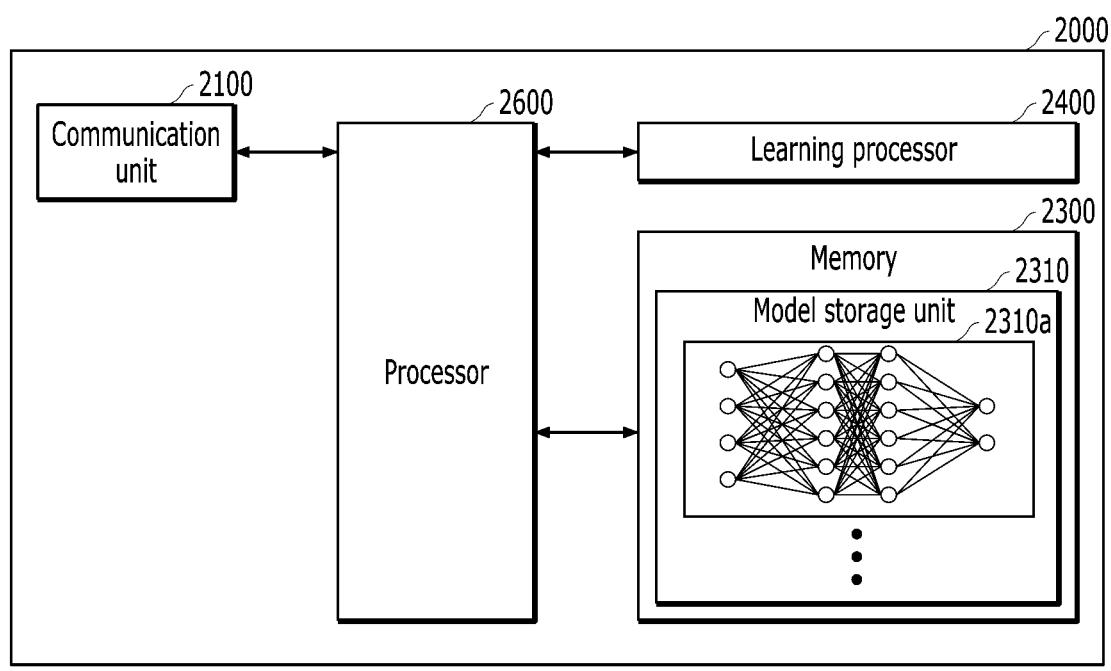
FIG. 11 illustrates an AI server according to an embodiment of the present disclosure.

Referring to FIG. 11, an AI server 2000 can refer to a device that trains artificial neural networks using a machine learning algorithm or uses the trained artificial neural network. Here, the AI server 2000 may include a plurality of servers to perform distributed processing or may be defined as a 5G network. In this instance, the AI server 2000 may be included as a part of a display device and may perform at least one portion of AI processing together.

The AI server 2000 may include a memory 2300, a learning processor 2400, a processor 2600, and the like. A communication unit 2100 may transmit and receive data to and from an external device such as the display device. The memory 2300 may include a model storage unit 2310. The model storage unit 2310 may store an artificial intelligence model (or artificial neural networks) 2310a that is being trained or has been trained through the learning processor 2400.

The learning processor 2400 may train the artificial neural networks 2310a using learning data. A learning model may be used while being loaded on the AI server 2000 of the artificial neural networks, or may be used by being loaded on an external device such as the display device.

The learning model may be implemented in hardware, software, or a combination of hardware and software. When some or all of the learning model is implemented in software, one or more instructions constituting the learning model may be stored in the memory 2300. The processor 2600 may infer a result value for new input data using the learning model and generate a response or control command based on the inferred result value.

Figure 12:
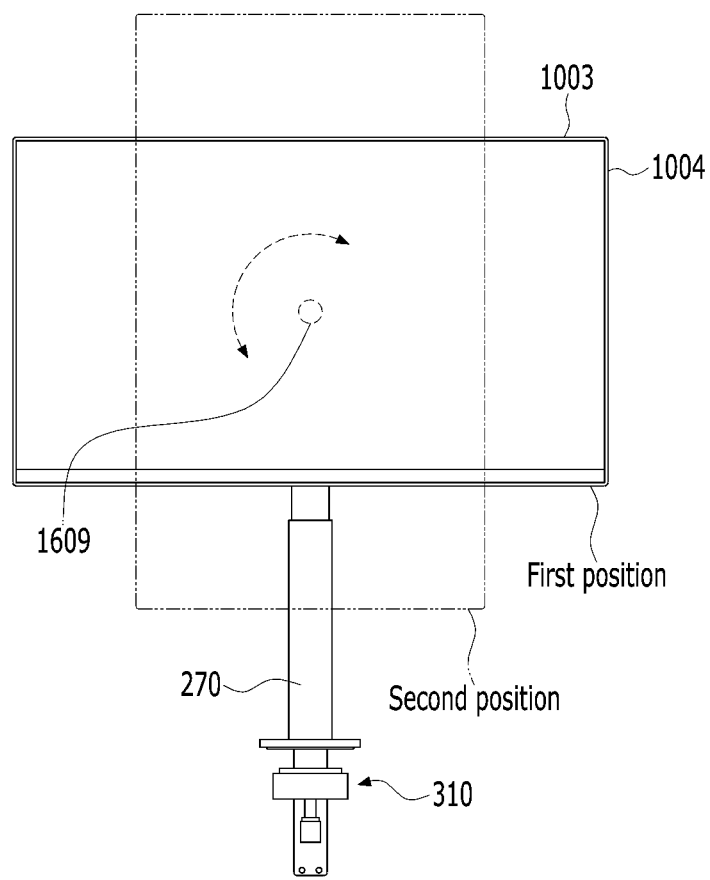
FIG. 12 is a diagram illustrating a state in which the display unit of FIG. 2 is pivoted in a vertical direction.

FIG. 12 is a diagram illustrating a state in which the display unit of FIG. 2 is pivoted in a vertical direction. As illustrated in FIG. 12, the display device of the present embodiment may be rotated between a first position where a long side part 1003 of the display unit 100 is horizontally disposed and a second position where the long side part 1003 is vertically disposed.

When the display unit 100 is to be rotated to the second position, the display unit 100 may be rotated clockwise. When the display unit 100 is pressed clockwise, the display unit 100 is rotated around a pivot shaft 1609. In this instance, the display unit 100 stops at the second position by the stopper 211.

Figure 13:
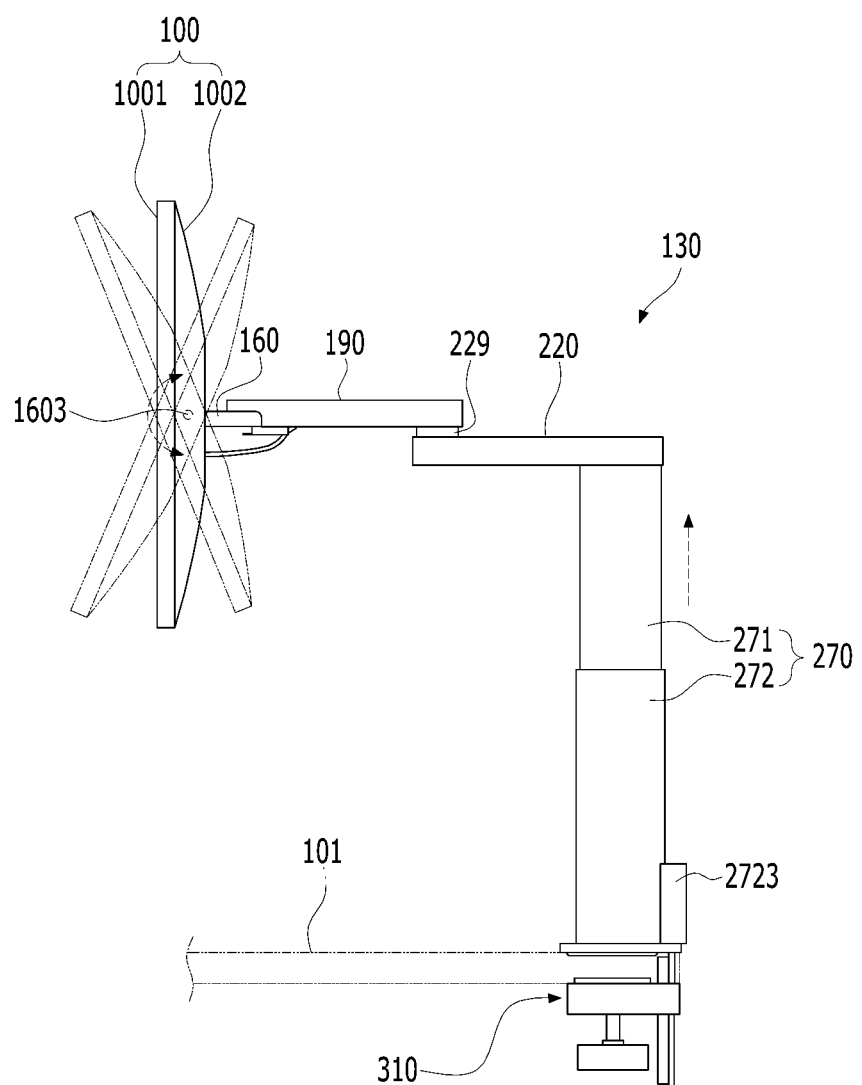
FIG. 13 is a diagram to describe vertical tilting and height adjustment of the display unit of FIG. 2.

FIG. 13 is a diagram to describe vertical tilting and height adjustment of the display unit of FIG. 2. As illustrated in FIG. 12, the controller 350 can control the tilting driving unit 180 to adjust an inclination angle of the screen of the display unit 100.

In the present embodiment, the inclination angle of the screen of the display unit 100 may be adjusted by manual operation. Specifically, when the inclination angle of the screen of the display unit 100 is to be manually adjusted, if an edge of the display unit 100 is held and pressed upward or downward, the display unit 100 is rotated upward or downward around the tilting shaft 1603.

The controller 350 can control the height adjustment unit 280 to adjust the height of the display unit 100. In the present embodiment, the height of the display unit 100 may be achieved by a manual operation. To increase the height of the display unit 100, hold the lower pillar 272 and move the upper pillar 271 or the third arm 220 upward. On the contrary, to decrease the height of the display unit 100, the third arm 220 or the upper pillar 271 may be pressed toward the lower pillar 272.

Figure 14:
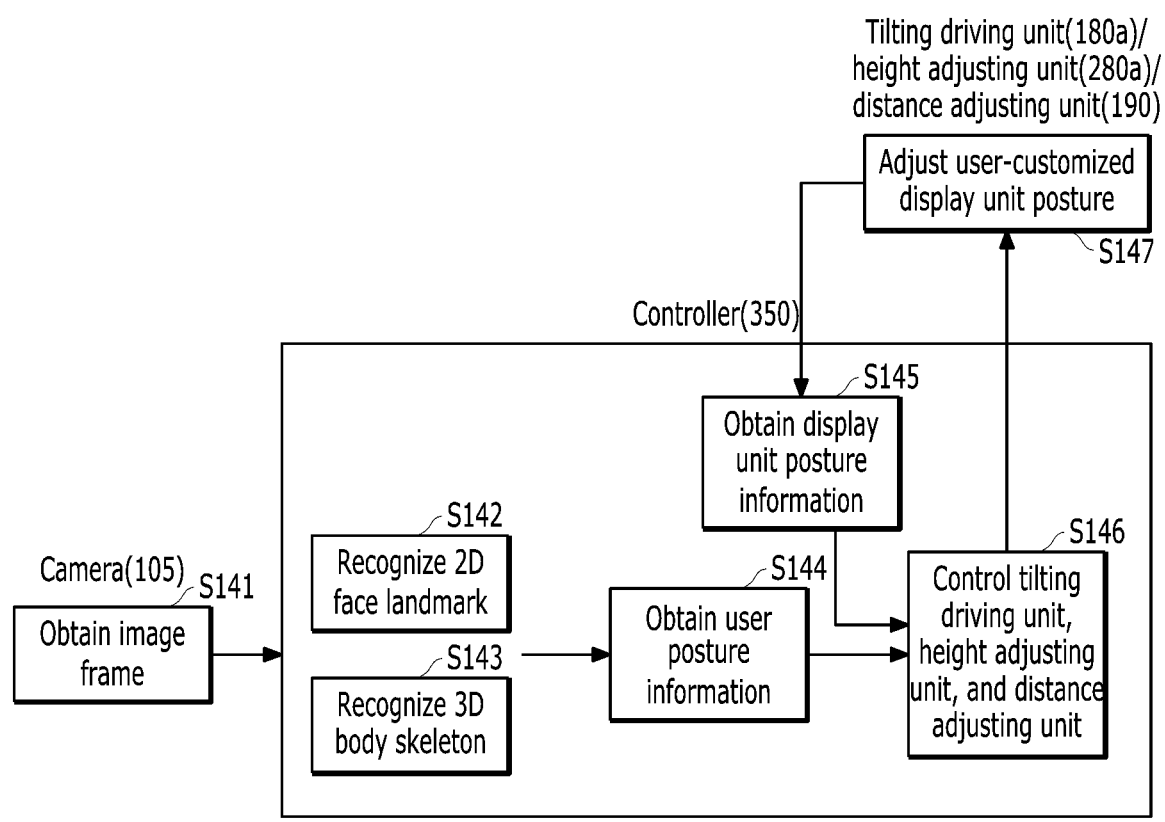
FIG. 14 is a block diagram to describe an operation of a display device according to an embodiment of the present disclosure.

The above-described operation of the display device will be schematically described with further reference to FIG. 14.

In particular, FIG. 14 is a block diagram to describe an operation of the display device according to an embodiment of the present disclosure.

The camera 105 can obtain an image frame (still image or video) of a user positioned in front of the display device to use the display device (S141). The controller 350 can also receive the image frame from the camera 105 and perform a user's two-dimensional (2D) face landmark recognition from the image frame, and perform a user's three-dimensional (3D) body skeleton recognition from the image frame (S143). The face landmark recognition and the body skeleton recognition will be described again later.

The controller 350 can obtain posture information of the user based on the result of the face landmark recognition and the body skeleton recognition (S144). Namely, the controller 350 can detect a change in the user's posture based on the face landmark recognition and the body skeleton recognition.

Further, the user's posture refers to at least one of relative positions and directions of each part of the user's body. The user's posture can further include at least one of a user's position relative to the display unit 100 (e.g., a distance in which the user is spaced apart from the display unit 100, a height of the user's face compared to the display unit 100), and direction.

The controller 350 can control at least one of the tilting driving unit 180, the height adjusting unit 280, and the distance adjusting unit 190 based on the user's posture information and the current posture information of the display unit 100 (S146). That is, at least one of the tilting driving unit 180, the height adjusting unit 280, and the distance adjusting unit 190 can adjust the posture of the display unit 100 to fit the user in order to allow the posture of the display unit 100 to fit the user's posture under the control of the controller 350, that is, to allow the user to view the display unit 100 comfortably (S147). The posture of the display unit 100 means at least one of a tilting angle, a panning angle, a height, and a distance of the display unit 100.

The controller 350 can obtain the adjusted posture information of the display unit 100 (S145). The controller 350 can obtain the adjusted posture information from the tilting driving unit 180, the height adjusting unit 280, and the distance adjusting unit 190, or from control command information for controlling the tilting driving unit 180, the height adjusting unit 280, and the distance adjusting unit 190. As described above, the obtained posture information of the display unit 100 can be used for adjusting the posture of the display unit 100 together with the user's posture information (S146).

Hereinafter, the user's 2D face landmark recognition will be described with reference to FIG. 15. In particular, FIG. 15 is a diagram to describe a recognition of a user's 2D face landmark according to an embodiment of the present disclosure. As illustrated in FIG. 15-1, the controller 350 can recognize a 2D face landmark of the user U from a user image P obtained through the camera 105. The face landmark can mean a face feature point of the user U. In FIG. 15 (15-1), the face landmark is displayed as a plurality of points. The controller 350 can use an artificial intelligence model stored in the artificial intelligence model storage unit 3505 to recognize the 2D face landmark of the user U.

Next, the controller 350 can analyze the 2D face landmark of the user U to determine the number of pixels (or pixel distance) pd in the user image P corresponding to an actual binocular distance PD of the user U as shown in FIG. 15 (15-2). In the present disclosure, the binocular distance can mean a distance between pupils.

If the actual binocular distance PD of the user U is known, a distance D from the camera 105 to the face of the user U can be calculated through the user image P (i.e., only one image frame in which the face landmark can be derived) based on the equation shown in FIG. 15 (15-3). In the equation, "f" means a focal length. Measuring the actual binocular distance PD of user U will be described later.

When calculating the distance D between the camera 105 and the user U, other body parts or two other feature points (e.g., both ears) can be used. The feature points (both eyes, both ears, etc.) of the user's face used to calculate the distance D between the camera 105 and the user U can be understood as "reference feature points."

The reason why the distance D from the camera 105 to the face of the user U is important for grasping the user's posture will be further described with reference to FIG. 16. In particular, FIG. 16 is a diagram showing a change in an eye level of a user U in a user image P photographed by a camera mounted on a display unit depending on a distance between the user and the display unit according to an embodiment of the present disclosure.

As described above, the camera 105 capable of photographing a user can be provided to a front top end portion of the display unit 100. The camera 105 can be disposed on the display unit 100 such that an optical axis of the camera 105 is inclined downward by a predetermined angle with respect to the normal of the display unit 100 so as to photograph a user well. In this instance, even if the user U has the same eye level with respect to the display unit 100, an eye level of the user U in a user image P captured by the camera 105 may vary depending on a distance between the display unit 100 and the user U.

Figure 16:
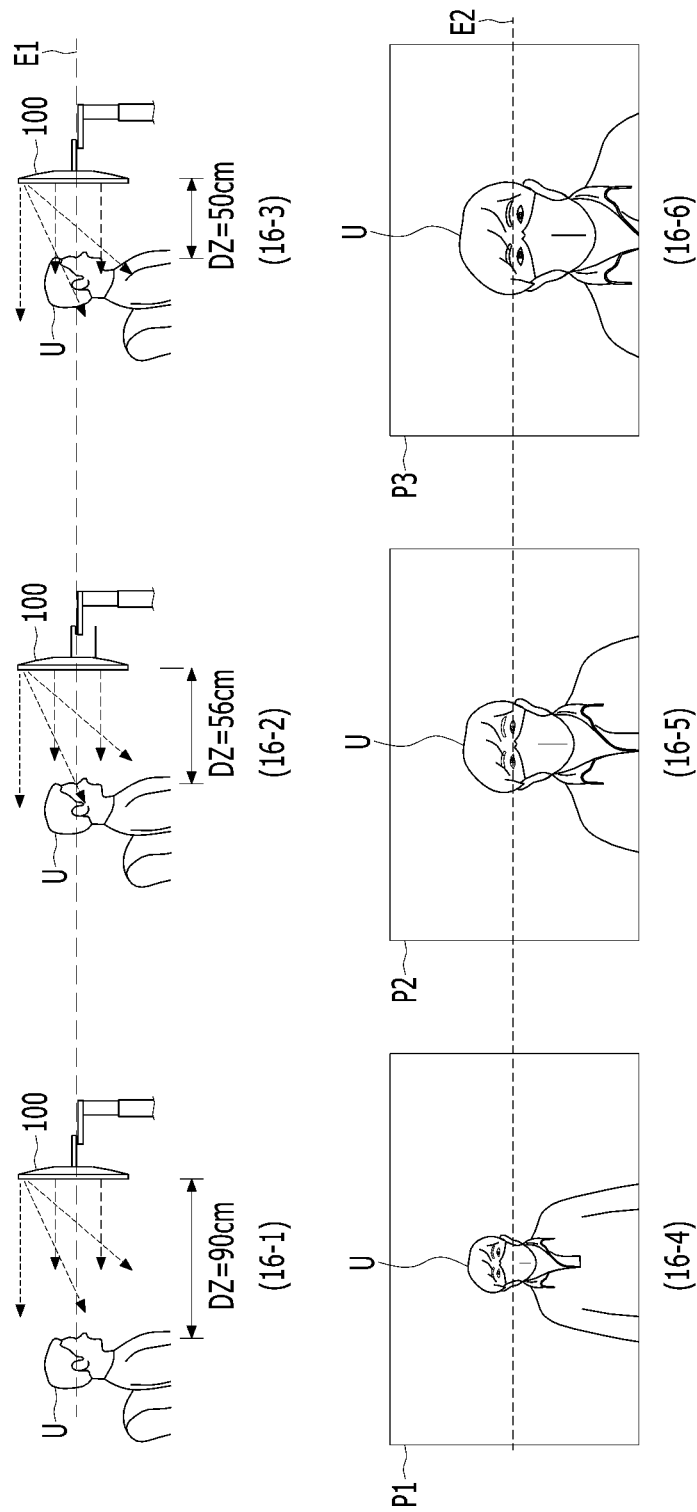
FIG. 16 is a diagram showing a change in a user's eye level in a user image photographed by a camera mounted on a display unit depending on a distance between the user and the display unit according to an embodiment of the present disclosure.

More specifically, (16-1), (16-2), and (16-3) of FIG. 16 show three cases in which the user U has the same eye level with respect to the display unit 100, but the distances between the display unit 100 and the user U are different. In (16-1), (16-2) and (16-3) of FIG. 16, a dotted line E1 indicating the height of the center of the display unit 100 is illustrated. Namely, in the three cases of (16-1), (16-2), and (16-3) of FIG. 16, the eye level of the user U corresponds to the height of the center of the display unit 100 in common, and a distance DZ between the display unit 100 and the user U is illustrated as 90 cm in FIG. 16 (16-1), 56 cm in FIGS. 16 (16-2), and 50 cm in FIG. 16 (16-3).

FIG. 16 (16-4) illustrates a first user image P1 photographed in FIG. 16 (16-1), FIG. 16 (16-5) illustrates a second user image P2 photographed in FIG. 16 (16-2), and FIG. 16 (16-6) illustrates a third user image P3 photographed in FIG. 16 (16-3). In the first user image P1, the second user image P2, and the third user image P3, a horizontal line crossing the middle of the vertical length is indicated by a dotted line E2.

In the first user image P1, the eye level of the user U is positioned higher than the dotted line E2. In the second user image P2, the eye level of the user U is positioned on the dotted line E2. In the third user image P3, the eye level of the user U is positioned lower than the dotted line E2. That is, even if the user U has the same eye level with respect to the display unit 100 in the three cases (16-1), (16-2), and (16-3) of FIG. 16, the eye level of the user U can vary in the first to third user images P1 to P3 captured by the camera 105 as the distance between the display unit 100 and the user U varies.

Therefore, in order to more accurately obtain a posture (especially, face or eye level) of the user U taken through the camera 105 mounted on the display unit 100, it is preferable to obtain the distance DZ between the display unit 100 and the user or the distance D between the camera 105 mounted on the display unit 100 and the user.

Hereinafter, the user's 3D body skeleton of the user will be described with reference to FIG. 17. In particular, FIG. 17 is a diagram to describe a user's 3D body skeleton recognition according to an embodiment of the present disclosure.

If an actual binocular distance PD of the user U is known, a distance D between the camera 105 and the face of the user U can be calculated from the number of pixels (or pixel distance) pd in the user image P corresponding to the actual binocular distance PD of the user U based on the equation shown in FIG. 15 (15-3). However, from the point of view of the controller 350, it may be difficult to check whether the user U is looking at the display unit 100 (or the camera 105) squarely or sideways with the user image P only.

Even if the distance D between the camera 105 and the face of the user U is the same, the number of pixels (or a pixel distance) pd corresponding to the actual binocular distance PD of the user U in the user image P may vary depending on an opposite direction of the user U (i.e., whether the user U looks at the display unit 100 squarely or sideways). Therefore, in order to accurately obtain the distance D between the camera 105 and the user U, it is preferable to obtain a posture such as the opposite direction of the user U and correct the number of pixels (or pixel distance) pd corresponding to the actual binocular distance PD of the user U according to the obtained posture of the user (U).

In more detail, the controller 350 can analyze the user image P as shown in FIG. 17 (17-1), thereby recognizing user's 3D body skeleton as shown in FIG. 17 (17-2). That is, the controller 350 can analyze the user image P as shown in FIG. 17 (17-1), thereby identifying various body parts of the user, such as a head H, a shoulder S, a chest C, a right arm RA, and a left arm LA.

The controller 350 can generate a three-dimensional body skeleton of the user as illustrated in FIG. 17 (17-2) based on the identified various body parts of the user. Based on the three-dimensional body skeleton, positions of the various body parts of the user in a direction Z from the display unit 100 to the user U can be obtained. The various body parts of the user, such as the head H, the shoulder S, the chest C, the right arm RA, and the left arm LA, may be three-dimensionally identified through the three-dimensional body skeleton of FIG. 17.

Accordingly, the controller 350 can obtain a user's posture such as the opposite direction based on the three-dimensional body skeleton, and correct the number of pixels (or pixel distance) pd corresponding to the actual binocular distance PD of the user U according to the identified user posture.

Hereinafter, an example (not limited thereto) of the user's posture information obtainable from the distance D between the camera 105 and the face of the user U and the 3D body skeleton will be described with reference to FIG. 18. In particular, FIG. 18 illustrates an example of the user's posture information that can be obtained from the 3D body skeleton of FIG. 17. FIG. 18 illustrates the camera 105 protrudes upward from the top end portion of the display unit 100. However, the following description can be applied if the camera 105 is provided to a top end edge of the display unit 100 as mentioned above.

Examples of the user's posture information that can be obtained from the distance D between the camera 105 and the face of the user U and the three-dimensional body skeleton are described as follows.

1) As shown in (18-1) and (18-2) of FIG. 18, a position of a point OP (hereinafter referred to as a "normal point") where a normal line on the display panel facing the user's eyes intersects a plane of the display panel can obtained.

2) As shown in (18-1) and (18-2) of FIG. 18, a position of a point (GP) (hereinafter referred to as a "gaze point") at which a user's gaze intersects a plane of the display panel can be obtained.

3) As shown in (18-1) of FIG. 18, a spaced distance (or position) of the user eye in the Z direction from the normal point OP, i.e., a Z-direction distance DZ can be obtained.

4) As shown in (18-1) and (18-2) of FIG. 18, a spaced distance of the user eye, i.e., a Y-direction distance DY, in a vertical direction (i.e., the Y-direction) of the display panel from the position of the camera 105 can be obtained.

5) As shown in (18-2) of FIG. 18, a spaced distance of the user eye, that is, an X-direction distance DX, can be determined in a horizontal direction (i.e., an X direction) of the display panel from the position of the camera 105.

This is merely exemplary and can be obtained from other posture information of the user. For example, as described above, the opposite direction of the user U can be obtained from the 3D body skeleton. In addition, whether the user is in a turtle-neck posture from the 3D body skeleton can be obtained. In order to obtain the normal point and/or the gaze point, the display device may include an eye-tracking sensor.

Figure 19:
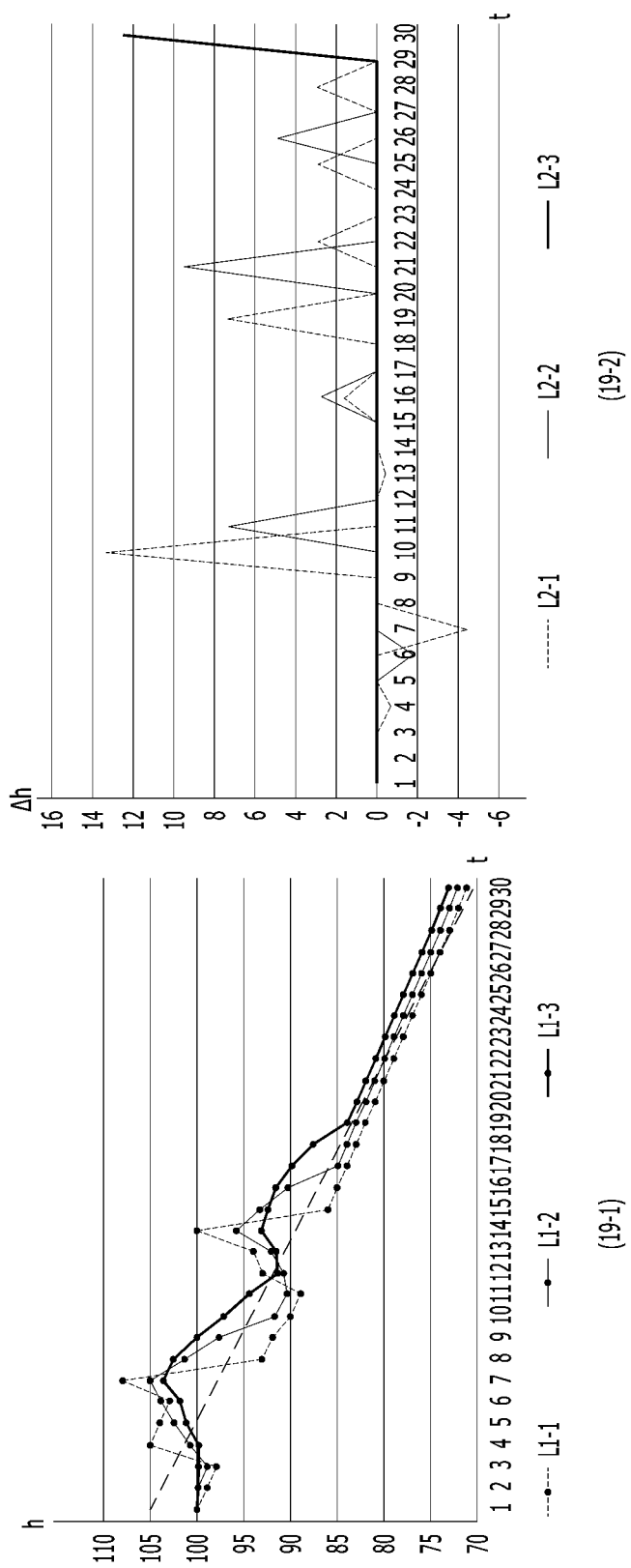
FIG. 19 illustrates an example of a change in a detected user's posture according to an embodiment of the present disclosure.

As described above, the controller 350 can adjust the posture of the display unit 100 through at least one of the tilting driving unit 180, the height adjusting unit 280, and the distance adjusting unit 190 based on the user's posture information. However, whenever the user's posture changes even a little, if the posture of the display unit 100 immediately and sensitively changes according to the changed user's posture, this can cause dizziness to the user. Accordingly, it is preferable to change the posture of the display unit 100 when the user's posture is changed to a predetermined level or more. This will be described further with reference to FIG. 19. In particular, FIG. 19 illustrates an example of a change in a detected user's posture according to an embodiment of the present disclosure.

A graph (hereinafter, a first graph) of FIG. 19 (19-1) shows a real-time height of a user's face (or eye) by time. That is, a 1-1 line L1-1 of the first graph represents a value obtained by measuring a height change of a user's face in real time, a 1-2 line L1-2 of the first graph represents an average value of the 1-1 line L1-1 per first unit time, and a 1-3 line L1-3 of the first graph represents an average value of the 1-1 line L1-1 per second unit time greater than the first unit time.

A graph (hereinafter, a second graph) of FIG. 19 (19-2) shows a variation amount of each line of the first graph. That is, a 2-1 line L2-1 of the second graph shows a variation of the 1-1 line L1-1 of the first graph, a 2-2 line L2-2 of the second graph shows a variation of the 1-2 line L1-2 of the first graph, and a 2-3L line L3 of the second graph shows a variation of the 1-3 line L1-3 of the first graph.

Instead of controlling the posture change of the display unit (100) according to the 1-1 line L1-1 of the first graph, the controller 350 can control the posture change of the display unit 100 according to the 1-2 line L1-2 or the 1-3 line L1-3 of the first graph. Because the 1-2 line L1-2 and the 1-3 line L1-3 of the first graph show average values per prescribed unit time, if the 1-2 line L1-2 or the 1-3 line L1-3 of the first graph is used, the posture of the display unit 100 can be adjusted less sensitively than when using the 1-1 line L1-1 of the first graph.

Alternatively, the controller 350 can control a change in the posture of the display unit 100 according to any one of the 2-1 line L2-1, the 2-2 line L2-2 and the 2-3 line L2-3 of the second graph. That is, when using any one of the 2-1 line L2-1, the 2-2 line L2-2 and the 2-3 line L2-3 of the second graph, the controller 350 can control a change in the posture of the display unit 100 when the absolute value of the variation according to the corresponding line becomes equal to or greater than a prescribed value. Further, the posture of the display unit 100 can be adjusted less sensitively than when using the 1-1 line L1-1 of the first graph.

In the above description, if the actual binocular distance PD of the user (U) is known, the distance D between the camera 105 and the face of the user U can be calculated based on the equation shown in FIG. 15 (15-3) (e.g., the pinhole camera model equation), and the distance D between the camera 105 and the face of the user U is required to accurately obtain the posture (particularly, height) of the user U captured by the camera 105 provided to the display unit 100. Hereinafter, a calibration for measuring the actual binocular distance PD of the user U will be described.

Figure 20:
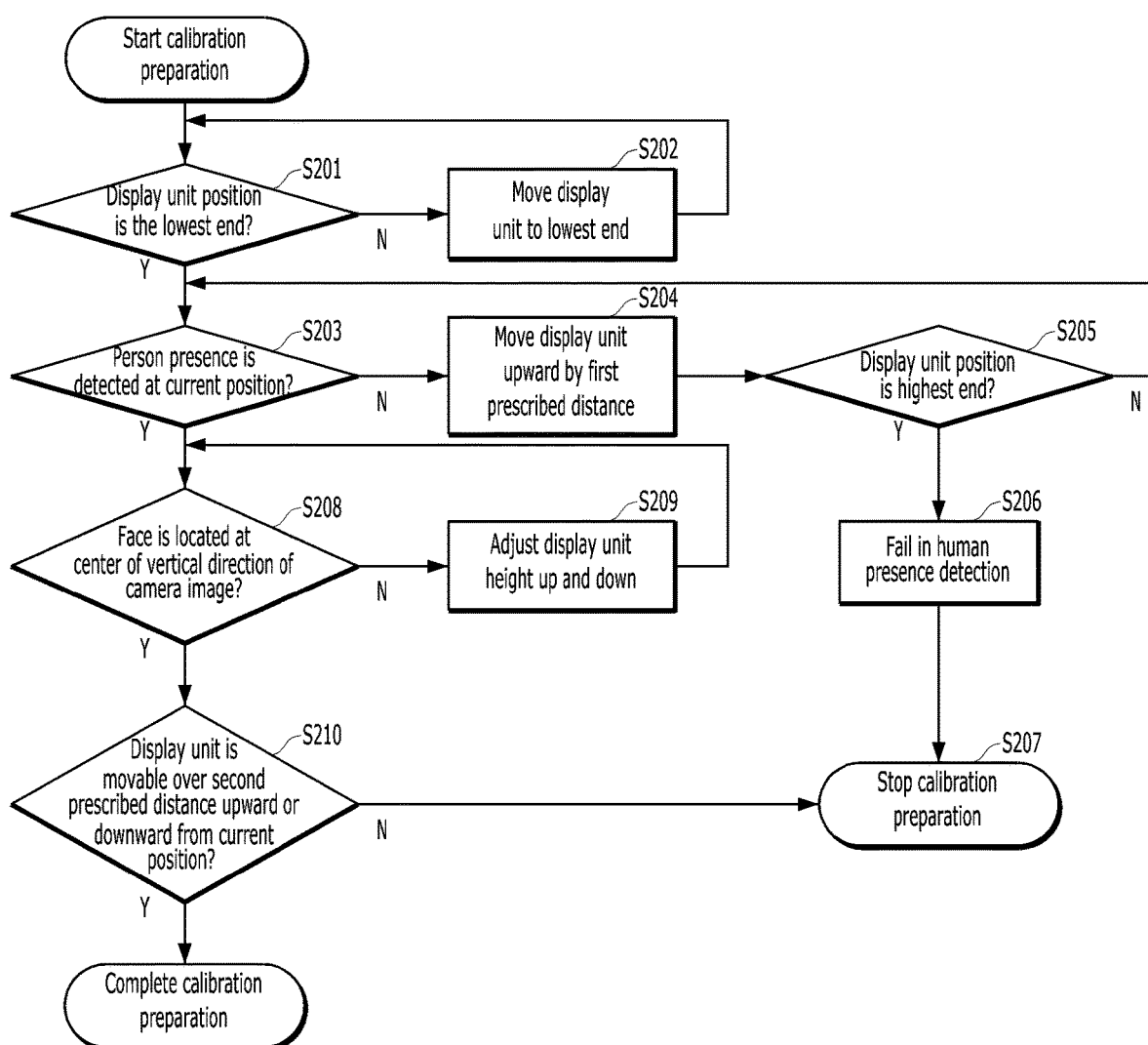
FIG. 20 is a flowchart of a calibration preparation process according to an embodiment of the present disclosure.
Figure 21:
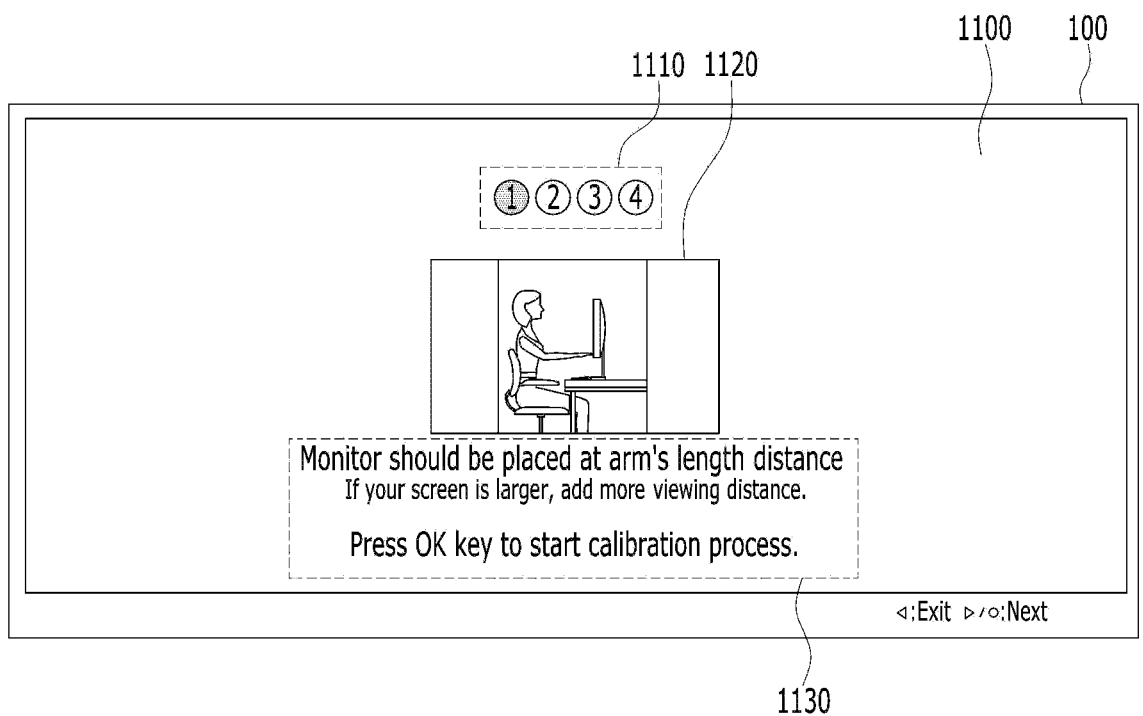
FIGS. 21 and 22 illustrate a guide screen displayed to guide calibration according to an embodiment of the present disclosure.
Figure 22:
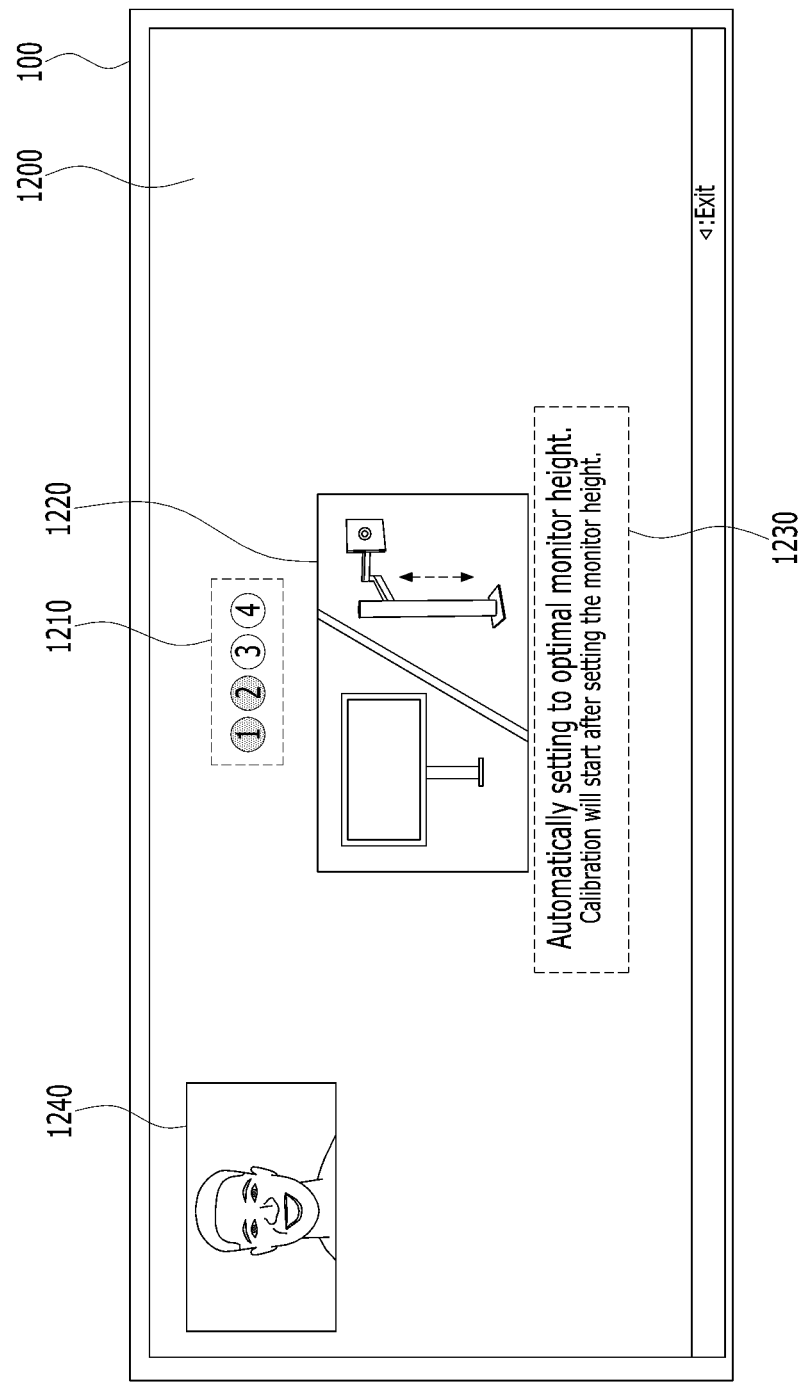

First, the preparation of the calibration will be described with reference to FIGS. 20 to 22. In particular, FIG. 20 is a flowchart of a calibration preparation process according to an embodiment of the present disclosure. Also, FIG. 21 and FIG. 22 illustrate a guide screen displayed to guide calibration according to an embodiment of the present disclosure.

The start of the calibration preparation process can be performed when the display device is powered on and/or a prescribed command is input from a user through the signal input unit 355. Once the display device is powered on or the prescribed command is input through the signal input unit 355, the controller 350 can control the display unit 100 to display a first guide screen 1100 for guiding the user to perform calibration as shown in FIG. 21. An execution step notification icon 1110 for notifying a current execution step of the calibration can be displayed on the first guide screen 1100.

A user posture guide image 1120 can be displayed on the first guide screen 1100 to guide the posture that the user should take for the calibration. The posture to be taken by the user (hereinafter, referred to as "user basic posture") can be the posture that the user may take most accurately and comfortably when spaced apart from the display unit 100 by a prescribed distance and looking at the display unit 100. In the first guide screen 1100, the prescribed distance is illustrated as a user arm length distance. The prescribed distance can vary depending on a size of the display unit 100. The prescribed distance can thus correspond to a distance such that there is a 3D image described below can be implemented.

In addition, the first guide screen 1100 can display a guide description 1130 explaining the actions that the user should take to prepare for the calibration. When the calibration preparation process starts, the controller 350 can determine whether a current position of the display unit 100 is the lowest end (S201). As a result of the determination, if the current position of the display unit 100 is not the lowest end, the display unit 100 can be controlled to move to the lowest end until the current position of the display unit 100 becomes the lowest end (S202).

When the current position of the display unit 100 becomes the lowest end, the controller 350 can determine whether a person (i.e., a user of the display unit 100 can be detected through the camera 105 by activating the camera 105 at the current position of the display unit 100 (S203). To this end, 2D face landmark recognition and/or 3D body skeleton recognition can be used.

When it is determined that a person does not exist, the controller 350 can gradually move the display unit 100 by a first prescribed distance in a top end direction until it is detected that a person exists (S203, S204, S205). Even if the display unit 100 is moved to the highest end position, when the controller 350 fails to detect the presence of a person, the controller 350 can determine that it has failed to detect the presence of a person (i.e., determining that the calibration cannot be further progressed) and stop the calibration preparation process (S206, S207).

When it is determined that a person exists, the controller 350 can determine whether a face of the detected person is located in the center of the vertical direction in an image captured by the camera 105 (S208). The controller 350 can control the height of the display unit 100 to be adjusted so that the person's face is located at the center in the camera image if the person's face is not located at the center in the camera image (S209).

When the person's face is located at the center in the camera image, the controller 350 can determine whether the display unit can move upward or downward from a current position by a second prescribed distance (for example, 5 cm). The second prescribed distance can be equal to or shorter/longer than the first prescribed distance. When the display unit can move upward or downward by the second prescribed distance or more from the current position, the controller 350 can determine that the calibration can continue to be performed, and complete the preparation process of the calibration.

However, if the display unit cannot move by the second prescribed distance upward or downward from the current position, the controller 350 can determine that the calibration cannot be further progressed and stop the calibration preparation process (S207). In addition, the controller 350 can control a second guide screen 1200 to be displayed to guide the user to perform the calibration, as shown in FIG. 22, while moving the display unit 100 up and down during the calibration preparation process.

An execution step notification icon 1210 for notifying the current execution step of the calibration can be displayed on the second guide screen 1200. A guide image 1220 and a guide description 1230 indicating that the display unit 100 is moveable up and down for the calibration can be displayed on the second guide screen 1200. In addition, an image 1240 captured by the camera 105 can be displayed on the second guide screen 1200.

In the above preparation process of the calibration, it has been described that the presence of a person is determined while the display unit 100 is moved from the lowest end to the highest end. However, the present disclosure is not limited thereto. For example, the display unit 100 can be configured to determine the presence of a person while being moved in a lower end direction from the highest end.

Figure 25:
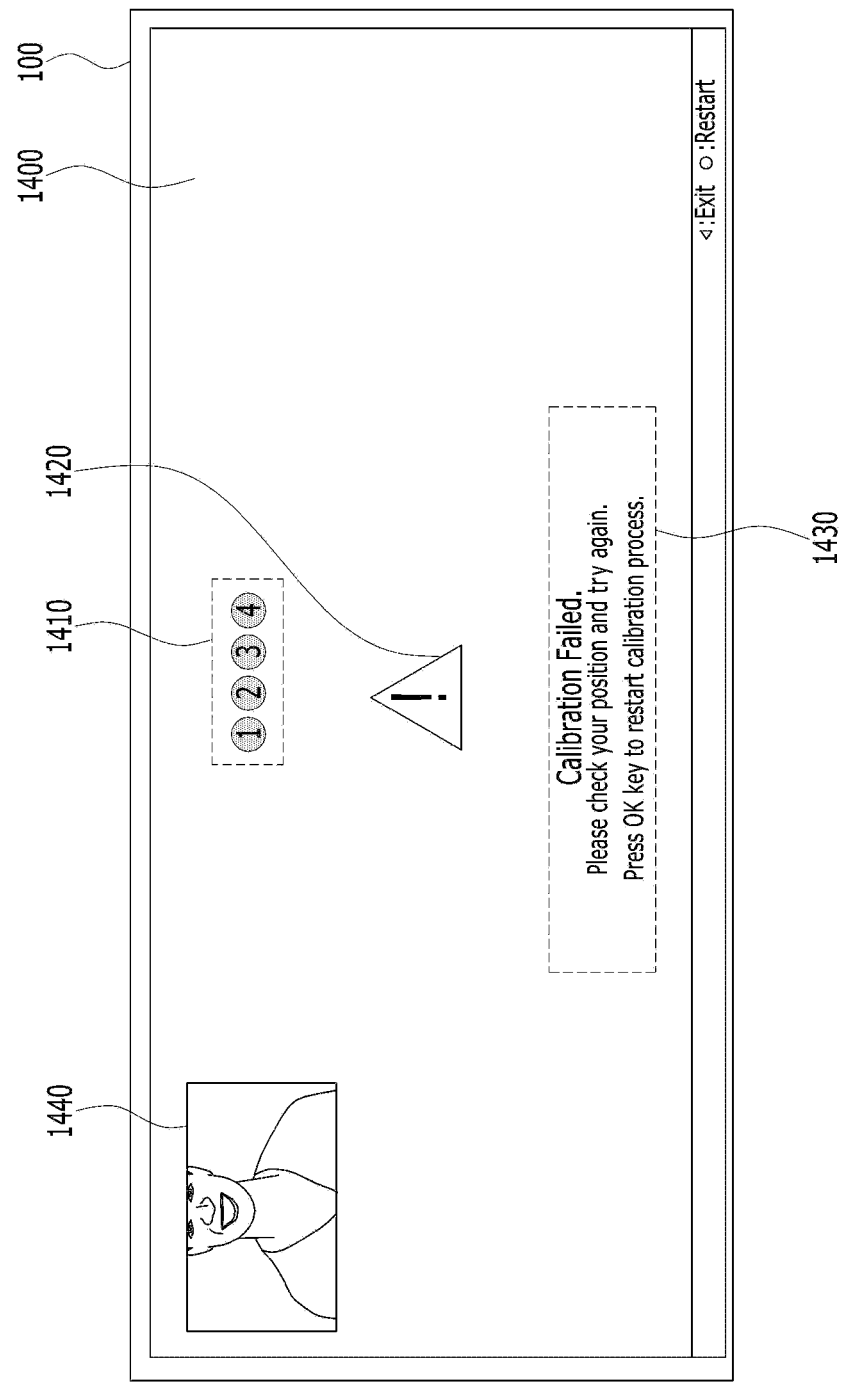
Figure 26:
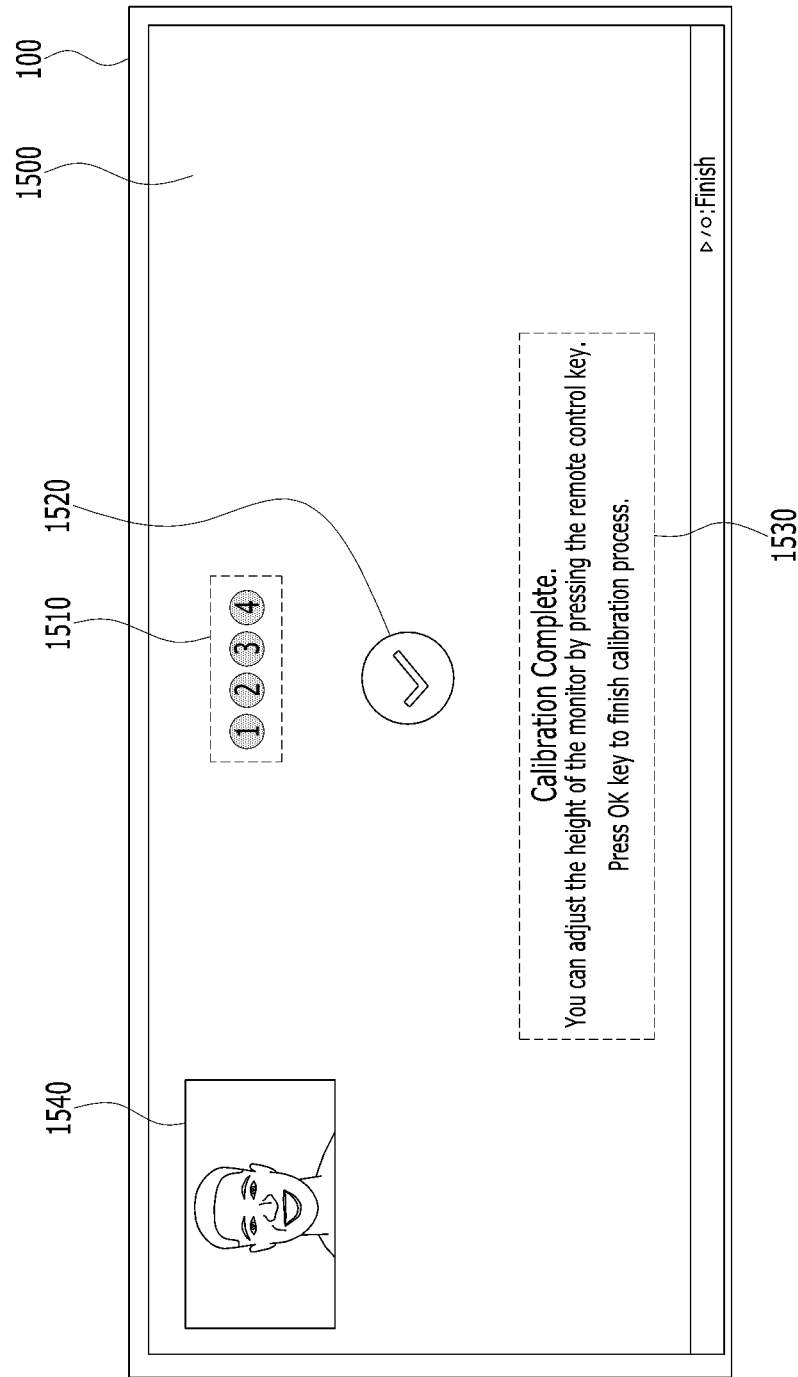

When the preparation process of the calibration is completed, the calibration can be performed regularly. A process of performing the calibration will be described with reference to FIGS. 23 to 26. In particular, FIG. 23 is a flowchart of a process of executing calibration according to an embodiment of the present disclosure, and FIGS. 24 to 26 illustrate guide screens displayed to guide calibration according to an embodiment of the present disclosure.

Figure 23:
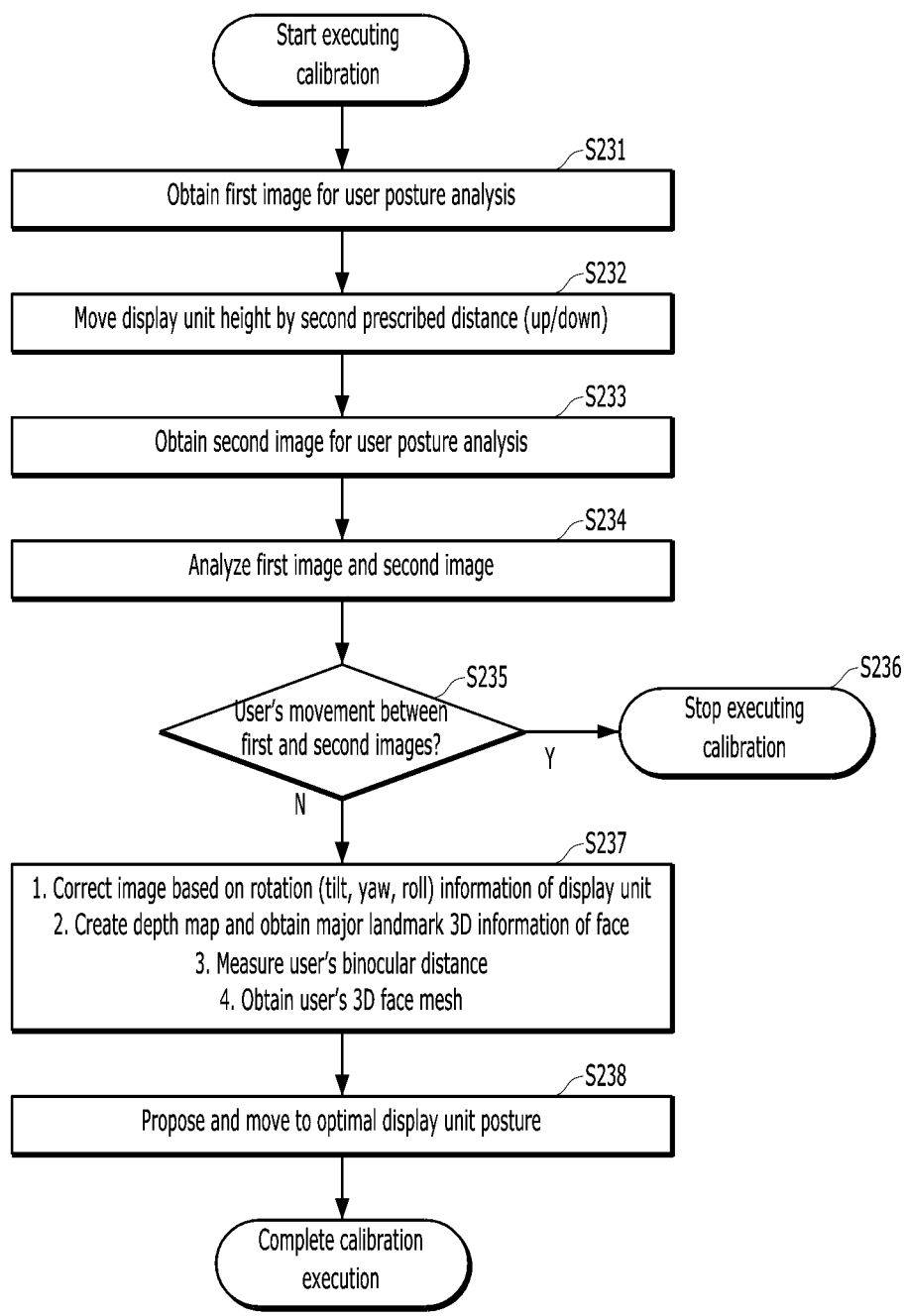
FIG. 23 is a flowchart of a process of executing calibration according to an embodiment of the present disclosure.

As shown in FIG. 23, the controller 350 can obtain a first user image frame in which a user maintaining a basic posture in the display unit 100 as a subject through the camera 105 at a current position of the display unit 100 (S231). After obtaining the first user image frame, the controller 350 can control the display unit 100 to move from the current position to an upper or lower position, which is spaced apart by a second prescribed distance (S232).

In addition, the controller 350 can obtain a second user image frame in which the user maintains the basic posture in the display unit 100 as a subject through the camera 105 at the moved position (S233). The second prescribed distance can be defined as a minimum distance enough to implement a 3D image with respect to the user using the first user image frame and the second user image frame.

Figure 24:
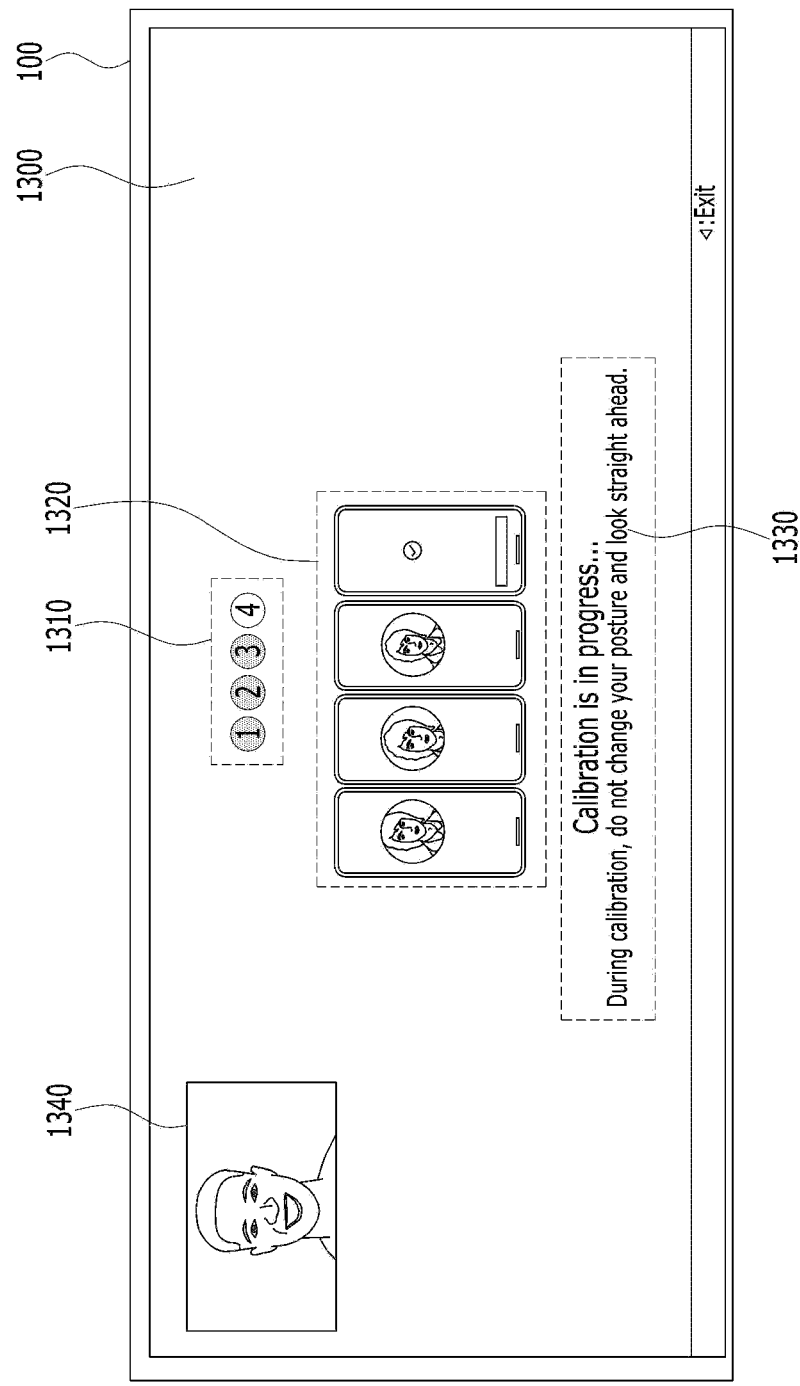
FIGS. 24 to 26 illustrate guide screens displayed to guide calibration according to an embodiment of the present disclosure.

The controller 350 can control the display unit 100 to display a third guide screen 1300 to guide the user to perform calibration, as illustrated in FIG. 24, while moving the display unit 100 upward or downward to obtain the first user image frame and the second user image frame. An execution step notification icon 1310 for notifying the current execution step of the calibration can be displayed on the third guide screen 1300.

A guide image 1320 indicating that the first user image frame and the second user image frame are being obtained can be displayed on the third guide screen 1300. Since the first user image frame and the second user image frame are being obtained, a guide description 1330 requesting to maintain the user posture can be displayed on the third guide screen 1300. In addition, an image 1340 captured by the camera 105 can be displayed on the third guide screen 1300.

The controller 350 can analyze the first user image frame and the second user image frame to determine whether there is a user's movement in the first user image frame and the second user image frame (S234, S235). Namely, whether the user's movement within the first user image frame and the second user image frame is within a prescribed number of pixels (or pixel distance) can be obtained. This is to prepare for when a user tries to maintain the basic posture, but may move unintentionally.

Since the first user image frame and the second user image frame are obtained while the display unit moves in the vertical direction, the user's movement can be a left-right movement. Also, if the first user image frame and the second user image frame are obtained while the display unit moves in the vertical direction, the user's movement may be a vertical movement.

The horizontal (i.e., left-to-right) movement can be determined based on a user's feature point (e.g., eyes, nose, philtrum, face contour, etc.) in the first user image frame and the second user image frame. The prescribed number of pixels can be defined as a maximum pixel value that will not be problematic in implementing a 3D image for the user using the first user image frame and the second user image frame.

If it is determined that the user's movement within the first and second user image frames is not within the prescribed number of pixels (i.e., if it is determined that there is a user movement), the controller 350 determines that calibration can no longer be executed and can stop the calibration execution process (S236). When the calibration execution process is stopped, the controller 350 can control a fourth guide screen 1400 displaying that the calibration execution process as shown in FIG. 25 is stopped.

An execution step notification icon 1410 for notifying a current execution step of the calibration can be displayed on the fourth guide screen 1400. On the fourth guide screen 1400, a guide image 1420 and a guide description 1430 indicating that the calibration execution process has been stopped can be displayed. In addition, an image 1440 captured by the camera 105 can be displayed on the fourth guide screen 1400. The fourth guide screen 1400 can be displayed even when the calibration preparation process is stopped in the step S207.

When it is determined that the user's movement within the first user image frame and the second user image frame is within the prescribed number of pixels (i.e., it is determined that there is no user movement), the controller 350 can perform the following operation (S237).

1) The controller 350 can correct at least one of the first user image frame and the second user image frame based on orientation information (i.e., information on at least one of tilt, yaw, and roll) of the display unit when obtaining the first and second user image frames. This is because an optical axis of the camera 105 may not be accurately perpendicular to a vertical movement direction of the display unit 100 depending on the orientation direction of the display unit 100. That is, at least one of the first user image frame and the second user image frame is corrected to correspond as if they were captured by a camera with an optical axis perpendicular to the vertical movement direction of the display unit 100.

2) The controller 350 can generate a depth map for the user using the first user image frame and the second user image frame, and obtain 3D landmark information on a face of the user.

3) The controller 350 can measure a spaced distance from the camera to the user through a position change with respect to the same feature point in the first user image frame and the second user image frame photographed by moving a second prescribed distance. In addition, the controller 350 can measure an actual binocular distance PD of the user using the depth map and the 3D landmark information.

4) The controller 350 can generate a 3D face mesh of the user using the depth map and the 3D landmark information.

Next, the controller 350 can calculate a display unit posture (or setting thereof) that is determined to be most suitable for the user based on the user's three-dimensional face mesh and adjust the posture (e.g., at least one of a height value, a tilting angle value, and a distance value) of the display unit 100 to provide the calculated optimal posture of the display unit 100, thereby proposing the user with the optimal posture of the display unit 100 (S238). The controller 350 can infer the optimal posture through the artificial intelligence model based on the user's 3D face mesh.

The controller 350 can control a fifth guide screen 1500, which is to guide the completion of the calibration execution process as illustrated in FIG. 26, to be displayed. An execution step notification icon 1510 for notifying a current execution step of the calibration may be displayed on the fifth guide screen 1500.

A guide image 1520 and a guide description 1530 indicating that the calibration execution process has been completed can be displayed on the fifth guide screen 1500. In addition, an image 1540 captured by the camera 105 can be displayed on the fifth guide screen 1500.

In the above, calculating the distance D between the camera 105 and the user by using the equation of the relationship between the actual binocular distance and the binocular pixel distance in FIG. 15 (15-3) using the actual binocular distance of the user has been described. However, in calculating the distance D between the camera 105 and the user, the actual binocular distance of the user may not be required. If proportion information between the spaced distance (hereinafter referred to as 'reference spaced distance') (measured during the calibration execution) between the camera and the user and the binocular pixel distance (hereinafter referred to as 'reference pixel distance') in the first image frame and/or the second image frame photographed during the calibration execution is stored, the spaced distance D between the camera 105 and the user U in the user image P in FIG. 15 (15-1) can be measured using the proportion information with the binocular pixel distance of the user image P in FIG. 15 (15-1) only. The actual binocular distance of the user and the proportion information can be collectively referred to as basic information for calculating a spaced distance of the user.

In the above description, obtaining a display unit posture or a setting thereof, which is determined to be the most suitable for a user in accordance with the calibration execution process, has been described. However, performing the calibration execution process may be omitted. Instead, the display device can present a setting for a pre-stored default display unit posture (hereinafter, also referred to as a "default setting") as a setting for an optimal posture of the display unit 100. Moreover, various default settings per user's gender and/or age can be stored. One of the various default settings can be called by allowing a user to directly enter his or her gender and/or age. Alternatively, a user's gender and/or age can be inferred through the artificial intelligence model, and a default setting corresponding to the inferred gender and/or age can be called. The setting for the optimal posture of the display unit 100 can be inferred through the artificial intelligence model based on the inferred gender and/or age.

In addition, instead of the actual binocular distance, a default binocular distance (i.e., an average actual binocular distance of a typical user pre-prepared by a manufacturer) (or basic information for calculating a spaced distance) can be used without the calibration execution process. Moreover, various default binocular distances (or basic information for calculating a spaced distance) per user's gender and/or age may be stored. One of the various default binocular distances (or basic information for calculating the spaced distance) can be called by allowing a user to directly enter his/her gender and/or age. Alternatively, the user's gender and/or age can be inferred through the artificial intelligence model, and among the various default binocular distances (or basic information for spaced distance calculation), a default binocular distance (or basic information for spaced distance calculation) may be called. Based on the inferred gender and/or age, the actual binocular distance (or basic information for calculating the spaced distance) of the user can be inferred through the artificial intelligence model. The actual binocular distance of the user may be input from the user through the signal input unit 355.

Figure 27:
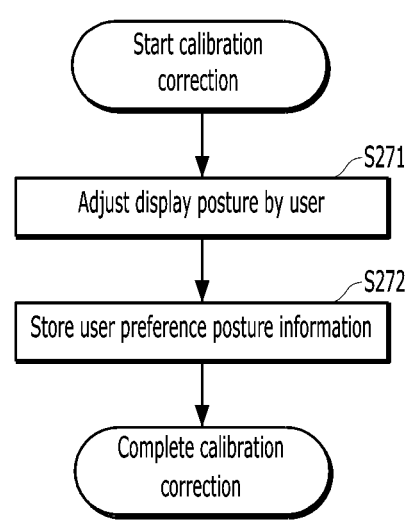
FIG. 27 is a flowchart of a modification process for modifying a user optimization posture of a display unit presented according to an embodiment of the present disclosure.

In addition, as the calibration execution process is completed, the proposed user optimization posture (i.e., a user-optimal display unit posture or a setting thereof) of the display unit 100 can be modified by the user. This will be described further with reference to FIG. 27. In particular, FIG. 27 is a flowchart of a modification process for modifying a user optimization posture of a display unit presented according to an embodiment of the present disclosure.

First, the controller 350 can receive a user command for adjusting a user optimization posture of the display unit from a user through the signal input unit 355. In other words, the user command is to further adjust at least one of the height, tilting angle, and distance of the display unit 100 so that a user optimization posture of the display unit is tailored to the user's basic posture according to the user's own preference.

The controller 350 can adjust a user optimization posture of the display unit by controlling at least one of the tilting driving unit 180, the height adjusting unit 280, and the distance adjusting unit 190 in response to the user command (S271). When the adjustment of the user optimization posture of the display unit is completed, the controller 350 can store the adjusted user optimization posture as a user-preferred display unit posture (or a user preference setting) (S272).

The controller 350 can store a height value, a tilting angle value, and a distance value of the display unit 100 according to the user-preferred display unit posture. Alternatively, the controller 350 can store the height, tilting angle, and distance values of the display unit 100 according to the proposed user optimization posture, and can store a height difference value, a tilting angle difference value, and a distance difference value, which correspond to a difference between the proposed user optimization posture and the user-preferred display unit posture, as offset values. If the proposed user optimization posture is not modified by the user, the controller 350 can store the proposed user optimization posture as the user preference setting.

In the above description, obtaining a user preference setting through the calibration execution for a user has been described. However, if the display device is used by multiple users, a user of the display device may have to perform the calibration execution anew every time a user changes. This can be cumbersome for the user.

Figure 28:
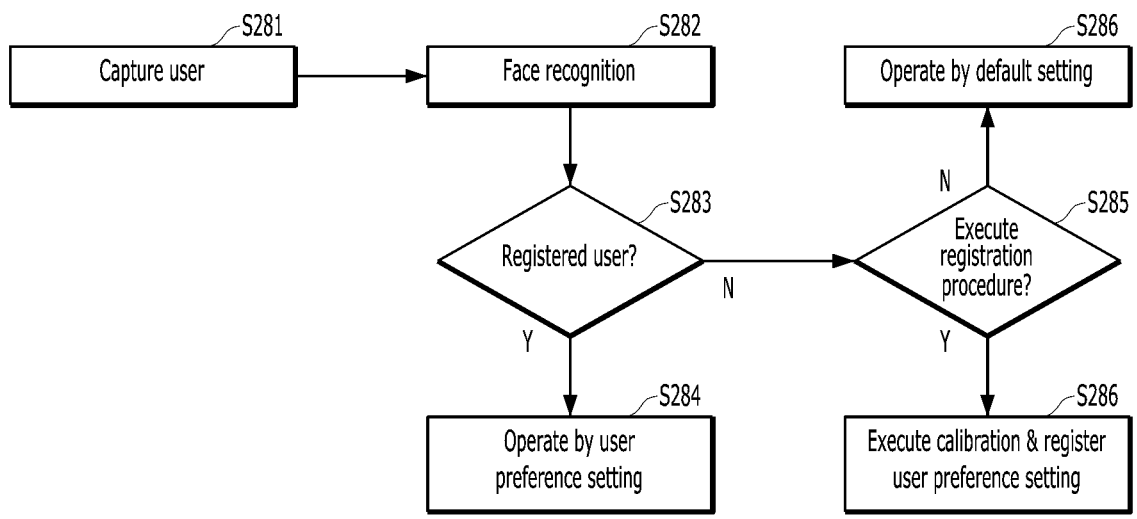
FIG. 28 is a flowchart of a process for calling or registering a preference setting for each user in a display device according to an embodiment of the present disclosure.

To solve this problem, each user can register his or her preferred posture on the display device and identify who is currently using the display device, so that a preferred posture for the identified user can be called or used. This will be described further with reference to FIG. 28. In particular, FIG. 28 is a flowchart of a process for calling or registering a preference setting for each user in a display device according to an embodiment of the present disclosure.

As shown, the controller 350 can photograph a user who is using the display device through the camera 105 (S281). The controller 350 can analyze the captured user image and identify a user in the image (S282). To this end, the controller 350 can utilize the artificial intelligence model stored in the artificial intelligence model storage unit 3505.

Next, the controller 350 can determine whether the identified user is a pre-registered user (S283). As a result of the determination, if the identified user is the pre-registered user, the controller 350 can call a user preference setting stored for the pre-registered user and control the display device to operate based on this (S284).

However, as a result of the determination, if the identified user is not the pre-registered user, the controller 350 can display a user interface for confirming whether the user will execute a registration procedure (S285). If the user does not desire to execute the registration procedure through the user interface, the controller 350 can call a default setting and control the display device to operate based the default setting (S286).

The controller 350 can store various default settings for each gender and/or age of the user. Accordingly, the controller 350 can infer gender and/or age through the artificial intelligence model even though the identified user is not a pre-registered user, and can call a default setting corresponding to the inferred gender and/or age.

However, if the user desires to execute the registration procedure through the user interface, the controller 350 can progress the calibration execution process to newly register the user and store the user preference setting determined through the calibration execution process to correspond to the user (S286). In this instance, the controller 350 can store an actual binocular distance PD of the user corresponding to the user and/or a 3D face mesh of the user to correspond to the user together. In this instance, the basic information for the spaced distance calculation can be stored instead of the user's actual binocular distance PD. In addition, the controller 350 can control the display device to operate based on the user preference setting for the user (S284).

Although the present disclosure has been described above to identify the user and register the user preference setting based on the artificial intelligence model, the present disclosure is not limited thereto. The calibration execution process can be performed while the user directly registers his or her identification information (e.g., a name), and a user preference setting determined through the calibration execution process can be stored to correspond to the registered identification information. Therefore, instead of the steps S281 and S283, the user inputs or selects his or her pre-registered identification information to the display device, so that it may be determined whether the user is a pre-registered user in the step S283.

Figure 29:
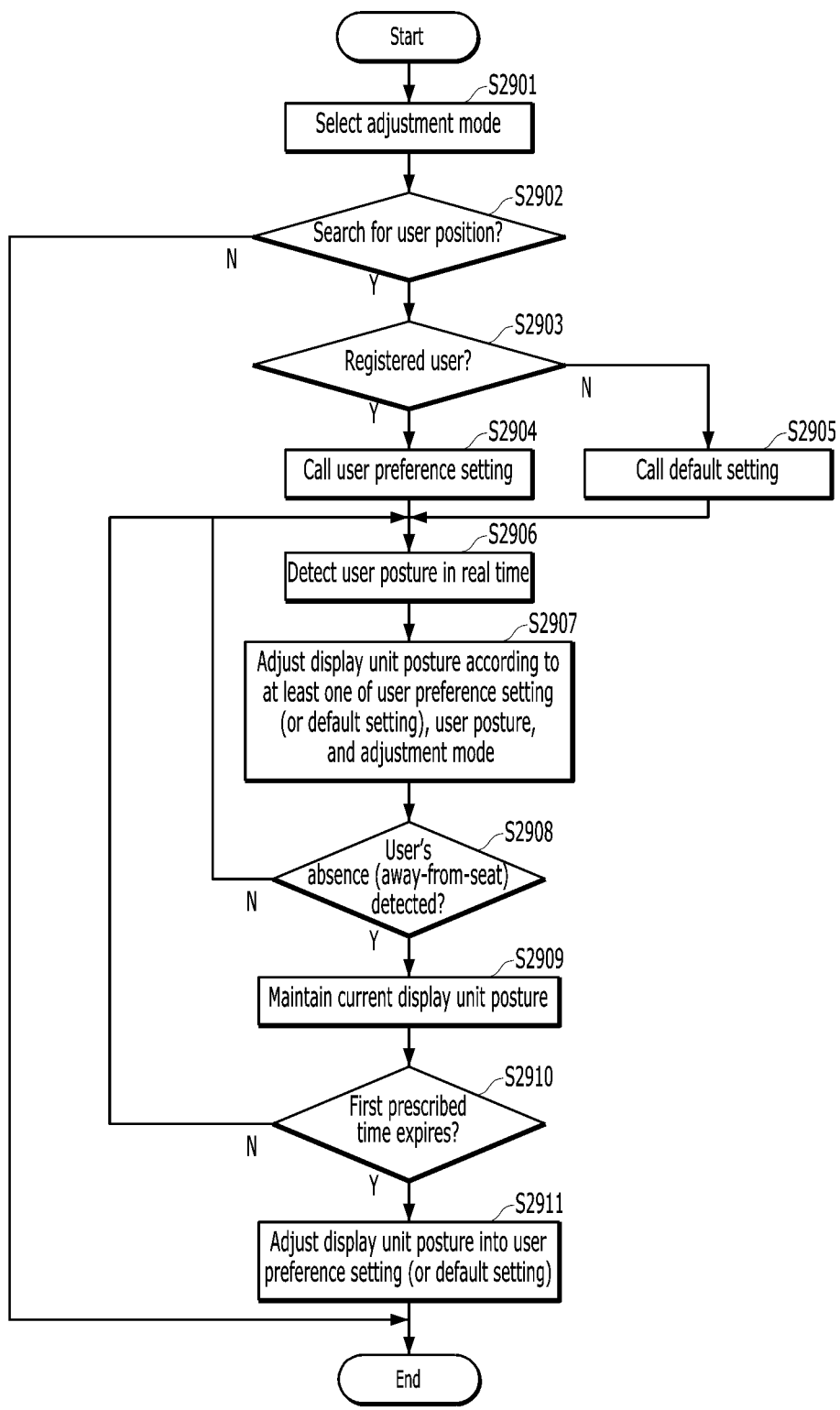
FIG. 29 is a flowchart illustrating posture adjustment of a display unit according to an embodiment of the present disclosure.

FIG. 14 illustrates the posture of the display unit 100 can be adjusted to match the posture of the user based on the posture information of the user. However, there can be various modes (or methods) for adjusting the posture of the display unit 100 to conform to the user's posture. Hereinafter, at least four adjustment modes are described in the present disclosure. In addition, the user preference setting described above can be further be considered in adjusting the posture of the display unit 100 to match the posture of the user. This will be described further with reference to FIG. 29. In particular, FIG. 29 is a flowchart illustrating a posture adjustment of a display unit according to an embodiment of the present disclosure.

First, the user can enter a menu mode of the display device and then select a desired adjustment mode (S2901). In the present disclosure, the following four adjustment modes are described.

1) First Adjustment Mode: User Posture Follow Adjustment Mode
2) Second Adjustment Mode: User Posture Follow and Calibration Adjustment Mode
3) Third Adjustment Mode: Continuous Adjustment Mode
4) Fourth Adjustment Mode: Random Adjustment Mode An operation of the display device according to each adjustment mode will be described again later.

Next, the controller 350 can search for a position of the user through the camera 105 (S2902). That is, the controller 350 can determine what kind of a user exists in front of the display device or the display unit 100. The process of searching for the position of the user will be described again later.

If the user's position search fails, i.e., if it is determined that the user does not exist in front of the display device, the controller 350 can stop the posture adjustment of the display unit 100 according to the selected adjustment mode. When the user's position search is performed, i.e., when it is determined that the user exists in front of the display device, the controller 350 can determine whether the position-searched user is a pre-registered user (S2903). The determination of a presence or non-presence of the pre-registered user can be the same as described above with reference to FIG. 28.

If the user is the pre-registered user, the controller 350 can call a user preference setting preset for the user (S2904). If the user is not the pre-registered user, the controller 350 can call a default setting (S2905). Calling the user preference setting and calling the default setting are the same as described above with reference to FIG. 28.

Next, the controller 350 can obtain a user's image in real time through the camera 105 and detect the user's posture in real time (S2906). The user's posture detection is the same as described above with reference to FIGS. 14 to 18. Next, the controller 350 can adjust a posture of the display unit 100 according to at least one of the setting (i.e., the user preference setting or the default setting), the selected adjustment mode, and the detected user posture (S2907). The step S2907 will be described later for each adjustment mode.

While the posture of the display unit 100 is being adjusted, the controller 350 can detect whether the user is away from a seat (S2908). A process for detecting the user's absence (i.e., 'away-from-seat') will be described again later. If the user's absence is not detected, the controller 350 can continue to perform the step S2906 and the step S2907. However, when the user's absence is detected, the controller 350 can control a current posture of the display unit 100, that is, the posture last adjusted before the user's absence is detected in the step S2907 (S2909).

Next, the controller 350 can determine whether the time for maintaining the absence passes a first prescribed time (e.g., 5 minutes) (S2910). If the time for maintaining the absence does not pass the first prescribed time, the controller 350 can perform the step S2906 and the step S2907. However, after the for maintaining the absence passes the first prescribed time, the controller 350 can adjust the posture of the display unit 100 to the setting (i.e., the user preference setting or the default setting), and can finish the posture adjustment of the display unit 100 according to the selected adjustment mode (S2911).

Figure 30:
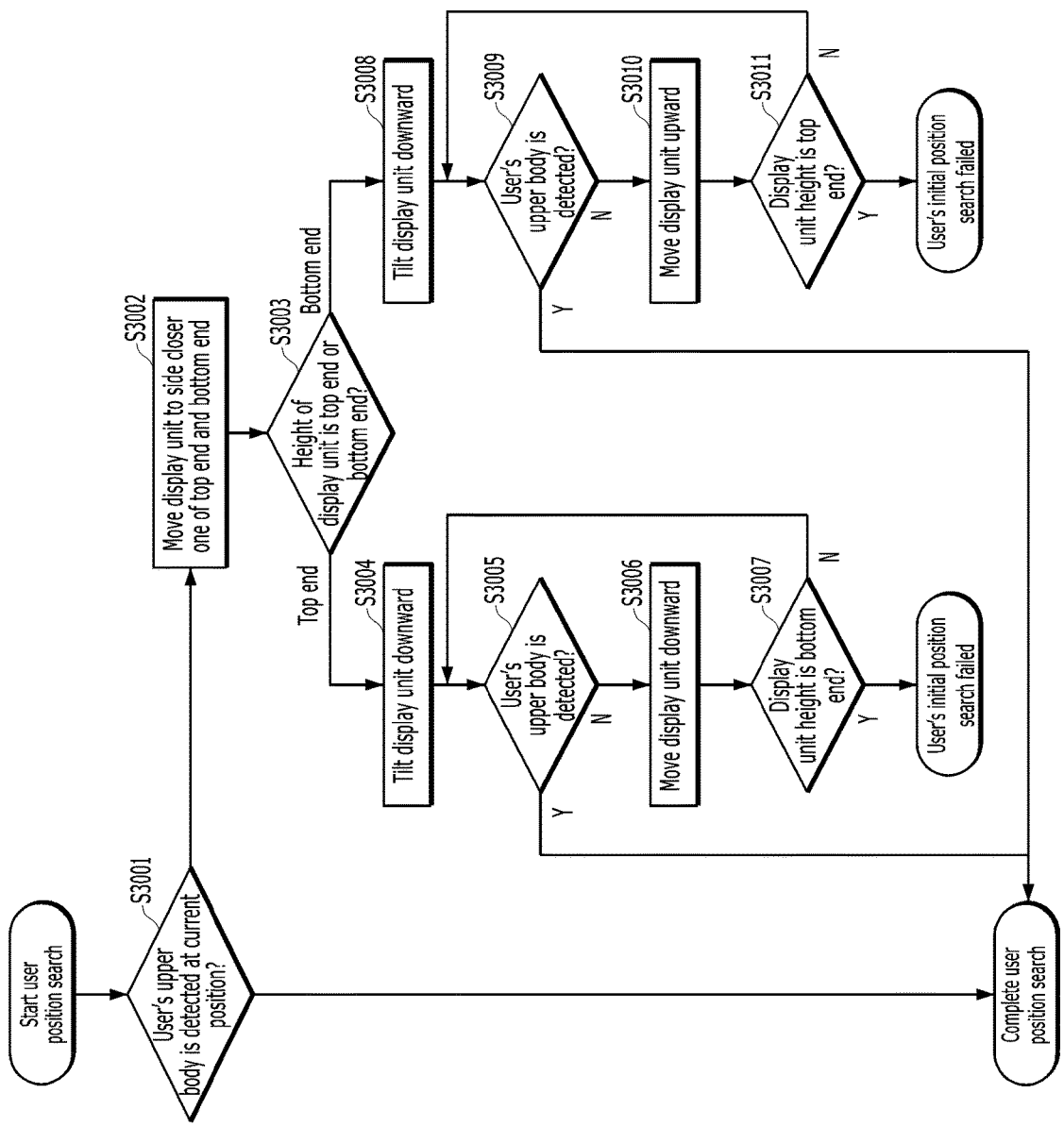
FIG. 30 is a flowchart for a display device to search for a user according to an embodiment of the present disclosure.

Hereinafter, the process for searching for the user's position mentioned in the step S2902 of FIG. 29 will be described with reference to FIG. 30. In particular, FIG. 30 is a flowchart for a display device to search for a user according to an embodiment of the present disclosure.

The controller 350 can determine whether an upper body (e.g., face and/or shoulder line) of the user is detected through the camera 105 in a current posture of the display unit at the timing point of searching for a position of the user (S3001). When the upper body of the user is detected, the controller 350 can complete the user's position search.

If the user's upper body is not detected in the step S3001, the controller 350 can move the display unit 100 to a side closer to a current position (or height) according to the current posture between a top end position where the display unit 100 can rise the highest and a bottom end position where the display unit 100 can rise the lowest (S3002). If the current position corresponds to any one of the top end position and the bottom end position, the display unit 100 does not need to be moved.

If the display unit 100 is in the top end position as a result of performing the step S3002, the controller 350 can adjust the posture of the display unit 100 so that the display unit 100 tilts from a top side direction to a bottom side direction (S3003, S3004). The controller 350 can determine whether the upper body of the user is detected through the tilting of the display unit 100 (S3005).

When the upper body of the user is detected through the tilting of the display unit 100, the controller 350 can complete the search for the user's position. However, if the user's upper body is not detected, the controller 350 can determine whether the user's upper body is detected while moving the position of the display unit 100 from the top end position to the bottom end position (S3006, S3007, S3005).

When the upper body of the user is detected through the position movement of the display unit 100, the controller 350 can complete the user's position search. However, if the user's upper body is not detected even though the position of the display unit 100 has been moved to the bottom end position, the controller 350 can determine that the user's position search has failed.

In addition, if the display unit 100 is at the bottom end position as a result of performing the step S3002, the controller 350 can adjust the posture of the display unit 100 so that the display unit 100 tilts from a bottom side direction to a top side direction (S3003, S3008). The controller 350 can determine whether the upper body of the user is detected through the tilting of the display unit 100 (S3009).

When the upper body of the user is detected through the tilting of the display unit 100, the controller 350 can complete the search for the user's position. However, if the user's upper body is not detected, the controller 350 can determine whether the user's upper body is detected while moving the position of the display unit 100 from the bottom end position to the top end position (S3010, S3011, S3009).

When the upper body of the user is detected through the position movement of the display unit 100, the controller 350 can complete the user's position search. However, if the user's upper body is not detected even though the position of the display unit 100 has been moved to the top end position, the controller 350 can determine that the user's position search has failed.

Figure 31:
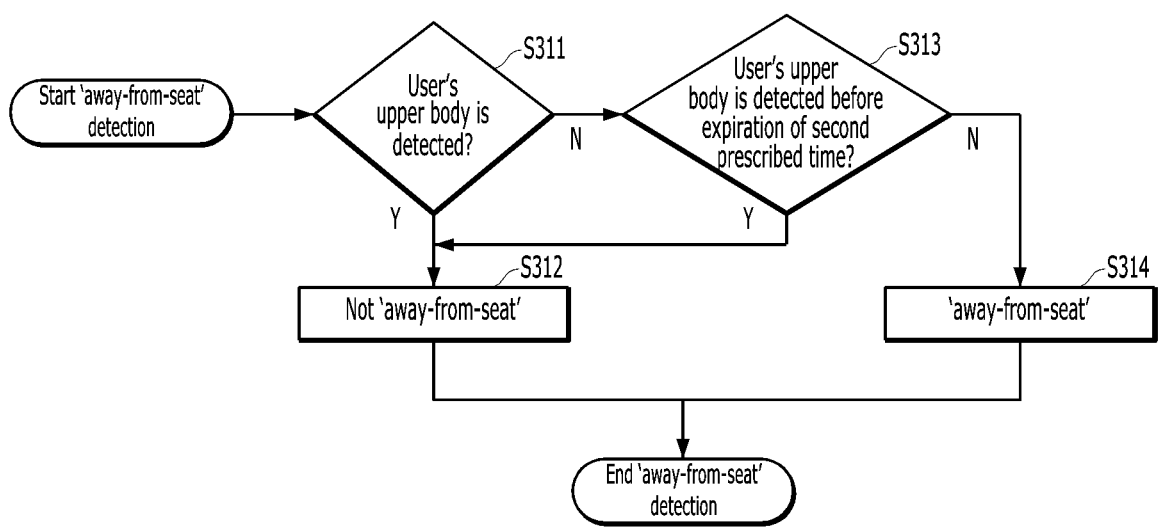
FIG. 31 is a flowchart for a display device to detect user's absence (e.g., away-from-seat) according to an embodiment of the present disclosure.

Hereinafter, a process of detecting the user's absence mentioned in the step S2908 of FIG. 29 will be described with reference to FIG. 31. In particular, FIG. 31 is a flowchart for a display device to detect user's absence (e.g., away-from-seat) according to an embodiment of the present disclosure.

Even while the posture of the display unit 100 is being adjusted, the controller 350 can determine in real time or periodically whether the user's upper body is detected (S311). When the upper body of the user is detected, the controller 350 can determine that it is not the user's absence ('away-from-seat') (S312). However, if the user's upper body is not detected, the controller 350 can continue to determine whether the user's upper body is not detected from the timing point of not detecting the user's upper body until expiration of a second prescribed time (e.g., 30 seconds) (S313).

When the upper body of the user is detected before the expiration of the second prescribed time, the controller 350 can determine that it is not the user's absence (i.e., 'away-from-seat') (S312). However, if the upper body of the user is not continuously detected until the second prescribed expires (e.g., 30 seconds), the controller 350 can determine that it is not the user's absence (S314).

In the above description, the posture of the display unit is adjusted according to the detected posture of the user. However, the method of adjusting the posture of the display unit can vary according to the type or mode of the user's detected posture. For example, if the user is sitting upright at work, it may be desirable to adjust the posture of the display unit so that the height of the display unit rises and falls accordingly as the user's face rises and falls. However, when the user is watching a movie and is sitting with his or her upper body straight back, it may be desirable to adjust the posture of the display unit so that the height of the display unit goes down and up as opposed to when the user is at work.

Figure 32:
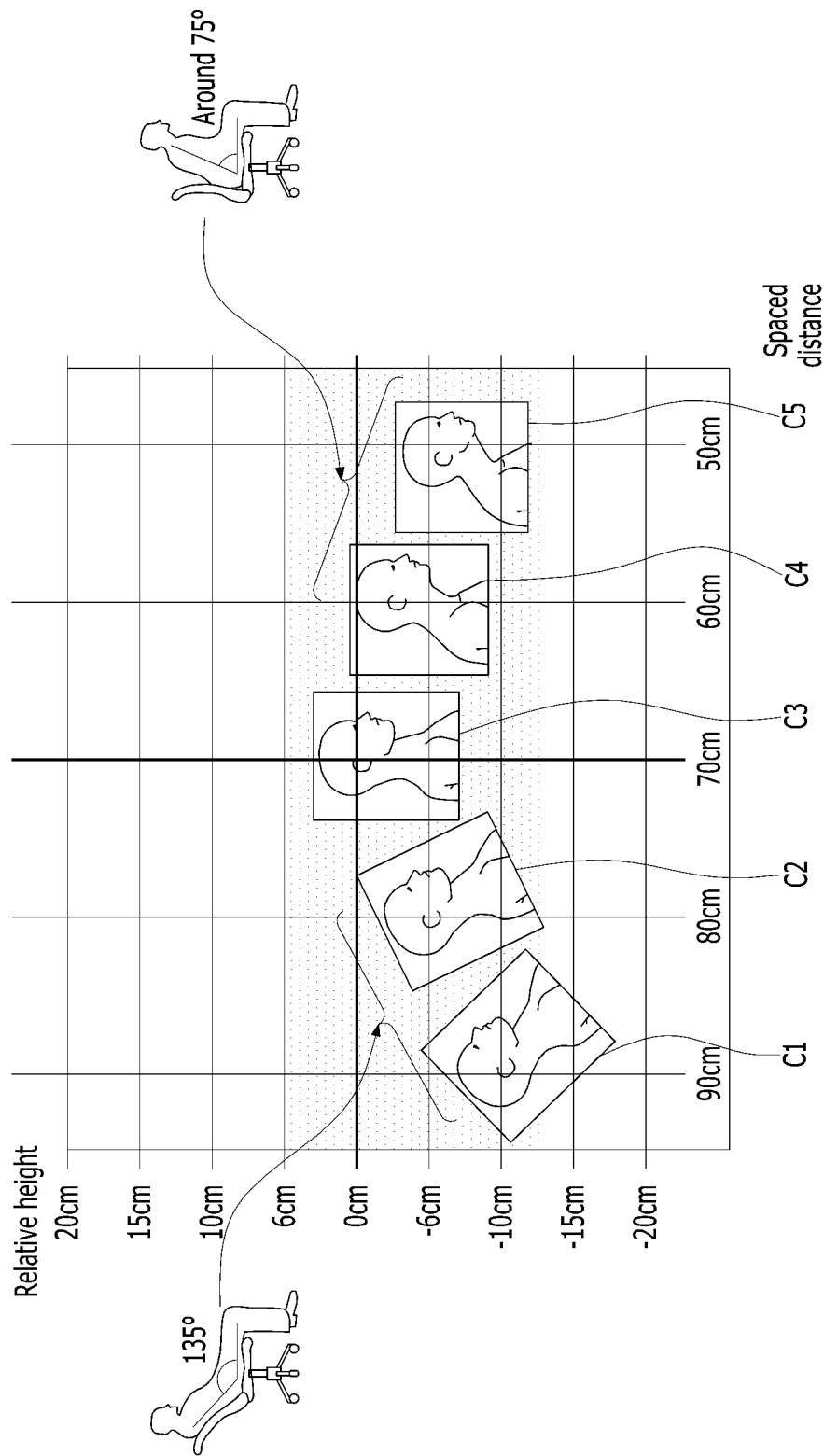
FIG. 32 is a diagram to describe a user's posture mode according to an embodiment of the present disclosure.

Hereinafter, the user's posture mode will be described further with reference to FIG. 32. In particular, FIG. 32 is a diagram to describe a user's posture mode according to an embodiment of the present disclosure.

Assume that the user is sitting with an upper body upright so that the user's face is spaced by a first distance (e.g., 70 cm) apart from the display unit 100 with a fixed posture (C3). In this instance, it is assumed that a user's eye level is the same as a center height of the display unit 100. However, when the user gradually lays the user's upper body back, the user's eye level gradually decreases from the center height of the display unit 100, and the user's face can gradually get far away from the display unit (C1, C2).

On the contrary, when the user gradually tilts the upper body forward, the user's eye level can gradually become lower than the center height of the display unit 100, and the user's face can get closer to the display unit (C4, C5). The postures such as C3, C4, and C5 are often taken when the user concentrates on work or study. Hereinafter, the user posture mode in which the user is likely to take during concentration will be referred to as a "concentration mode." Meanwhile, the posture such as C1 and C2 is often taken when the user relaxes during watching a movie or resting. In this way, the user posture mode in which the user is likely to take during relaxation is referred to as a "relax mode".

Hereinafter, the concentration mode and the relax mode will be further described with reference to FIG. 33. In particular, FIG. 33 is a diagram to describe a user's posture mode according to an embodiment of the present disclosure.

Figure 33:
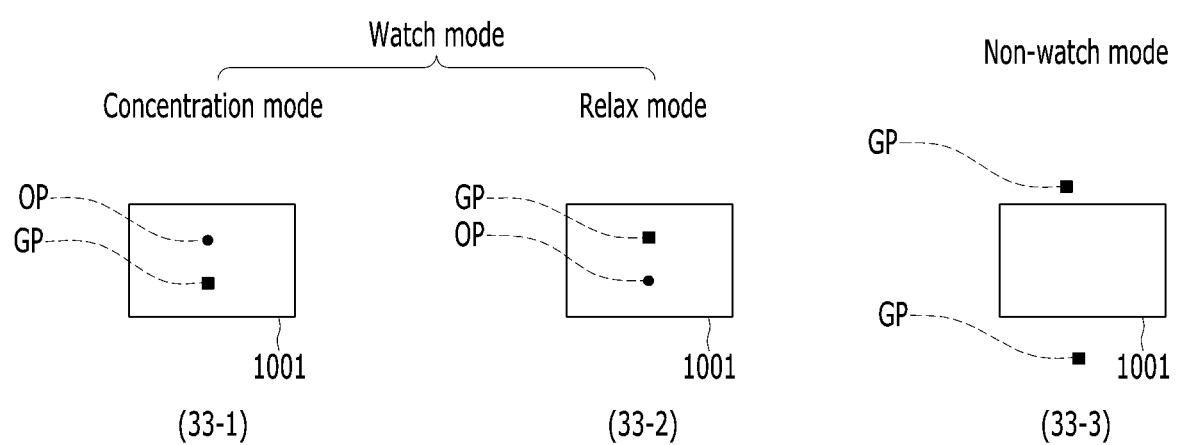
FIG. 33 is a diagram to describe a user's posture mode according to an embodiment of the present disclosure.

As illustrated in FIG. 33 (33-1), in the concentration mode, it may frequently happen that the gaze point GP is formed to be lower than the normal point OP on the display panel 1001. On the contrary, as illustrated in FIG. 33 (33-2), in the relax mode, it may frequently happen that the gaze point GP is formed higher than the normal point OP on the display panel 1001.

Therefore, the controller 350 can distinguish the concentration mode from the relaxation mode by further considering the positional relationship between the normal point OP and the gaze point GP as well as the inclination of the upper body of the user and the height of the head of the user, etc. In addition, the controller 350 can infer the distinguishment between the concentration mode and the relax mode from the user's posture using the artificial intelligence model that has learned the user's posture. The controller 350 can distinguish the concentration mode and the relax mode from each other through a user command for directly selecting one of the concentration mode and the relax mode, which can be input from the user through the signal input unit 355.

As illustrated in (33-1) and (33-2) of FIG. 33, the user's gaze point is formed within the display panel 1001 during the concentration mode and the relaxation mode. Accordingly, the concentration mode and the relaxation mode can be understood as a "watch mode."

However, as illustrated in (33-3) of FIG. 33, the user's gaze point can be formed outside the display panel 1001 irrespective of whether it is in the concentration mode or the relax mode. This can mean that the user is not watching the display panel 1001. Hereinafter, such a user posture mode will be referred to as a "non-watch mode."

Figure 34:
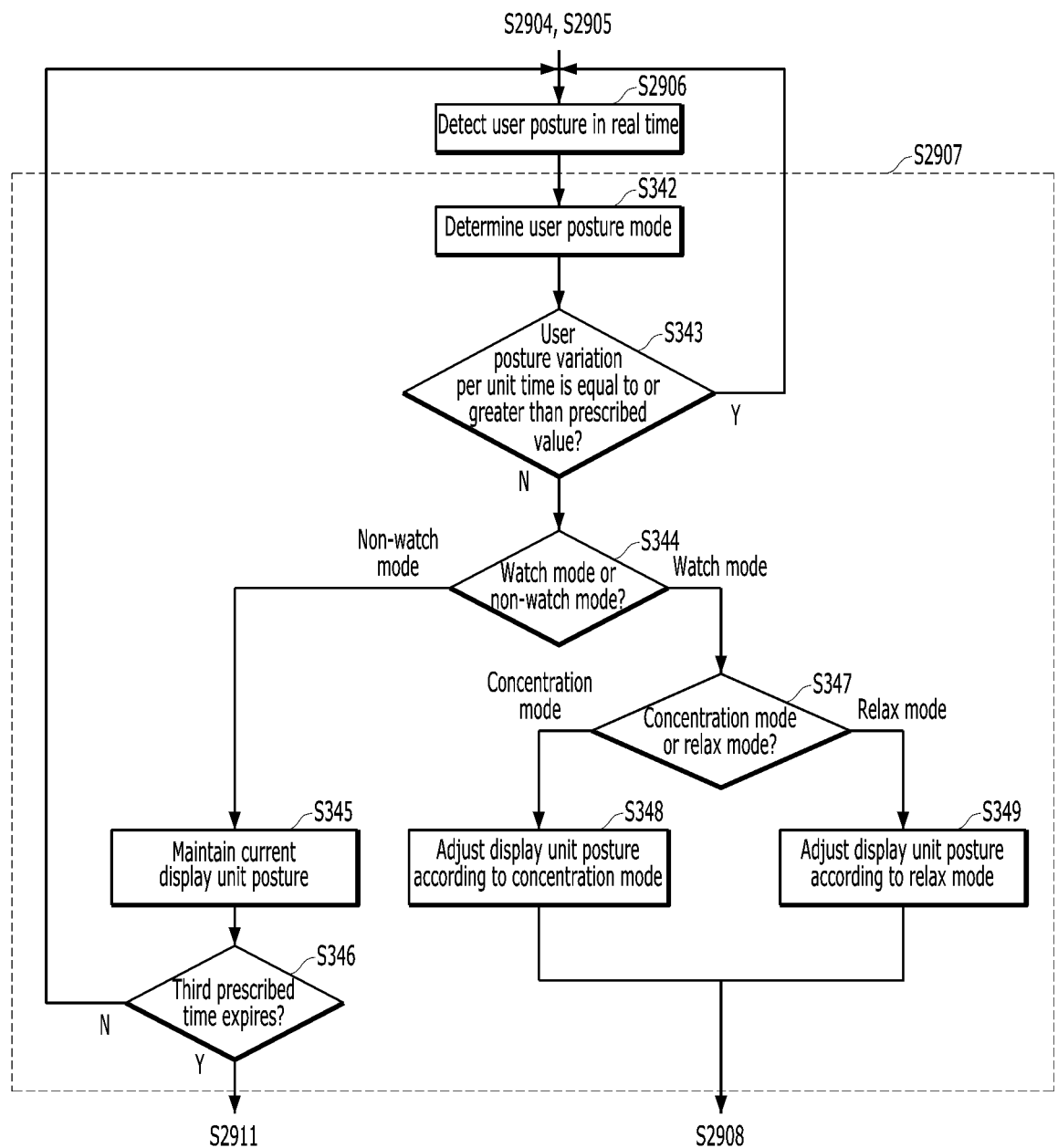
FIG. 34 is a flowchart illustrating posture adjustment of a display unit according to an embodiment of the present disclosure.

Hereinafter, with reference to FIG. 34, adjusting the posture of the display unit will be described by further considering the user posture mode. This can be understood as a detailed process of the step S2907 of FIG. 29. In particular, FIG. 34 is a flowchart illustrating a posture adjustment of a display unit according to an embodiment of the present disclosure.

As described with reference to FIG. 29, the controller 350 can obtain a user's image in real time through the camera 105, thereby detecting a user's posture in real time (S2906). The user's posture detection is as described above with reference to FIGS. 14 to 18.

The controller 350 can determine a user's posture mode based on the user's posture detected in the step S2906 (S342). The determination of the user's posture mode is the same as described above with reference to FIGS. 32 and 33. When the posture mode of the user is determined based on the user command, the step S342 can be performed before the step S2906.

The controller 350 can determine whether there is a rapid change in the detected user's posture (S343). For example, if the user stands up and sits down for a while to bring something, there can be a rapid change in the user's posture. Even in this instance, the posture of the display unit 100 according to the user's posture can be omitted. Therefore, if a user posture variation per unit time is greater than or equal to a prescribed value, the controller 350 can ignore the rapid posture change and perform the step S2906.

When the user posture variation per unit time is smaller than the prescribed value, the controller 350 can determine whether the user's posture mode corresponds to either the watch mode or the non-watch mode (S344). The determination of the watch mode and the non-watch mode is the same as described with respect to FIG. 33. If the user's posture mode is the non-watch mode, the controller 350 can control the current posture of the display unit 100, that is, the posture of the display unit 100 in the step S344, to be maintained (S345).

Next, the controller 350 can determine whether a time for maintaining the non-watch mode passes a third prescribed time (for example, 5 minutes) [S346]. The third prescribed time can be the same as or different from any one of the first prescribed time and the second prescribed time described above.

If the time for maintaining the non-watch mode has not passed the third prescribed time, the controller 350 can control the present process to proceed to the step S2906. When the time for maintaining the non-maintenance mode has elapsed a third predetermined time, the controller 350 can control the process to proceed to stage S2911.

In addition, when the user's posture mode is the watch mode, the controller 350 can determine whether the user's posture mode corresponds to the concentration mode or the relax mode (S347). If the user's posture mode is the concentration mode, the controller 350 can adjust the posture of the display unit 100 differently according to the adjustment mode selected in the step S2901 (S348), which will be described later.

However, if the user's posture mode is the relax mode, the controller 350 can adjust the display unit posture according to the relax mode (S349). For example, in the relax mode, in response to the user's face lowering, the controller 350 can adjust the posture of the display unit 100 so that the display unit 100 tilts downward as the height of the display unit 100 increases. This is to allow the user to comfortably view the display unit 100 upward in a backward inclined posture.

Figure 35:
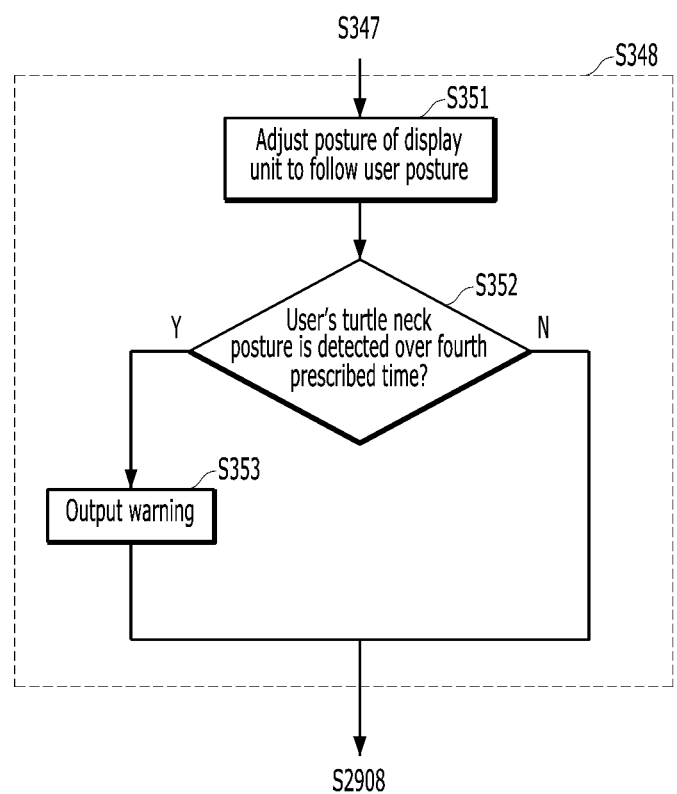
FIG. 35 is a flowchart illustrating posture adjustment of a display unit according to an embodiment of the present disclosure.

Hereinafter, with further reference to FIGS. 35 and 36, described is how to adjust the posture of the display unit 100 when the adjustment mode selected in the step S2901 is a first adjustment mode. This can be understood as a detailed process of the step S348 of FIG. 34. In particular, FIG. 35 is a flowchart illustrating a posture adjustment of a display unit according to an embodiment of the present disclosure, and FIG. 36 illustrates a relationship between a display unit posture and a user posture for describing posture adjustment of the display unit of FIG. 35.

When the adjustment mode selected in the step S2901 is a first adjustment mode, the controller 350 can adjust the posture of the display unit 100 to follow the detected user's posture (S351). That is, the controller 350 can adjust the posture of the display unit 100 to follow a user face position according to the detected user posture in real time so that the spatial relationship between the user face position according to the user's basic posture and the user-preferred display unit posture a can be maintained as it is. Here, following "in real time" means following the user's posture with a delay within a prescribed range when the user's posture changes over the prescribed range, and may not mean immediately following the user's posture if the user's posture changes even a little.

Figure 36:
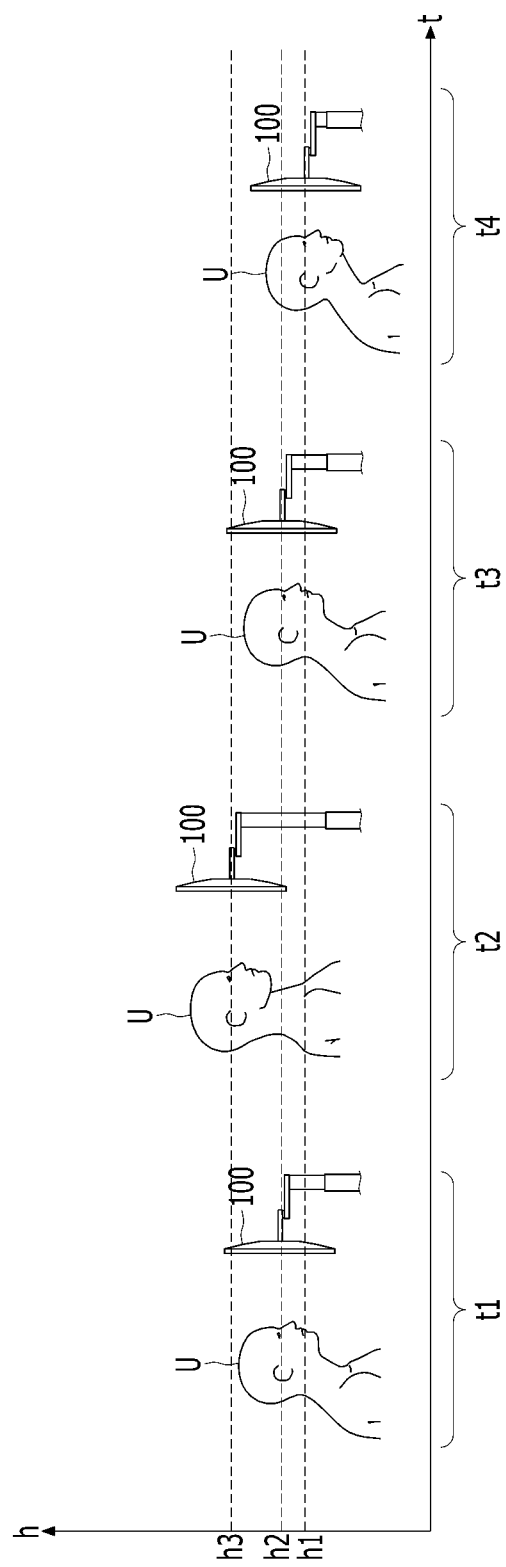
FIG. 36 illustrates a relationship between a display unit posture and a user posture for describing posture adjustment of the display unit of FIG. 35.

For example, as shown in FIG. 36, assume that the spatial relationship between the user face position according to the user's basic posture and the user-preferred display unit posture allows an eye level of the user U to be at the center height of the display unit 100. In this instance, both the eye level of the user U and the center height of the display unit can be at a second height h2 at a first time point t1.

However, as time flows from the first time point t1 to a second time point t2, the eye level of the user U can increase from the second height h2 to a third height h3. Then, the controller 350 can adjust the posture of the display unit 100 so that the center height of the display unit 100 goes from the second height h2 to the third height h3.

As time flows from the second time point t2 to a third time point t3, the eye level of the user U can be lowered from the third height h3 to the second height h2. Then, the controller 350 can adjust the posture of the display unit 100 so that the center height of the display unit 100 becomes the second height h2 from the third height h3.

Next, the controller 350 can determine whether or not the user is in a turtle neck posture for a fourth prescribed time or more (S352). The fourth prescribed time can be the same as or different from any one of the first to third prescribed times described above. Whether the user is in the turtle neck posture can be obtained from the 3D body skeleton and/or the 3D user face mesh. Alternatively, if the user's eye level according to the detected user's posture is lower than the user's eye level according to the user basic posture by a prescribed value or more, it can be determined that the user is in the turtle neck posture.

When it is detected that the user has been in the turtle neck posture for more than the fourth prescribed time, the controller 350 can control a warning, which warns that the user is in the turtle neck posture, to be outputted (S353). For example, the warning can be displayed in the form of an On Screen Display (OSD) at a prescribed position of the display panel 1001.

Referring further to FIG. 36, as time flows from the third time point t3 to the fourth time point t4, the user U can maintain the turtle neck posture for the fourth prescribed time as the eye level of the user U decreases from the second height h2 to the first height h1. Then, the controller 350 can control the display unit 100 to output the warning while adjusting the posture of the display unit 100 so that the center height of the display unit 100 goes from the second height h2 to the first height h1.

The controller 350 can control the present process to proceed to the step S2908 after the step S353. If it has not been detected whether the user is in the turtle-neck posture for more than the fourth prescribed time, the controller 350 can control the present process to proceed directly to the step S2908.

In addition, in adjusting the posture of the display unit 100 to follow the user face position according to the detected user posture in real time, a following degree can vary depending on a spaced distance between the user face and the display unit 100. That is, the following degree can be inversely proportional to the spaced distance. For example, when the spaced distance is smaller than a predetermined distance, the controller 350 can control the posture of the display unit 100 to follow the user face position in real time so that the following degree becomes 100%.

When the spaced distance is equal to or greater than the predetermined distance, the controller 350 can control the posture of the display unit 100 to follow the user face position in real time so that the following degree becomes smaller than 100%. That is, if the user face is close to the display unit 100, the display unit 100 can move up and down as much as the distance in which the user face has moved up and down. Yet, if the user face is far from the display unit 100, the display unit 100 can move up and down in a distance smaller than the user face has moved up and down.

Figure 37:
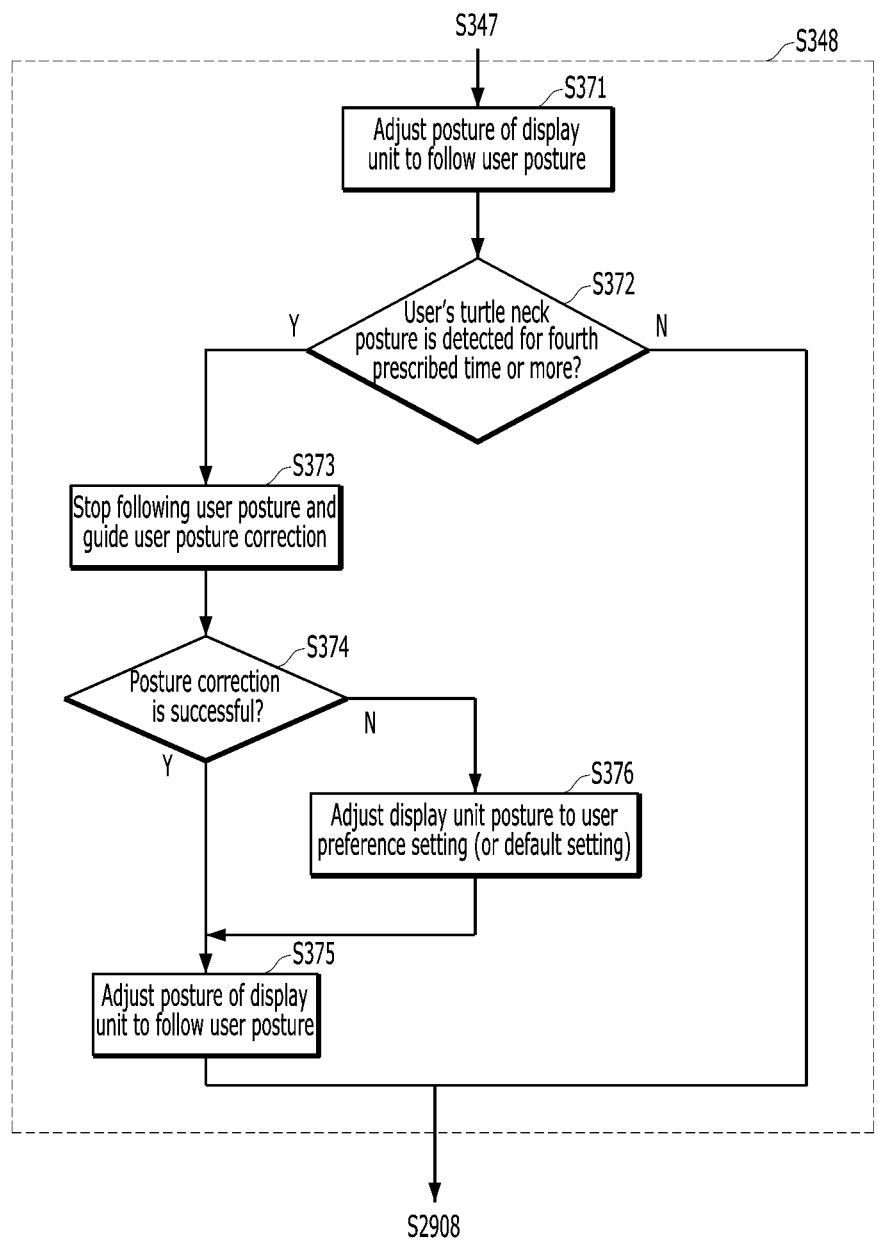
FIG. 37 is a flowchart illustrating posture adjustment of a display unit according to an embodiment of the present disclosure.

Hereinafter, with further reference to FIGS. 37 and 38, described is how to adjust the posture of the display unit 100 when the adjustment mode selected in the step S2901 is the second adjustment mode. This can be understood as a detailed process of the step S348 of FIG. 34. In particular, FIG. 37 is a flowchart illustrating a posture adjustment of a display unit according to an embodiment of the present disclosure, and FIG. 38 illustrates a relationship between a display unit posture and a user posture for describing posture adjustment of the display unit of FIG. 37.

When the adjustment mode selected in the step S2901 is a second adjustment mode, the controller 350 can adjust the posture of the display unit 100 to follow the detected user's posture (S371). That is, the controller 350 can adjust the posture of the display unit 100 to follow a user face position according to the detected user posture so that the spatial relationship between a user face position according to the user basic posture and the user-preferred display unit posture can be maintained as it is.

Figure 38:
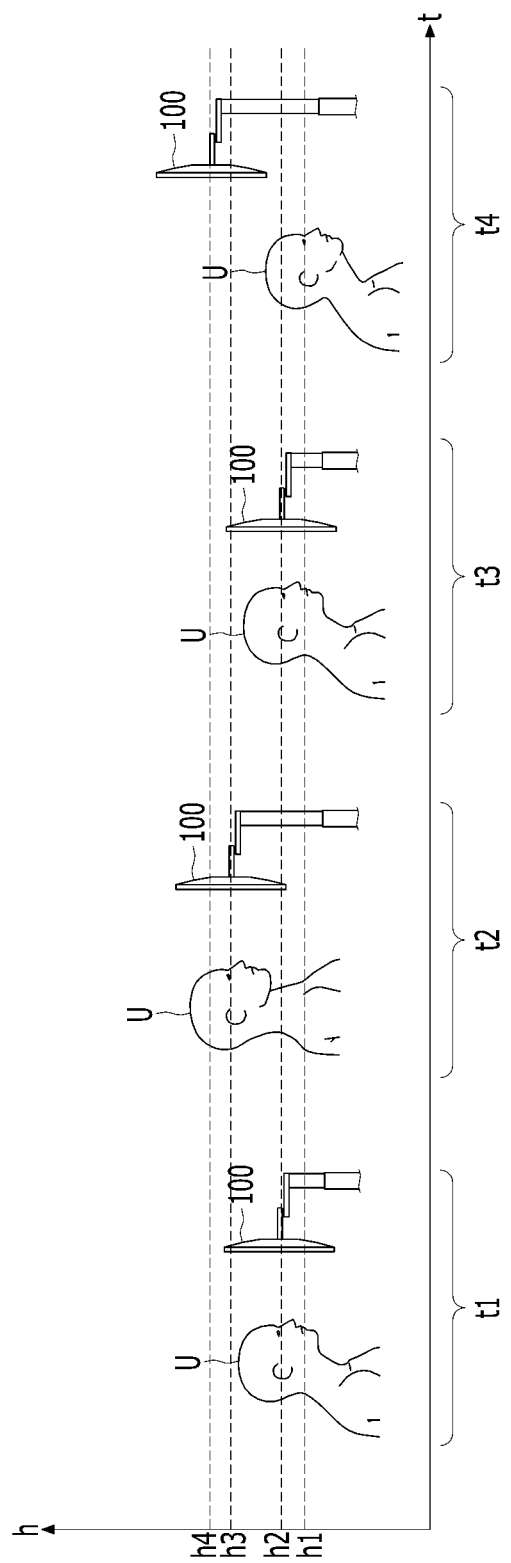
FIG. 38 illustrates a relationship between a display unit posture and a user posture for describing posture adjustment of the display unit of FIG. 37.

For example, as illustrated in FIG. 38, assume that the spatial relationship between the user face position according to the user basic posture and the user-preferred display unit posture allows a user's eye level to be at the center height of the display unit. In this instance, both the eye level of the user U and the center height of the display unit can be at a second height h2 at a first time point t1.

However, as time flows from the first time point t1 to a second time point t2, the eye level of the user U can increase from the second height h2 to a third height h3. Then, the controller 350 can adjust the posture of the display unit 100 so that the center height of the display unit 100 goes from the second height h2 to the third height h3.

As time flows from the second time point t2 to a third time point t3, the eye level of the user U can be lowered from the third height h3 to the second height h2. Then, the controller 350 can adjust the posture of the display unit 100 so that the center height of the display unit 100 becomes the second height h2 from the third height h3.

Next, the controller 350 can determine whether or not the user is in a turtle neck posture for a fourth prescribed time or more (S372). The fourth prescribed time can be the same as or different from any one of the first to third prescribed times described above. Whether the user is in a turtle-neck posture can be determined from the 3D body skeleton and/or the 3D user face mesh. Alternatively, if the user's eye level according to the detected user's posture is lower than the user's eye level according to the user basic posture by a prescribed value or more, it can be determined that the user is in the turtle neck posture.

When it is detected that the user has been in the turtle neck posture for more than the fourth prescribed time, the controller 350 can stop adjusting the posture of the display unit 100 to follow the user's posture of the user. In addition, the controller 350 can adjust the posture of the display unit 100 to correct the user's posture.

Referring further to FIG. 38, as time flows from the third time point t3 to a fourth time point t4, the user U can maintain a turtle neck posture for a fourth prescribed time as the eye level of the user U decreases from the second height h2 to the first height h1. Then, the controller 350 does not adjust the posture of the display unit 100 so that the center height of the display unit 100 becomes the first height h1 from the second height h2. Instead, the controller 350 can control the center height of the display unit 100 to gradually increase at a predetermined speed to a maximum height h4 until the user U is out of the turtle neck posture. This is to guide the user U to move out of the turtle neck posture by raising a user's head along the rising display unit 100. The prescribed speed can be a speed that the user does not easily recognize that the center height of the display unit 100 is increasing. Alternatively, the prescribed speed can be a speed enough for the user to consciously correct his or her turtle neck posture by easily recognizing that the center height of the display unit 100 is increasing. The controller 350 can output a warning, which warns that the user is in the turtle neck posture.

The controller 350 can determine whether the user U is out of the turtle neck posture, that is, whether the user's posture is corrected, while gradually increasing the center height of the display unit 100 to the maximum height h4 (S374). If the user's posture is corrected, the controller 350 can adjust the posture of the display unit 100 to follow the detected user's posture (S375). This is the same as described in the step S371.

However, although the center height of the display unit 100 is raised to the maximum height h4, if the user's posture is not corrected, the controller 350 can control the display unit 100 to perform the step S375 after adjusting the center height of the display unit 100 according to the user preference setting or the default setting (S376, S375).

Although the central height of the display unit 100 is raised to the maximum height h4, if the user's posture is not corrected, the controller 350 can control to the step S375 to be executed without performing the step S376. The controller 350 can control the present process to proceed to the step S2908 after the step S375. In addition, in adjusting the posture of the display unit 100 to follow the user face position according to the detected user posture in real time, the following degree can also vary depending on a spaced distance between the user face and the display unit 100.

Figure 39:
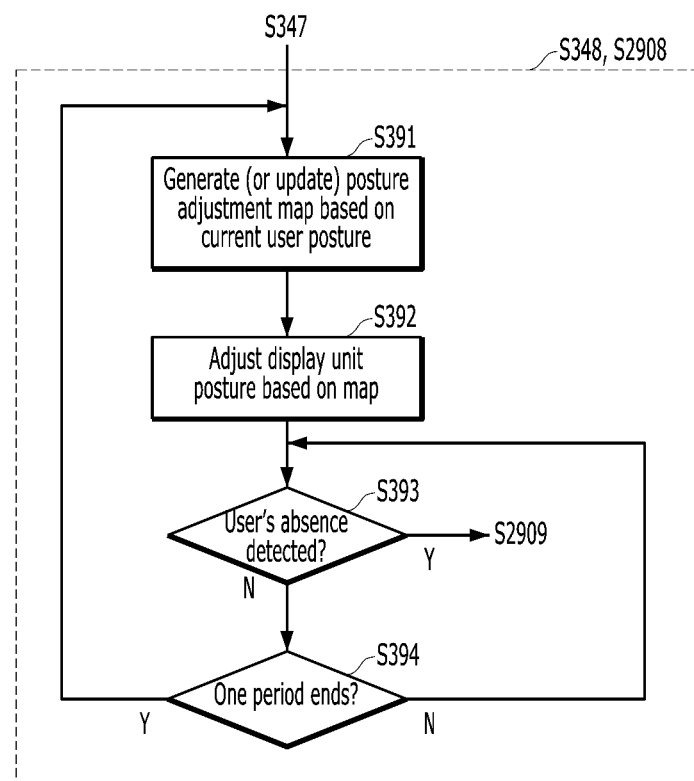
FIG. 39 is a flowchart illustrating posture adjustment of a display unit according to an embodiment of the present disclosure.
Figure 40:
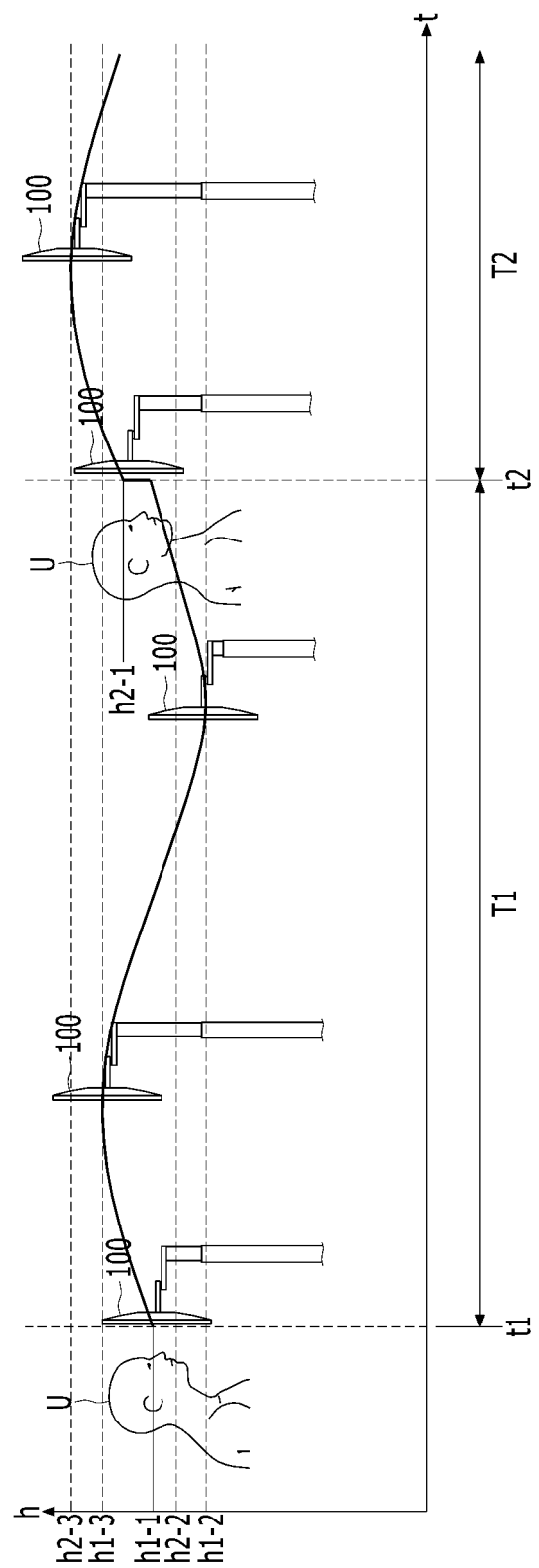
FIG. 40 illustrates a relationship between a display unit posture and a user posture for describing posture adjustment of the display unit of FIG. 39.

Hereinafter, with further reference to FIGS. 39 and 40, described is how to adjust the posture of the display unit 100 when the adjustment mode selected in the step S2901 is a third adjustment mode. This can be understood as a detailed process of the steps S348 and S2908 of FIG. 34. In particular, FIG. 39 is a flowchart illustrating posture adjustment of a display unit according to an embodiment of the present disclosure, and FIG. 40 illustrates a relationship between a display unit posture and a user posture for describing posture adjustment of the display unit of FIG. 39.

When the adjustment mode selected in the step S2901 is a third adjustment mode, the controller 350 can generate a posture adjustment map for the display unit 100 based on the detected user's posture (S391). Then, the controller 350 can adjust the posture of the display unit 100 based on the generated posture adjustment map (S392).

The posture adjustment of the display unit 100 based on the generated posture adjustment map will be described with further reference to FIG. 40. It is assumed that the spatial relationship between the user face position according to the user basic posture and the user-preferred display unit posture allows the eye level of the user U to be at the center height of the display unit 100. The controller 350 can generate a posture adjustment map for the display unit 100 based on the posture of the user U detected at the time of generating the posture adjustment map (S391).

In generating the posture adjustment map, the controller 350 can determine an initial center height of the display unit 100 to meet a user face height (more specifically, the user's eye level) according to the detected user posture so that the spatial relationship between the user face position according to the user basic posture and the user-preferred display unit posture can be maintained intact. For example, the controller 350 can set the initial center height of the display unit 100 to a height 1-1 (h1-1) so as to be at the user's eye level according to the detected user posture.

Next, the controller 350 can generate the posture adjustment map so that the center height of the display unit 100 has a height fluctuation in amplitude according to a sinusoidal curve trajectory for a first period T1 (for example, 1 hour) around the initial center height h1-1 (S391). In the height fluctuation according to the sinusoidal curve trajectory, a lowest point center height of the display unit 100 can be a height 1-2 (h1-2), and a highest point center height of the display unit 100 can be a height 1-3 (h1-3).

A height difference between the height 1-1 (h1-1) and the height 1-2 (h1-2) and a height difference between the height 1-1 (h1-1) and the height 1-3 (h1-3) can be the same. However, the height difference between the height 1-2 (h1-2) and the height 1-3 (h1-3) can be a relatively small value (e.g., 6 cm) so that the user U may not easily recognize it. That is, since the display unit 100 is adjusted to a height of about 6 cm during the first period (e.g., 1 hour), the user U may not easily recognize the posture adjustment of the display unit 100. However, since the user U may unconsciously move his or her posture to follow the adjusted posture of the display unit 100, physical fatigue, which can occur if a fixed posture is maintained for a long time, can be prevented in advance.

The controller 350 can adjust the posture of the display unit 100 so that the center height of the display unit 100 continuously follows the sinusoidal curve trajectory of the posture adjustment map from a first time point t1 during the first period T1. In addition, while the posture of the display unit 100 is adjusted according to the posture adjustment map, the controller 350 can detect whether the user is absent from a seat (i.e., 'away from seat') (S393).

When the user's absence is detected, the controller 350 can delete the posture adjustment map and control the present process to proceed to the step S2909. If the user's absence is not detected, the controller 350 can determine whether the first period T1 ends. When the first period T1 does not end, the controller 350 can control the process to proceed to the step S393.

However, when the first period T1 ends, the controller 350 can control the present process to proceed to the step S391. The controller 350 can update the posture adjustment map (S391). That is, the controller 350 can update the posture adjustment map for the display unit 100 based on the posture of the user U detected at the time when the posture adjustment map is to be updated. In updating the posture adjustment map, the controller 350 can set the initial center height of the display unit 100 to a height 2-1 (h2-1) so as to become the user's eye level according to the detected user posture.

Next, the controller 350 can update the posture adjustment map in which the center height of the display unit 100 has a height fluctuation in amplitude according to the sinusoidal curve trajectory for a second period T2 (e.g., 1 hour) around the initial center height h2-1. The length of the second period can be the same as the first period. In the height fluctuation according to the sinusoidal curve trajectory, a lowest point center height of the display unit 100 can be a height 2-2 (h2-2) and a highest point center height of the display unit 100 can be a height 2-3 (h2-3).

A height difference between the height 2-1 (h2-1) and the height 2-2 (h2-2) can be the same as the height difference between the height 1-1 (h1-1) and the height 1-2 (h1-2) described above. In addition, a height difference between the height 2-1 (h2-1) and the height 2-3 (h2-3) can be the same as the height difference between the height 1-1 (h1-1) and the height 1-3 (h1-3).

The controller 350 can adjust the posture of the display unit 100 so that the center height of the display unit 100 continuously follows the sinusoidal curve trajectory of the updated posture adjustment map for the second period from a second time point t2 (S392). Further, the lengths of the first and second periods and/or the magnitude of the amplitude according to the sinusoidal curve trajectory can be adjusted by the user through the signal input unit 355.

Alternatively, the lengths of the first period and the second period and/or the magnitude of the amplitude according to the sinusoidal curve trajectory can be automatically adjusted according to the user basic posture. For example, if the user's eye level in the user basic posture is relatively high, the lengths of the first period and the second period and/or the magnitude of the amplitude according to the sinusoidal curve trajectory can be automatically adjusted to increase. If the user's eye level in the user basic posture is relatively low, the lengths of the first period and the second period and/or the magnitude of the amplitude according to the sinusoidal curve trajectory can be automatically adjusted to decrease.

Alternatively, while the height of the display unit is being adjusted according to the sinusoidal curve trajectory, the change in the user's eye level can be too large or too small. If the change in the user's eye level is too large, the magnitude of the amplitude according to the sinusoidal curve trajectory can be automatically adjusted to increase. If the change in the user's eye level is too small, the magnitude of the amplitude can be automatically adjusted to decrease. The automatic adjustment can be performed during one cycle, and can be performed after one cycle is completed.

Although the center height of the display unit is described as following a sinusoidal curve trajectory of one cycle during the first period or the second period, the present disclosure is not limited thereto. Also, the center height of the display unit can follow a sinusoidal curved trajectory longer than or shorter than one cycle during the first or second period.

In the above description, the height adjustment of the display unit has been mainly described in describing the posture adjustment map. However, the posture adjustment map does not necessarily have to be generated only for the height adjustment of the display unit. For example, the posture adjustment map can be generated so that the display unit 100 tilts downward by a predetermined angle at the height of the highest point of the display unit 100 and the display unit 100 tilts upward by a predetermined angle at the height of the lowest point of the display unit 100.

In addition, in the above description, the posture adjustment map of the sinusoidal curve trajectory corresponding to a middle height (i.e., average height) (h1-1, h2-1) between the lowest point center height (h1-2, h2-2) and the highest point center height (h1-3, h2-3) is generated. Yet, the posture adjustment map may not be necessarily generated by such a method. This will be described with further reference to FIGS. 41 to 44. In particular, FIGS. 41 to 44 illustrate modifications of a posture adjustment map according to FIG. 40.

Figure 41:
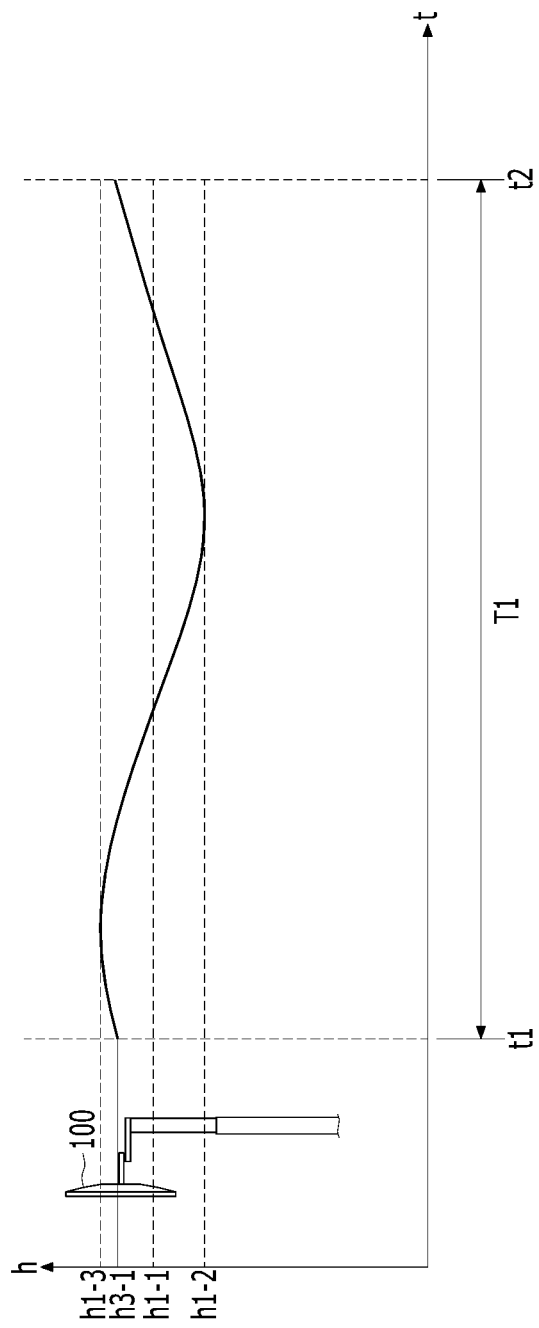
FIGS. 41 to 43 illustrate modifications of a posture adjustment map according to FIG. 40.

As illustrated in FIG. 41, before adjusting the posture of the display unit 100 according to the posture adjustment map, that is, before a first time point t1, a center height of the display unit 100 can be a height 3-1 (h3-1) different from the middle height h1-1 between the lowest point center height h1-2 and the highest point center height h1-3 despite being located between them.

In this instance, the controller 350 can generate the posture adjustment map to have the height fluctuations of amplitude according to the sinusoidal curve trajectory in which the initial center height, the lowest point center height and the highest point center height of the display unit 100 become a height 3-1 (h3-1), a height 1-2 (h1-2), and a height 1-3 (h1-3) during the first period T1, respectively.

Figure 42:
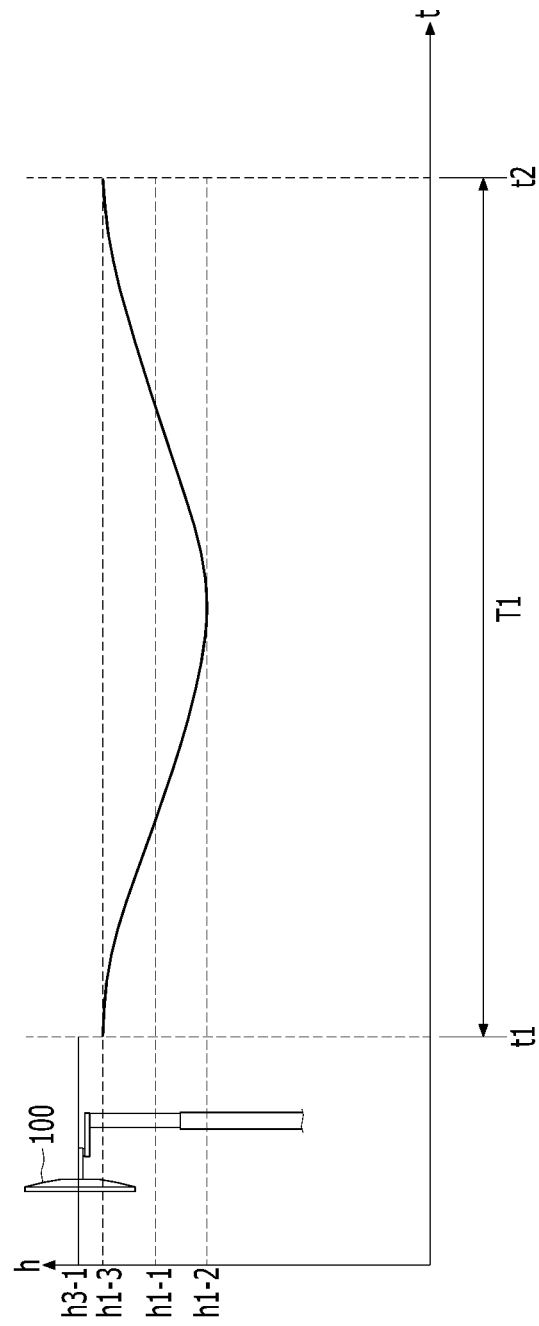
Figure 43:
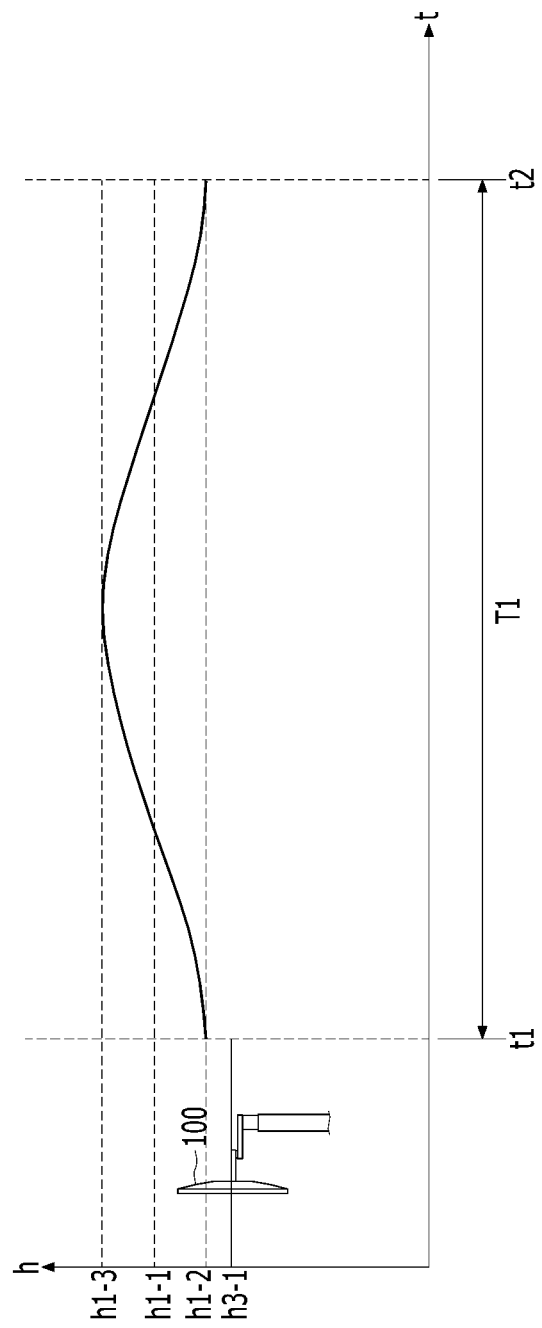

As illustrated in FIG. 42, before adjusting the posture of the display unit 100 according to the posture adjustment map, that is, before the first time point t1, the center height of the display unit 100 can be a height 3-2 (h3-2) higher than the highest point center height h1-3. In this instance, the controller 350 can generate the posture adjustment map to have the height fluctuations of amplitude according to the sinusoidal curve trajectory in which the initial center height, the highest point center height and the lowest point center height of the display unit 100 become the height 1-3 (h1-3), the height 1-3 (h1-3), and the height 1-2 (h1-2) during the first period T1, respectively.

Yet, in adjusting the posture of the display unit 100 according to the posture adjustment map, the controller 350 can control the center height of the display unit 100 to be adjusted according to the sinusoidal curve trajectory of the posture adjustment map after the center height of the display unit 100 is rapidly changed from the height 3-2 (h3-2) to the height 1-3 (h1-3) at the first time point t1.

As illustrated in FIG. 42, before adjusting the posture of the display unit 100 according to the posture adjustment map, that is, before the first time point t1, the center height of the display unit 100 can be a height 3-3 (h3-3) lower than the lowest point center height h1-2. In this instance, the controller 350 can generate the posture adjustment map to have the height fluctuations of amplitude according to the sinusoidal curve trajectory in which the initial center height, the lowest point center height and the highest point center height of the display unit 100 become the height 1-2 (h1-2), the height 1-2 (h1-2), and the height 1-3 (h1-3) during the first period T1, respectively.

In adjusting the posture of the display unit 100 according to the posture adjustment map, the controller 350 can control the center height of the display unit 100 to be adjusted according to the sinusoidal curve trajectory of the posture adjustment map after the center height of the display unit 100 is rapidly changed from the height 3-3 (h3-3) to the height 1-2 (h1-2) at the first time point t1.

Figure 44:
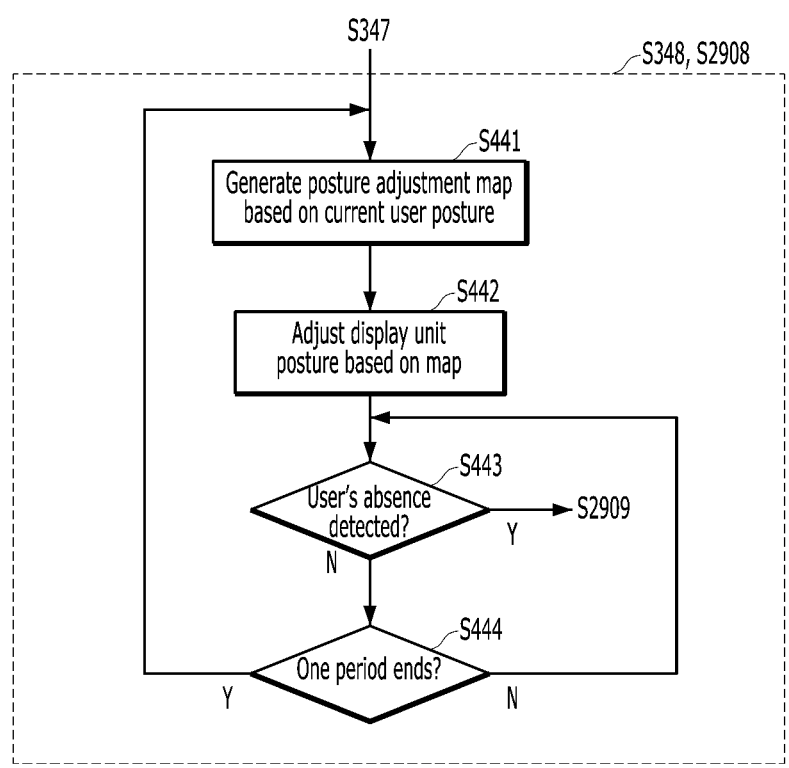
FIG. 44 is a flowchart illustrating posture adjustment of a display unit according to an embodiment of the present disclosure.
Figure 45:
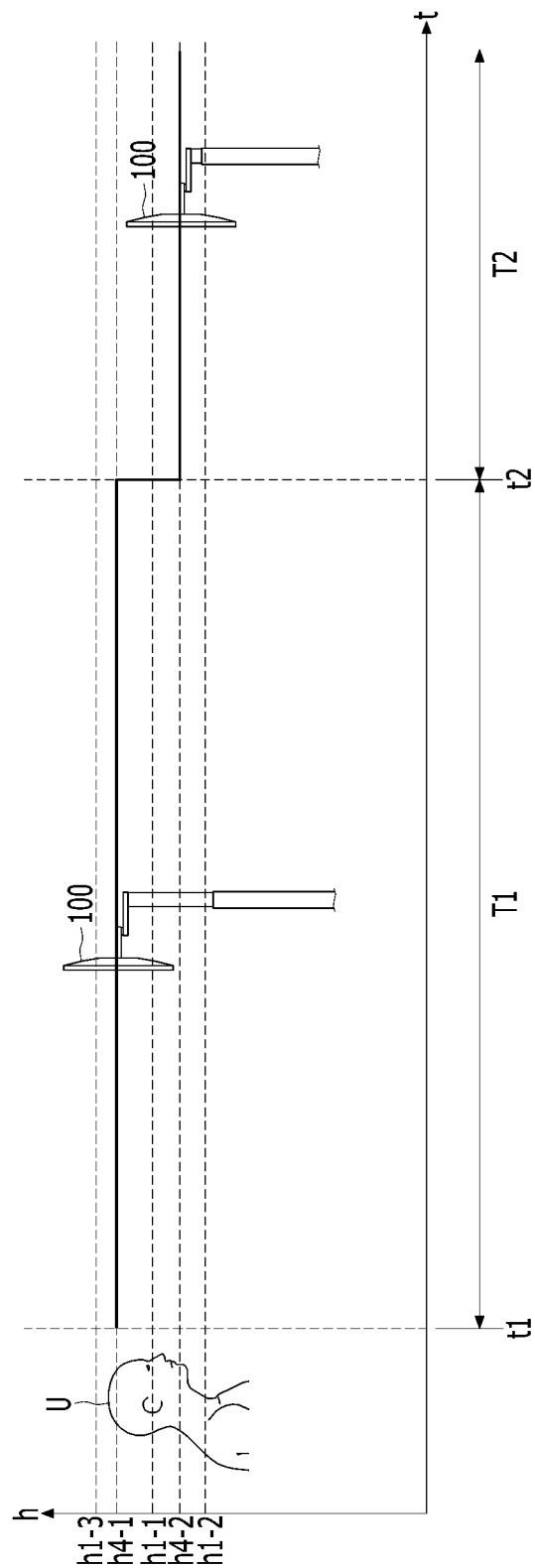
FIG. 45 illustrates a relationship between a display unit posture and a user posture for describing posture adjustment of the display unit of FIG. 44.

Hereinafter, with further reference to FIGS. 44 and 45, described is how to adjust the posture of the display unit 100 when the adjustment mode selected in the step S2901 is a fourth adjustment mode. This can be understood as a detailed process of the steps S348 and S2908 of FIG. 34. In particular, FIG. 44 is a flowchart illustrating posture adjustment of a display unit according to an embodiment of the present disclosure. FIG. 45 illustrates a relationship between a display unit posture and a user posture for describing posture adjustment of the display unit of FIG. 44.

When the adjustment mode selected in the step S2901 is a fourth adjustment mode, the controller 350 can generate a posture adjustment map for the display unit 100 based on the detected user's posture (S441). In addition, the controller 350 can adjust the posture of the display unit 100 based on the generated posture adjustment map (S442).

The posture adjustment of the display unit 100 based on the generated posture adjustment map will be described with further reference to FIG. 45. Assume that the spatial relationship between the user face position according to the user basic posture and the user-preferred display unit posture allows the eye level of the user U to be at the center height of the display unit 100. The controller 350 can generate a posture adjustment map for the display unit 100 based on the posture of the user U detected at the time when the posture adjustment map is to be generated (S441).

In generating the posture adjustment map, the controller 350 can determine an initial height of the display unit 100 to match a user face height according to the detected user posture so that the spatial relationship between the user face position according to the user basic posture and the user-preferred display unit posture is maintained intact. For example, the controller 350 can determine an initial center height of the display unit 100, that is, a height 1-1 (h1-1), so as to become a user's eye level according to the detected user posture.

Then, in generating the posture adjustment map, the controller 350 can determine a lowest point center height, i.e., a height 1-2 (h1-2), of the display unit 100, which is lower than the height 1-1 (h1-1) by a prescribed height, and a highest point center height, i.e., a height 1-3 (h1-3), of the display unit 100 which is higher than the height 1-1 (h1-1) by the prescribed height. The prescribed height can be a relatively small value (for example, 3 cm) so as not to be easily recognized by the user U.

The controller 350 can adjust the posture of the display unit 100 so that a center height of the display unit 100 can maintain a random height between the height 1-2 (h1-2) that is the lowest point center height and the height 1-3 (h1-3) that is the highest point center height, i.e., a height 4-1 (h4-1) during a first period T1 from a first time point t1 [S442]. In addition, while the posture of the display unit 100 is adjusted according to the posture adjustment map, the controller 350 can detect whether the user is absent from a seat (i.e., away-from-seat) (S443).

When the user's absence is detected, the controller 350 can delete the posture adjustment map and control the present process to proceed to the step S2909. If the user's absence is not detected, the controller 350 can determine whether the first period T1 ends [S444].

If the first period T1 does not end, the controller 350 can control the present process to proceed to the step S443. Yet, if the first period T1 ends, the controller 350 can control the present process to proceed to the step S442. Namely, the controller 350 can adjust the posture of the display unit 100 so that a center height of the display unit 100 can maintain another random height between the height 1-2 (h1-2) that is the lowest point center height and the height 1-3 (h1-3) that is the highest point center height, i.e., a height 4-2 (h4-2) during a second period T2 from a second time point t2 (S442).

The present disclosure described above may be implemented as computer-readable code on a medium in which a program is recorded. Computer-readable media include all types of recording devices in which data readable by a computer system is stored. Examples of computer-readable media include Hard Disk Drives (HDDs), Solid State Disks (SSDs), Silicon Disk Drives (SDDs), ROMs, RAMs, CD-ROMs, magnetic tapes, floppy disks, optical data storage devices, etc. The computer may also include a processor of an artificial intelligence device. Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. The processor may include a processor of an AI device.

What is claimed is:

1. A display device comprising:
   a display unit having a display panel and a camera;
   a posture adjustment driving unit configured to adjust a posture of the display unit; and
   a controller configured to:
   control the camera to capture a first image of a viewer viewing the display unit when the display unit is positioned at a first height,
   control the posture adjustment driving unit to move the display unit to a second height different than the first height,
   control the camera to capture a second image of the viewer viewing the display unit when the display unit is positioned at the second height,
   correct at least one of the first image and the second image based on orientation information of the display unit on capturing the first image and the second image,
   generate a 3D body mesh of the viewer using the first image and the second image,
   calculate a viewer-optimized display unit posture setting based on the 3D body mesh,
   control the posture adjustment driving unit to move the display unit to a height corresponding to the viewer-optimized display unit posture setting,
   calculate a first pixel distance between two feature points of the viewer from the first image and the second image,
   calculate a first spaced distance from the camera to the viewer based on the first pixel distance between the two feature points of the viewer,
   store data in a memory about the first spaced distance and the first pixel distance,
   control the camera to capture a third image of the viewer,
   calculate a second pixel distance between the two feature points of the viewer from the third image,
   calculate a second spaced distance from the camera to the viewer based on the second pixel distance between the two feature points of the viewer,
   control the posture adjustment driving unit to adjust the posture of the display unit based on the second spaced distance from the camera to the viewer,
   determine if the viewer moved horizontally in the second image and the third image, and
   store the data about the first spaced distance and the first pixel distance if a horizontal movement of the viewer in the second image and the third image is within a prescribed pixel distance.

2. The display device of claim 1, wherein the controller is further configured to:
   calculate the first spaced distance and the first pixel distance based on the corrected at least one of the first image and the second image.

3. The display device of claim 2, wherein the controller is further configured to:
   calculate the second pixel distance based on 2D landmark information calculated from the third image.

4. The display device of claim 3, wherein the controller is further configured to:
   correct the second pixel distance based on 3D body skeleton information calculated from the third image.

5. The display device of claim 1, wherein the two feature points of the viewer are both eyes.

6. The display device of claim 1, wherein the controller is further configured to:
   detect a user posture in the third image based on the second spaced distance, and
   control the posture adjustment driving unit based on the detected user posture in the third image.

7. The display device of claim 1, further comprising:
   an input interface configured to receive a viewer input,
   wherein the controller is further configured to:
   correct the viewer-optimized display unit posture setting based on the received input.

8. The display device of claim 7, wherein the controller is further configured to:
   store the corrected viewer-optimized display unit posture setting as a viewer preference setting in the memory, and
   control the posture adjustment driving unit to adjust the posture of the display unit in further consideration of the viewer preference setting.

9. The display device of claim 8, wherein the controller is further configured to:
   control the posture adjustment driving unit based on a spatial relationship between a viewer posture on capturing the second image and a third image and the viewer preference setting.

10. The display device of claim 9, wherein the controller is further configured to:
    control the posture adjustment driving unit to maintain the spatial relationship so a posture of the display unit follows the viewer posture.

11. The display device of claim 10, wherein a viewer posture mode includes a viewing mode and a non-viewing mode, and
    wherein the controller is further configured to:
    for the viewing mode, control the posture adjustment driving unit so the posture of the display unit to follows the viewer posture, and
    for the non-viewing mode, control the posture adjustment driving unit so the posture of the display unit does not follow the viewer posture.

12. The display device of claim 11, wherein the viewing posture mode includes a concentration mode and a relax mode, and
    wherein for the concentration mode, the controller controls the posture adjustment driving unit so the display unit moves in a same direction as a viewer eye level according to the viewer posture.

13. The display device of claim 12, wherein for the relax mode, the controller controls the posture adjustment driving unit to increase a height of the display unit as the viewer eye level decreases.

14. The display device of claim 12, wherein if the viewer posture includes a turtle neck posture with the head of the viewer protruding toward the display unit, the controller outputs a turtle neck posture warning.

15. The display device of claim 12, wherein if the viewer posture is a turtle neck posture with the head of the viewer protruding toward the display unit, the controller controls the posture adjustment driving unit to increase a height of the display unit.

16. The display device of claim 15, wherein the controller is further configured to:
control the posture adjustment driving unit to increase the height of the display unit until the viewer changes their posture out of the turtle neck posture.

17. A method of controlling a display device having a display panel, a camera, and a posture adjustment driving unit configured to adjust a posture of the display unit, the method comprising:
capturing, via the camera, a first image of a viewer viewing the display unit in a first posture when the display unit is positioned at a first height;
moving, via the posture adjustment driving unit, the display unit to a second height different than the first height;
capturing, via the camera, a second image of the viewer viewing the display unit in the first posture when the display unit is positioned at the second height;
correcting, via a controller, at least one of the first image and the second image based on orientation information of the display unit on capturing the first image and the second image;
generating, via the controller, a 3D body mesh of the viewer using the first image and the second image;
calculating, via the controller, a viewer-optimized display unit posture setting based on the 3D body mesh;
controlling, via the controller, the posture adjustment driving unit to move the display unit to a height corresponding to the viewer-optimized display unit posture setting;
calculating, via a controller, a first pixel distance between two feature points of the viewer from the first image and the second image;
calculating, via the controller, a first spaced distance from the camera to the viewer based on calculated first pixel distance between the two feature points of the viewer;
storing, via the controller, data in a memory about the first spaced distance and the first pixel distance;
capturing, via the camera, a third image of the viewer;
calculating, via the controller, a second pixel distance between the two feature point of the viewer from the third image;
calculating, via the controller, a second spaced distance from the camera to the viewer based on the second pixel distance between the two feature points of the viewer, and control the posture adjustment driving unit to adjust the posture of the display unit based on the second spaced distance from the camera to the viewer;
determining, via the controller, if the viewer moved horizontally in the second image and the third image;
storing, via the controller, the data about the first spaced distance and the first pixel distance if a horizontal movement of the viewer in the second image and the third image is within a prescribed pixel distance;
calculating, via the controller, the first spaced distance and the first pixel distance based on the corrected at least one of the first image and the second image;
calculating, via the controller, the second pixel distance based on 2D landmark information calculated from the third image; and
correcting, via the controller, the second pixel distance based on 3D body skeleton information calculated from the third image.

* * * * *